US009677085B2

(12) United States Patent
Guye et al.

(10) Patent No.: US 9,677,085 B2
(45) Date of Patent: Jun. 13, 2017

(54) ENGINEERING A HETEROGENEOUS TISSUE FROM PLURIPOTENT STEM CELLS

(71) Applicant: Massachusetts Institute of Technology, Cambridge, MA (US)

(72) Inventors: Patrick Guye, Cambridge, MA (US); Ron Weiss, Newton, MA (US); Mohammad Reza Ebrahimkhani, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 359 days.

(21) Appl. No.: 14/218,426

(22) Filed: Mar. 18, 2014

(65) Prior Publication Data
US 2014/0315753 A1 Oct. 23, 2014

Related U.S. Application Data

(60) Provisional application No. 61/802,931, filed on Mar. 18, 2013.

(51) Int. Cl.
*C12N 5/00* (2006.01)
*C12N 5/02* (2006.01)
*C12N 15/85* (2006.01)
*G01N 33/50* (2006.01)
*C07K 14/47* (2006.01)
*C12N 5/074* (2010.01)

(52) U.S. Cl.
CPC .......... *C12N 15/85* (2013.01); *C07K 14/4705* (2013.01); *C12N 5/0696* (2013.01); *G01N 33/5014* (2013.01); *C12N 2510/00* (2013.01); *C12N 2799/027* (2013.01)

(58) Field of Classification Search
CPC ............................ C12N 15/82; C07K 14/4705
See application file for complete search history.

(56) References Cited

U.S. PATENT DOCUMENTS

| 2008/0057033 | A1 | 3/2008 | Lonai et al. | |
| 2011/0280844 | A1 | 11/2011 | Yu et al. | |
| 2012/0046346 | A1* | 2/2012 | Rossi .................... | C12N 15/111 514/44 R |
| 2012/0301438 | A1 | 11/2012 | Cheng | |

OTHER PUBLICATIONS

Shao, 2010, Expert Opin Biol Ther, 10:231-242).*
Wamaitha, 2015, Genes and Development, 29:1239-1255.*
Takayama, 2011, PLoS One, 6:e21780, pp. 1-9.*
Qu, 2008, Development, Growth and Differentiation, 50:585-593.*
Matsui (2005, Nucleic Acids Research, 33:e43, pp. 1-8).*
Yamanaka, 2008, Cell Stem Cell, 10:678-684.*
Arnold et al., Making a commitment: cell lineage allocation and axis patterning in the early mouse embryo. Nat Rev Mol Cell Biol. Feb. 2009;10(2):91-103. doi: 10.1038/nrm2618. Epub Jan. 8, 2009.
Awuah et al., Role and regulation of PDGFRα signaling in liver development and regeneration. Am J Pathol. May 2013;182(5):1648-58. doi:10.1016/j.ajpath.2013.01.047. Epub Mar. 23, 2013.
Bharti et al., A regulatory loop involving PAX6, MITF, and WNT signaling controls retinal pigment epithelium development. PLoS Genet. Jul. 2012;8(7):e1002757. doi: 10.1371/journal.pgen. 1002757. Epub Jul. 5, 2012.
Blanpain et al., Stem cells assessed. Nat Rev Mol Cell Biol. Jun. 8, 2012;13(7):471-6. doi: 10.1038/nrm3371.
Chen et al., Human fetal hepatic progenitor cells are distinct from, but closely related to, hematopoietic stem/progenitor cells. Stem Cells. Jun. 2013;31(6):1160-9. doi: 10.1002/stem.1359.
Chen et al., Human pluripotent stem cell culture:considerations for maintenance, expansion, and therapeutics. Cell Stem Cell. Jan. 2, 2014;14(1):13-26. doi: 10.1016/j.stem.2013.12.005.
Dianat et al., Human pluripotent stem cells for modelling human liver diseases and cell therapy. Curr Gene Ther. Apr. 2013;13(2):120-32.
Drukker et al., Isolation of primitive endoderm, mesoderm, vascular endothelial and trophoblast progenitors from human pluripotent stem cells. Nat Biotechnol. May 27, 2012;30(6):531-42. doi: 10.1038/nbt.2239.
Eiraku et al., Self-organizing optic-cup morphogenesis in three-dimensional culture. Nature. Apr. 7, 2011;472(7341):51-6. doi: 10.1038/nature09941.
Engle et al., Integrating human pluripotent stem cells into drug development. Cell Stem Cell. Jun. 6, 2013;12(6):669-77. doi:10.1016/j.stem.2013.05.011.
Kameoka et al., A high-throughput screen for teratogens using human pluripotent stem cells. Toxicol Sci. Jan. 2014;137(1):76-90. doi: 10.1093/toxsci/kft239. Epub Oct. 23, 2013.
Kim et al., Generation of human induced pluripotent stem cells by direct delivery of reprogramming proteins. Cell Stem Cell. Jun. 5, 2009;4(6):472-6. doi: 10.1016/j.stem.2009.05.005. Epub May 28, 2009.
Kwon et al., The endoderm of the mouse embryo arises by dynamic widespread intercalation of embryonic and extraembryonic lineages. Dev Cell. Oct. 2008;15(4):509-20. doi: 10.1016/j.devcel. 2008.07.017.
Lancaster et al., Cerebral organoids model human brain development and microcephaly. Nature. Sep. 19, 2013;501(7467):373-9. doi:10.1038/nature12517. Epub Aug. 28, 2013.
Ludwig et al., Derivation of human embryonic stem cells in defined conditions. Nat Biotechnol. Feb. 2006;24(2):185-7. Epub Jan. 1, 2006.
Medine et al., Developing high-fidelity hepatotoxicity models from pluripotent stem cells. Stem Cells Transl Med. Jul. 2013;2(7):505-9. doi: 10.5966/sctm.2012-0138. Epub Jun. 11, 2013.
Niakan et al., Analysis of human embryos from zygote to blastocyst reveals distinct gene expression patterns relative to the mouse. Dev Biol. Mar. 1, 2013;375(1):54-64. doi: 10.1016/j.ydbio.2012.12.008. Epub Dec. 19, 2012

(Continued)

*Primary Examiner* — Valarie Bertoglio
(74) *Attorney, Agent, or Firm* — Wolf, Greenfield & Sacks, P.C.

(57) ABSTRACT

Aspects of the present disclosure are directed to methods and compositions for the production of heterogeneous tissue from human induced pluripotent stem (hiPS) cells.

12 Claims, 50 Drawing Sheets

(56) References Cited

OTHER PUBLICATIONS

Niederreither et al., Retinoic acid in development: towards an integrated view. Nat Rev Genet. Jul. 2008;9(7):541-53. doi: 10.1038/nrg2340. Epub Jun. 10, 2008.
Park et al., Generation of human-induced pluripotent stem cells. Nat Protoc. 2008;3(7):1180-6. doi: 10.1038/nprot.2008.92.
Peterkin et al., GATA-6 maintains BMP-4 and Nkx2 expression during cardiomyocyte precursor maturation. EMBO J. Aug. 15, 2003;22(16):4260-73.
Pinho et al., PDGFRα and CD51 mark human nestin+ sphere-forming mesenchymal stem cells capable of hematopoietic progenitor cell expansion. J Exp Med. Jul. 1, 2013;210(7):1351-67. doi: 10.1084/jem.20122252. Epub Jun. 17, 2013.
Rashid et al., Modeling inherited metabolic disorders of the liver using human induced pluripotent stem cells. J Clin Invest. Sep. 2010;120(9):3127-36. doi:10.1172/JCI43122. Epub Aug. 25, 2010.
Robinton et al., The promise of induced pluripotent stem cells in research and therapy. Nature. Jan. 18, 2012;481(7381):295-305. doi: 10.1038/nature10761.
Rong et al., GATA-6 promotes cell survival by up-regulating BMP-2 expression during embryonic stem cell differentiation. Mol Biol Cell. Sep. 2012;23(18):3754-63. doi: 10.1091/mbc.E12-04-0313. Epub Aug. 1, 2012.
Slukvin, Hematopoietic specification from human pluripotent stem cells:current advances and challenges toward de novo generation of hematopoietic stem cells. Blood. Dec. 12, 2013;122(25):4035-46. doi: 10.1182/blood-2013-07-474825. Epub Oct. 11, 2013.
Sugiyama et al., Hepatoblasts comprise a niche for fetal liver erythropoiesis through cytokine production. Biochem Biophys Res Commun Jul. 1, 2011;410(2):301-6. doi: 10.1016/j.bbrc.2011.05.137. Epub May 30, 2011.
Tabar et al., Pluripotent stem cells in regenerative medicine: challenges and recent progress. Nat Rev Genet. Feb. 2014;15(2):82-92. doi: 10.1038/nrg3563.
Takebe et al., Vascularized and functional human liver from an iPSC-derived organ bud transplant. Nature. Jul. 25, 2013;499(7459):481-4. doi: 10.1038/nature12271. Epub Jul. 3, 2013.
Tanaka et al., Mouse hepatoblasts at distinct developmental stages are characterized by expression of EpCAM and DLK1: drastic change of EpCAM expression during liver development. Mech Dev. Aug.-Sep. 2009;126(8-9):665-76. doi: 10.1016/j.mod.2009.06.939. Epub Jun. 13, 2009.
Wu et al., The expression of CXCR4/CXCL12 in first-trimester human trophoblast cells. Biol Reprod. Jun. 2004;70(6):1877-85. Epub Feb. 18, 2004.
Yamanaka, Induction of pluripotent stem cells from mouse fibroblasts by four transcription factors. Cell Prolif. Feb. 2008;41 Suppl 1:51-6 doi:10.1111/j.1365-2184.2008.00493.x.
Yoshioka et al., Efficient generation of human iPSCs by a synthetic self-replicative RNA. Cell Stem Cell. Aug. 1, 2013;13(2):246-54. doi:10.1016/j.stem.2013.06.001.
Yu et al., Induced pluripotent stem cell lines derived from human somatic cells. Science. Dec. 21, 2007;318(5858):1917-20. Epub Nov. 20, 2007.
Zhao et al., GATA6 is essential for embryonic development of the liver but dispensable for early heart formation. Mol Cell Biol. Apr. 2005;25(7):2622-31.

* cited by examiner

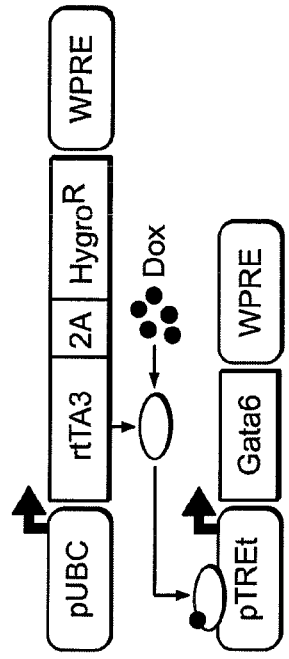
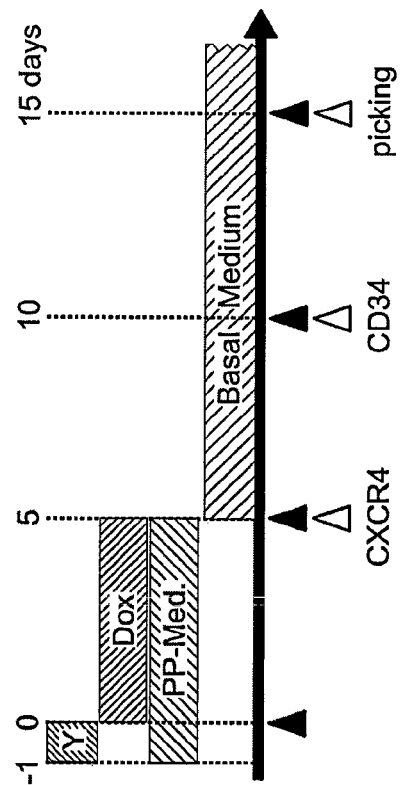
FIG. 1B
FIG. 1A

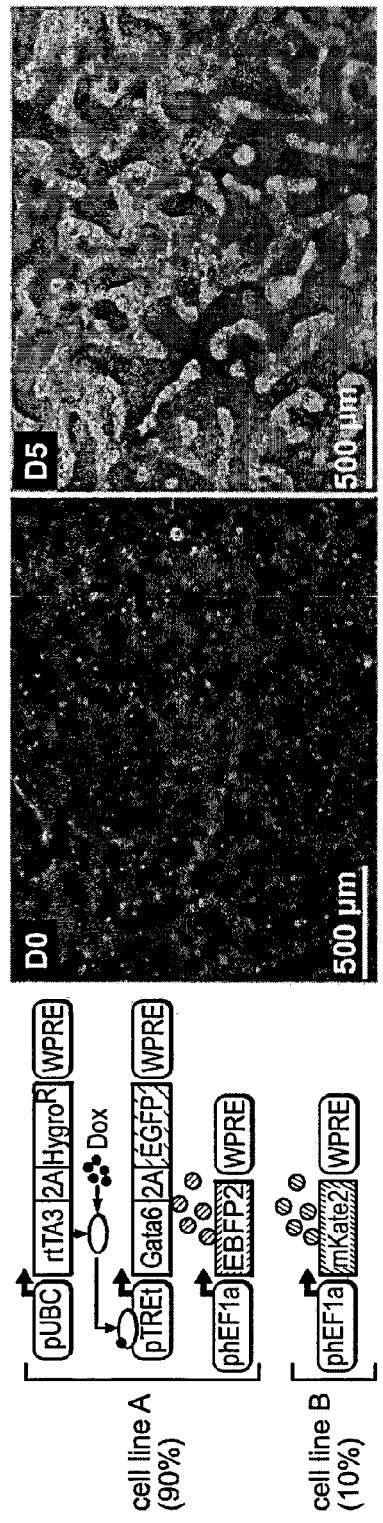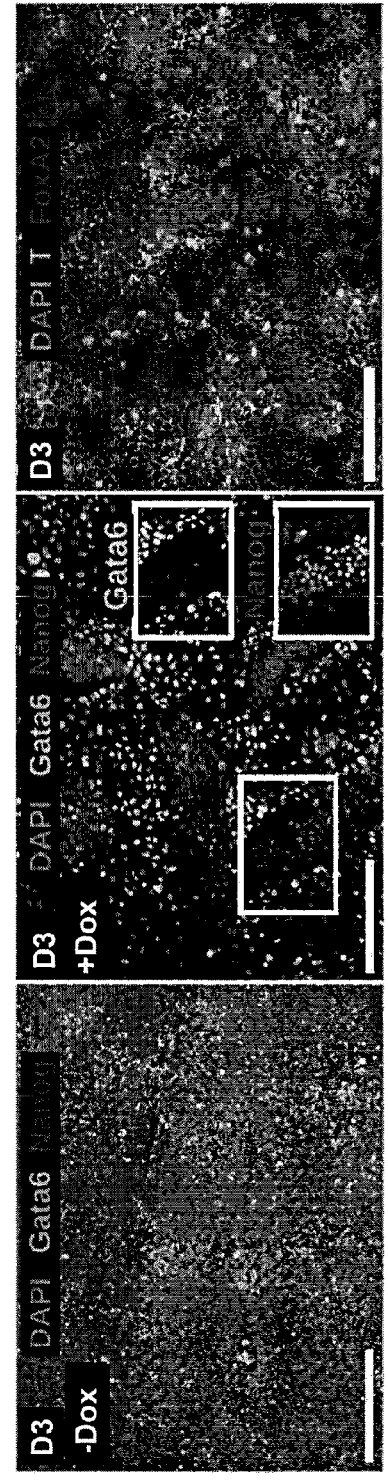

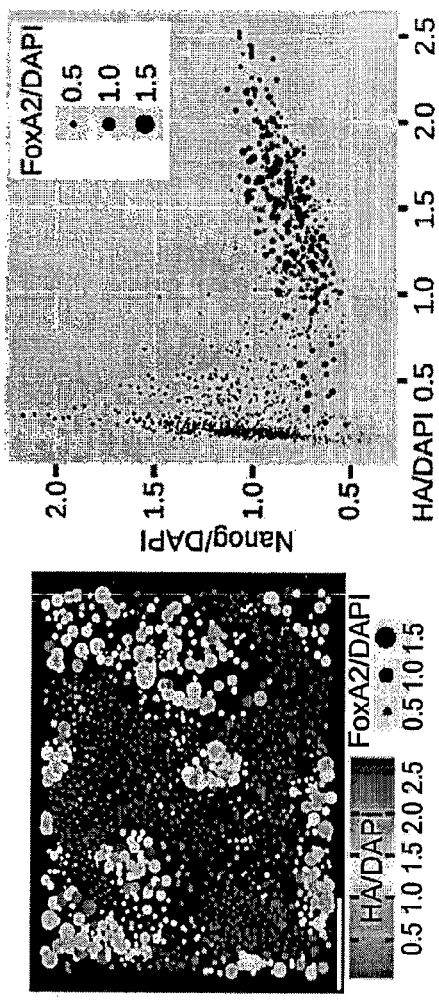
FIG. 2C
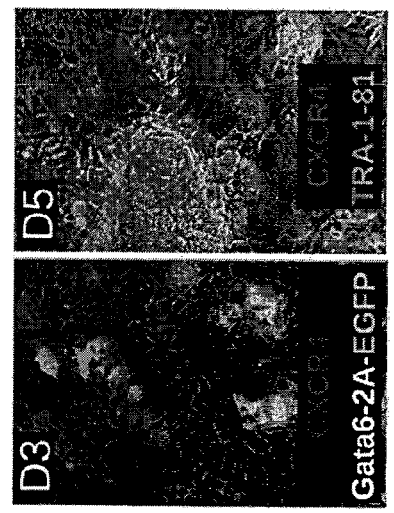
FIG. 2D

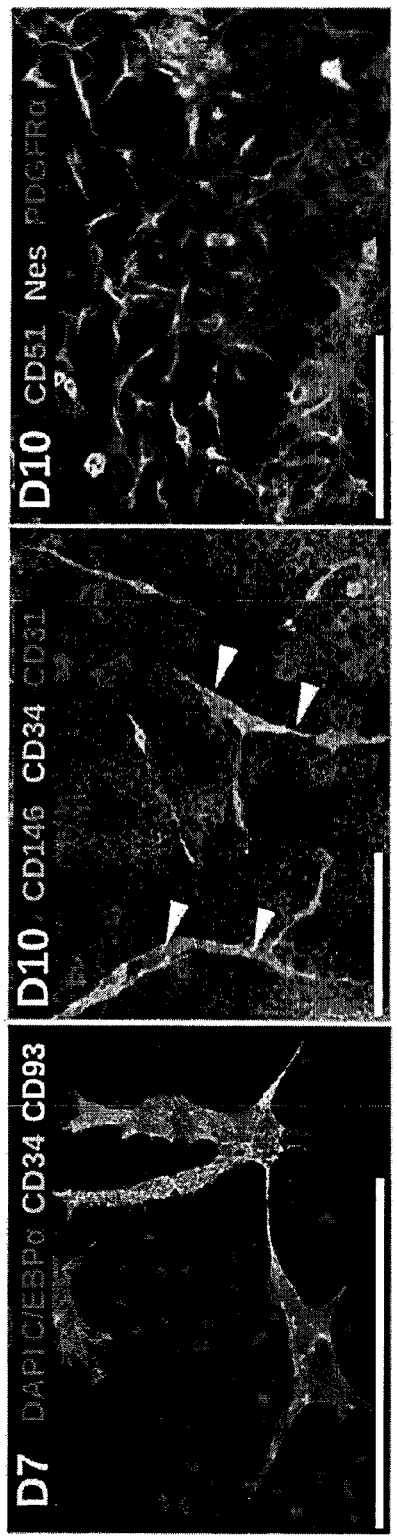
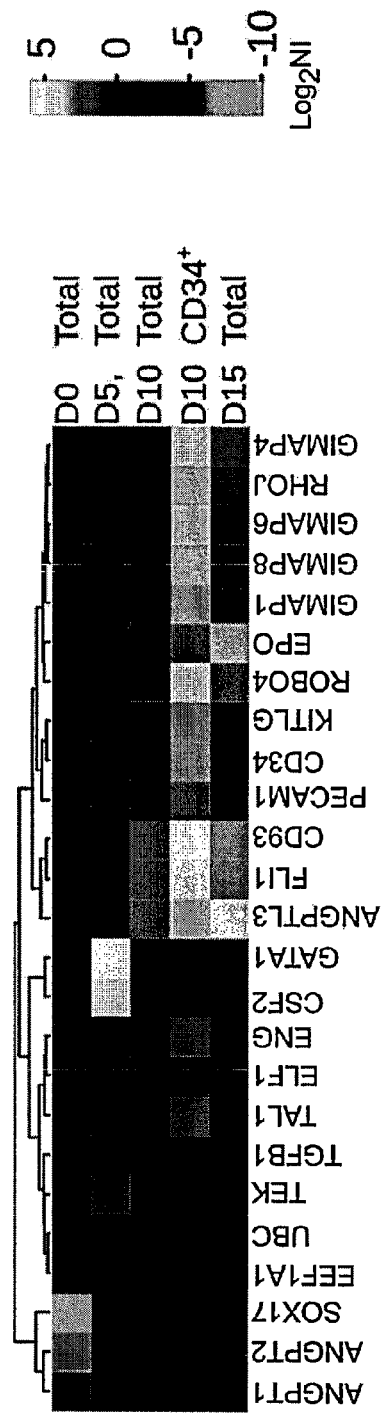
FIG. 3A

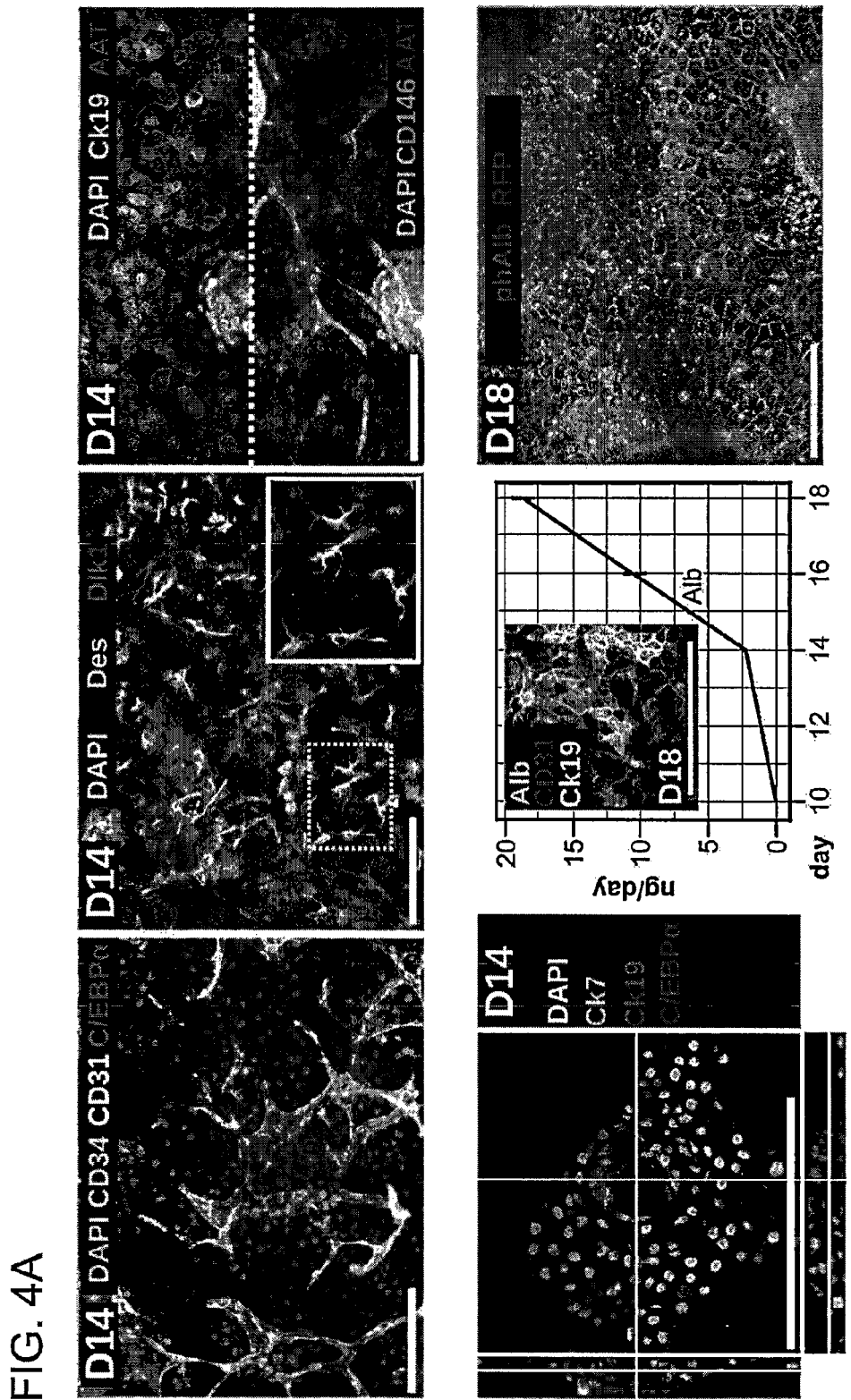

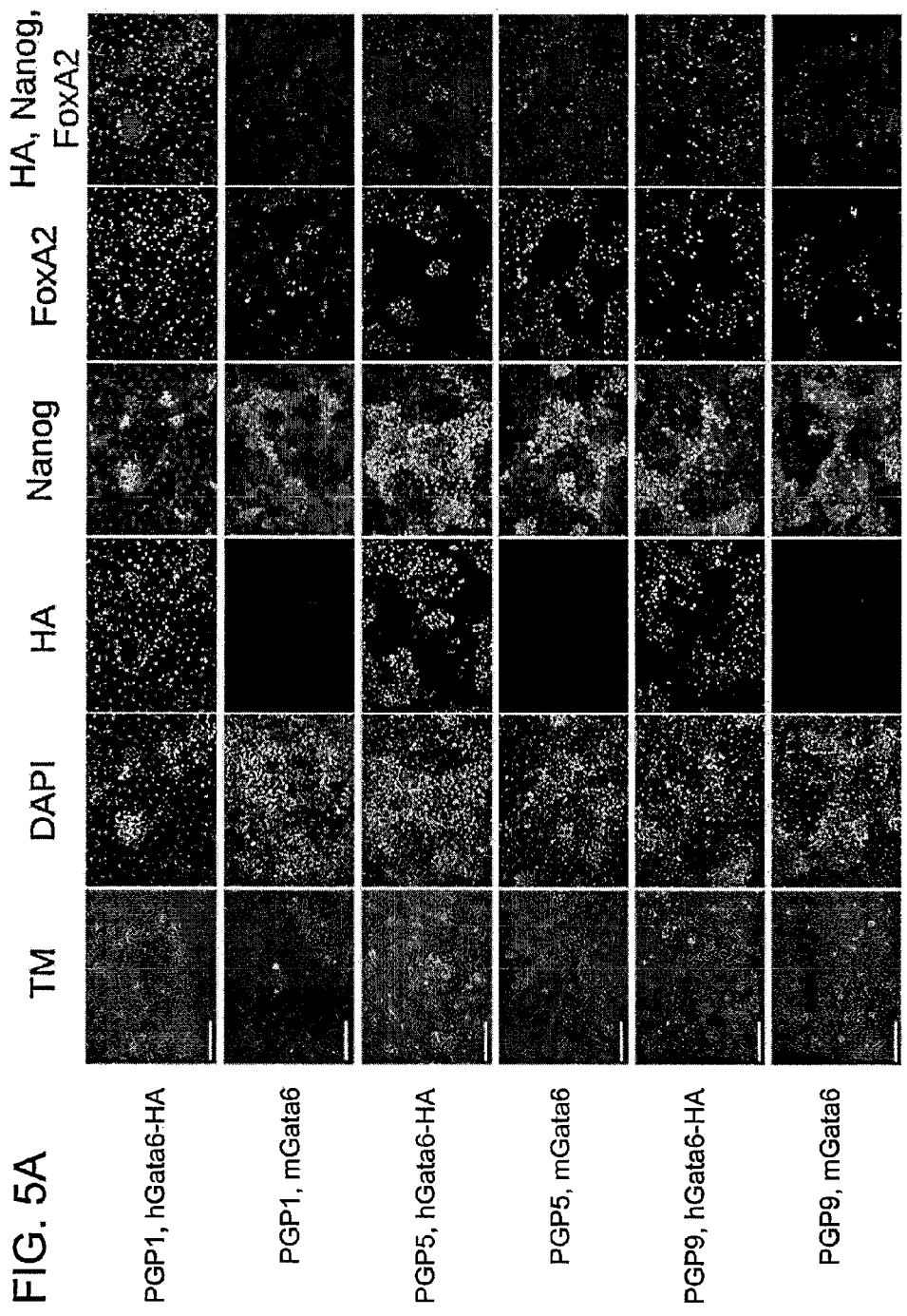

PGP5, mGata6

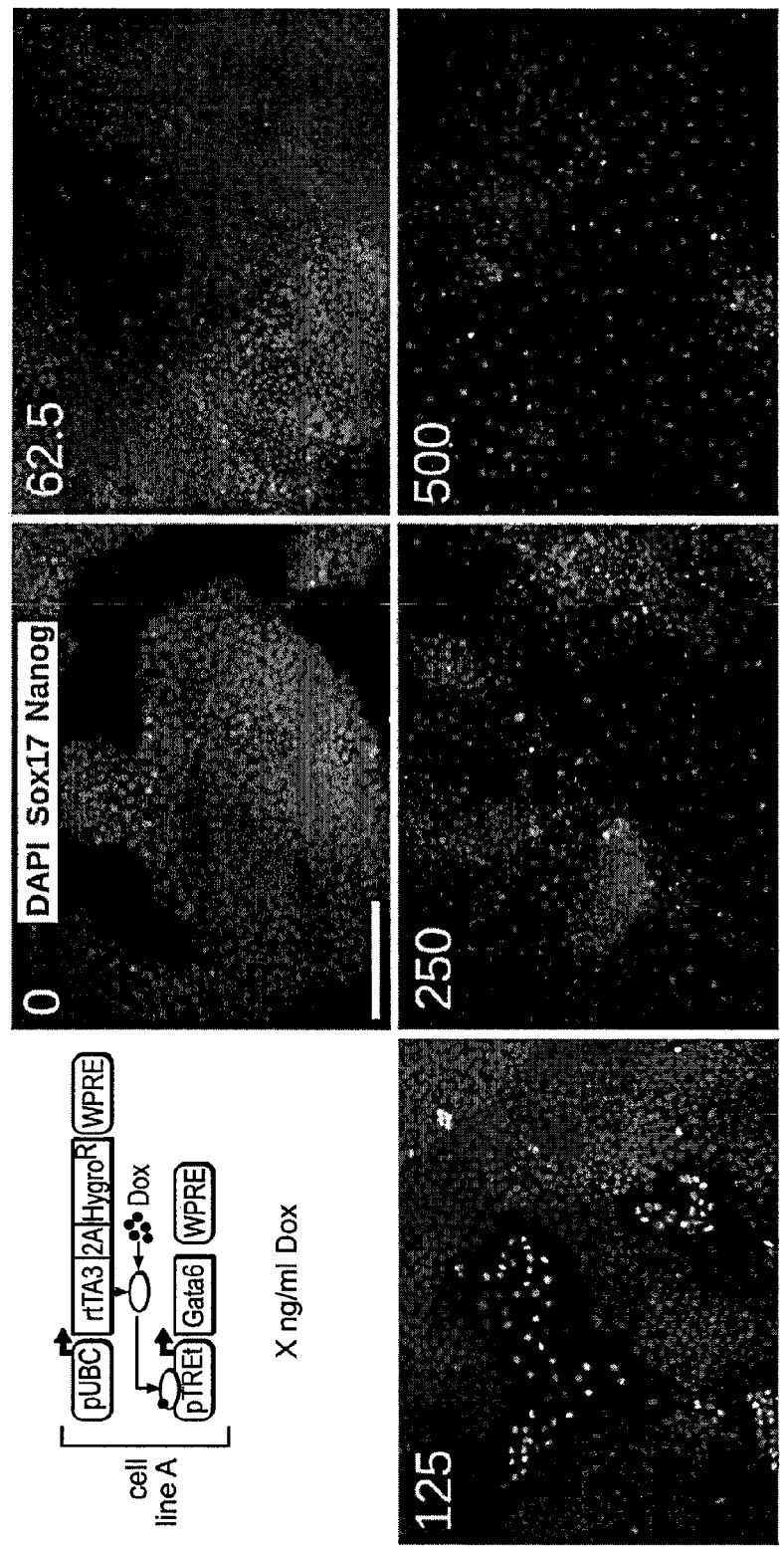

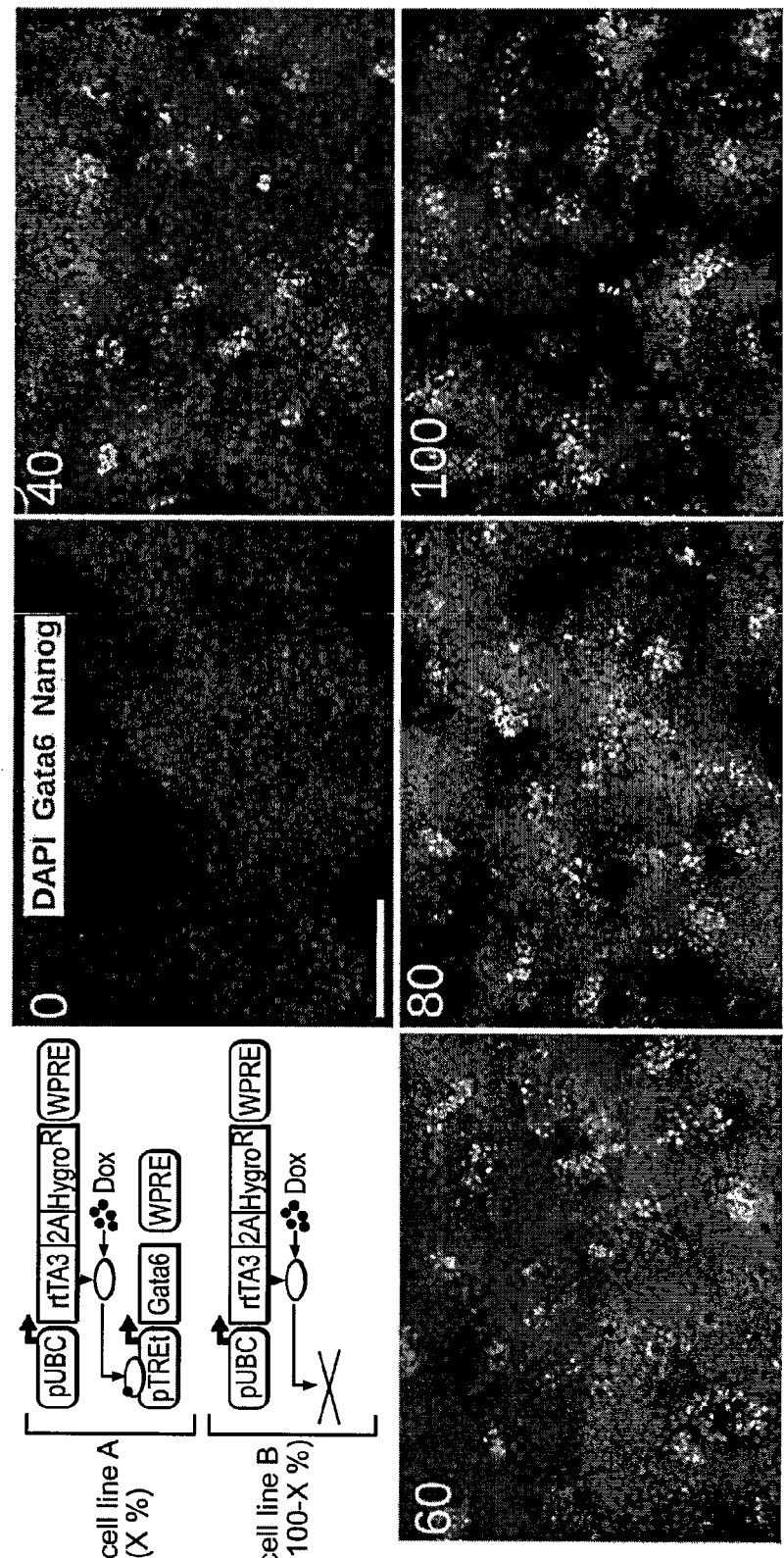

FIG. 7C
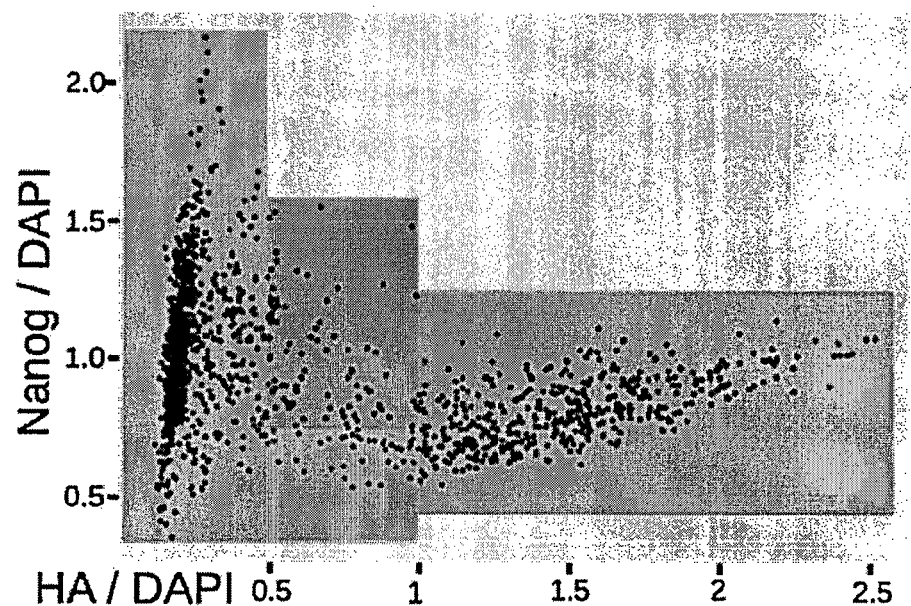
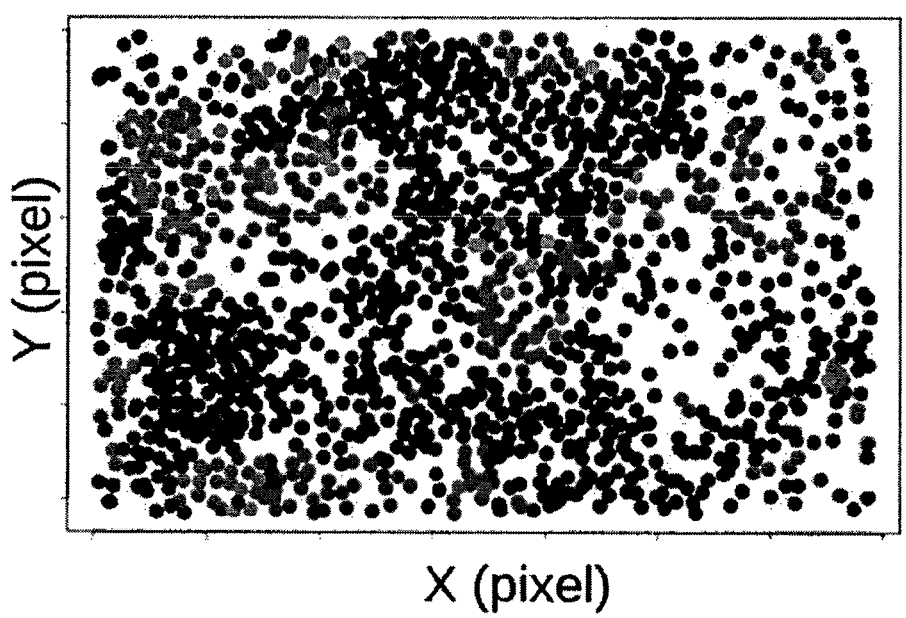

FIG. 8B
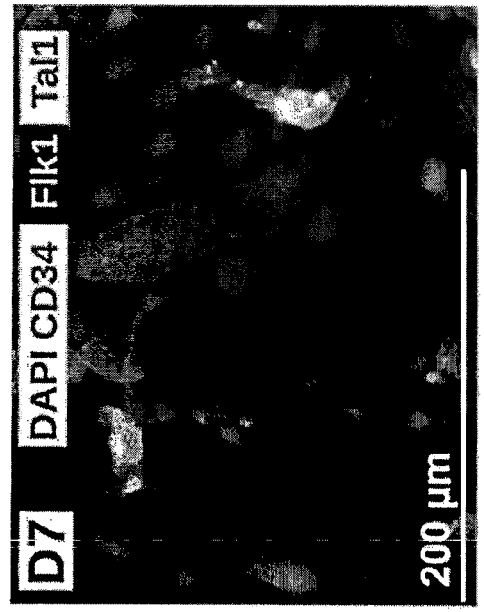
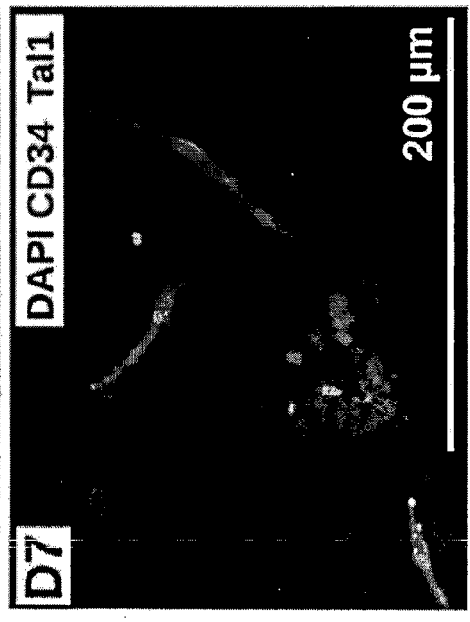
FIG. 8A
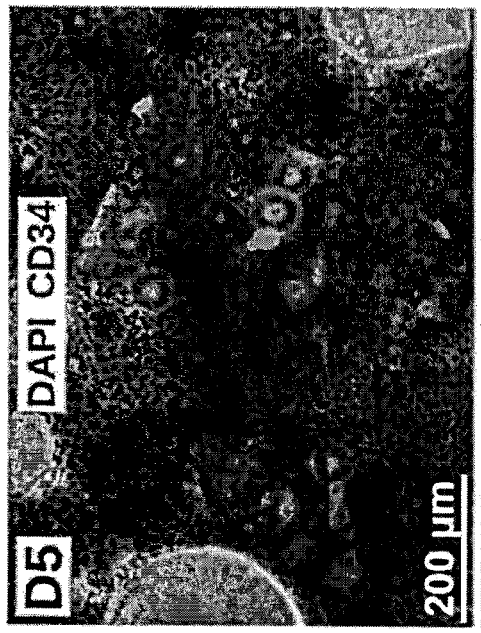
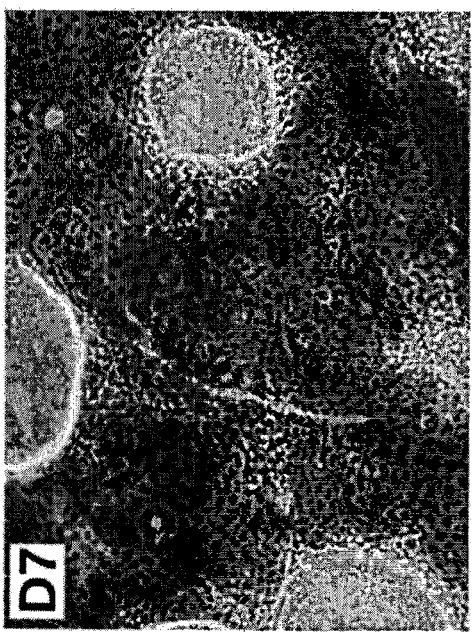

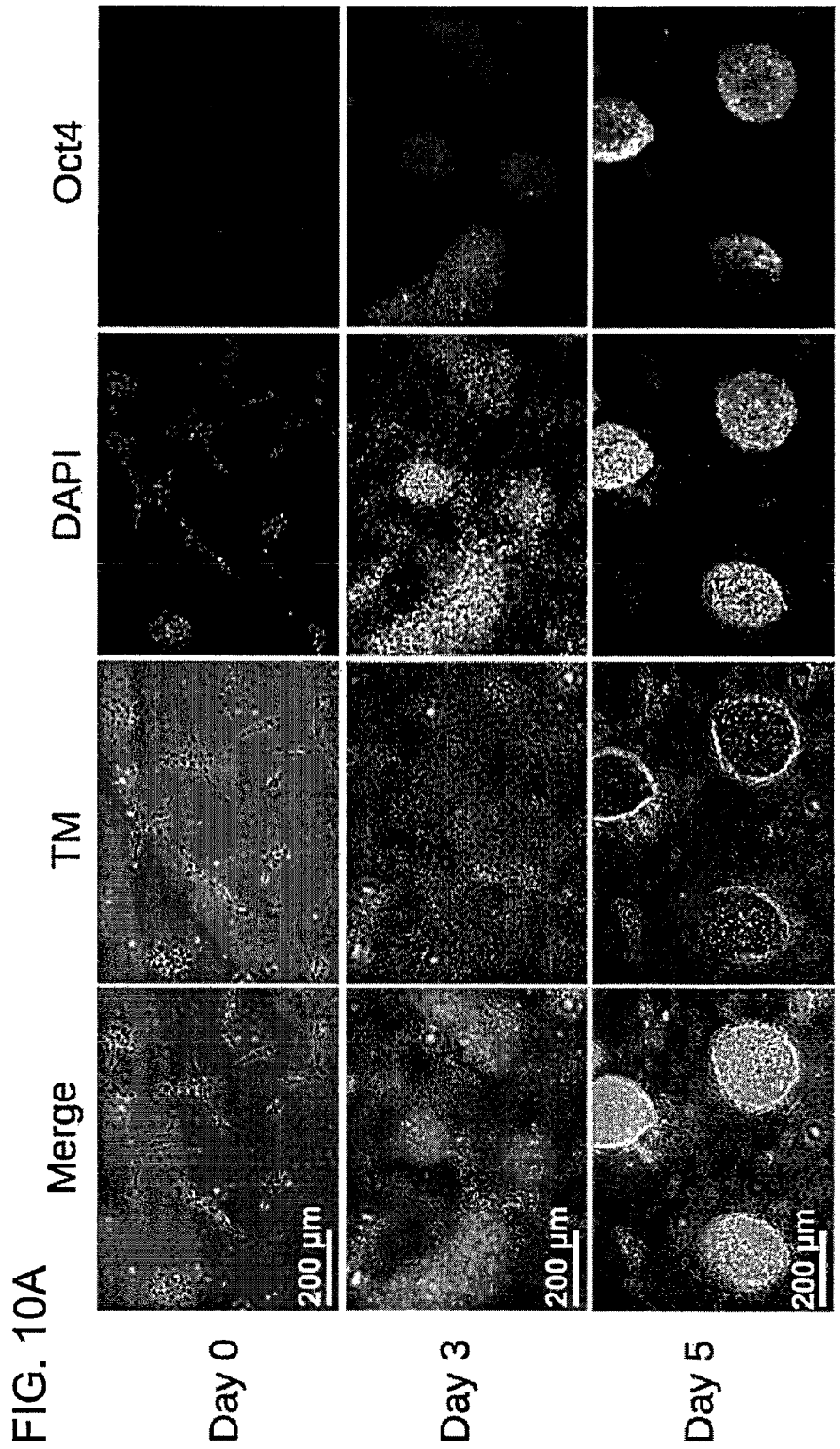

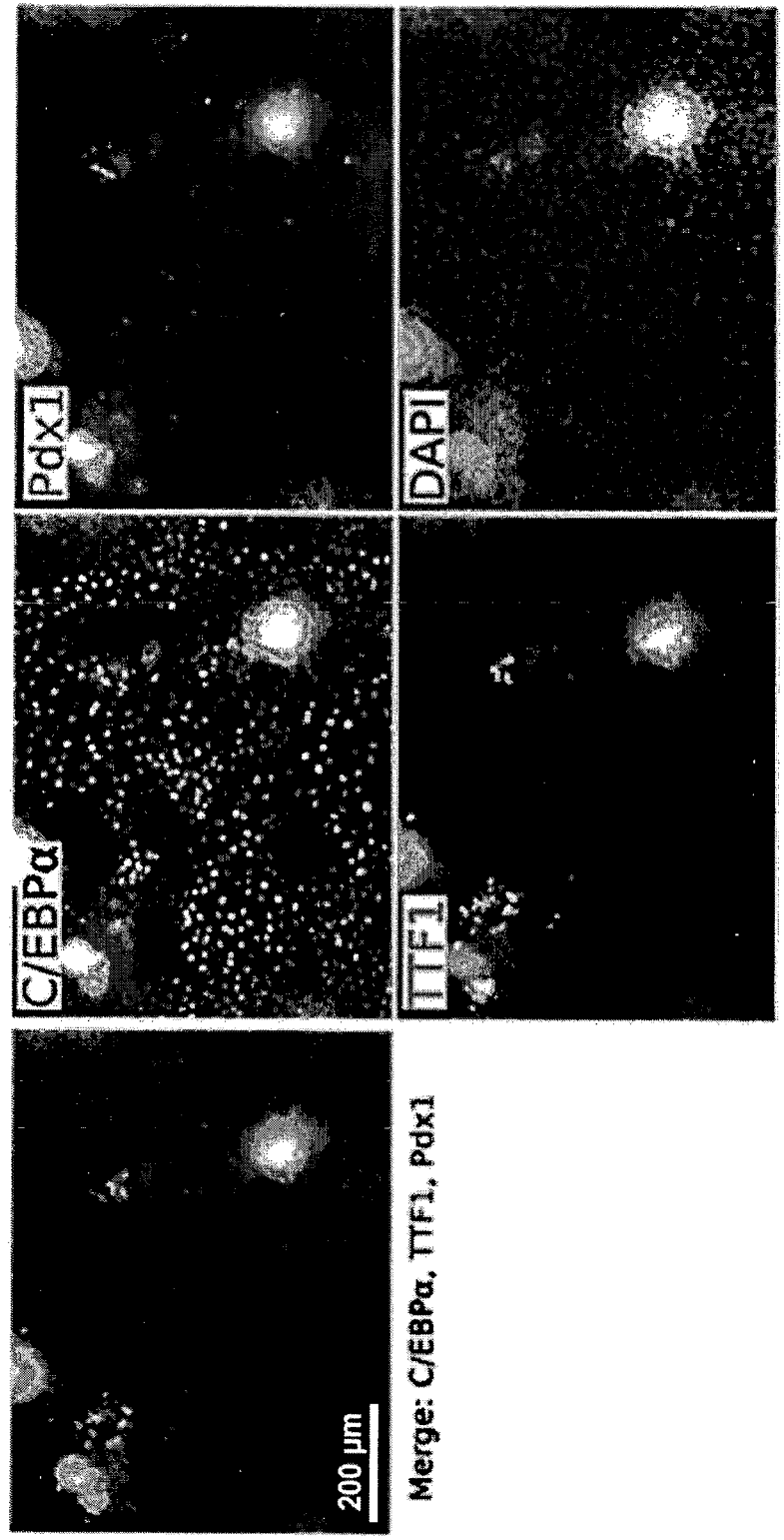

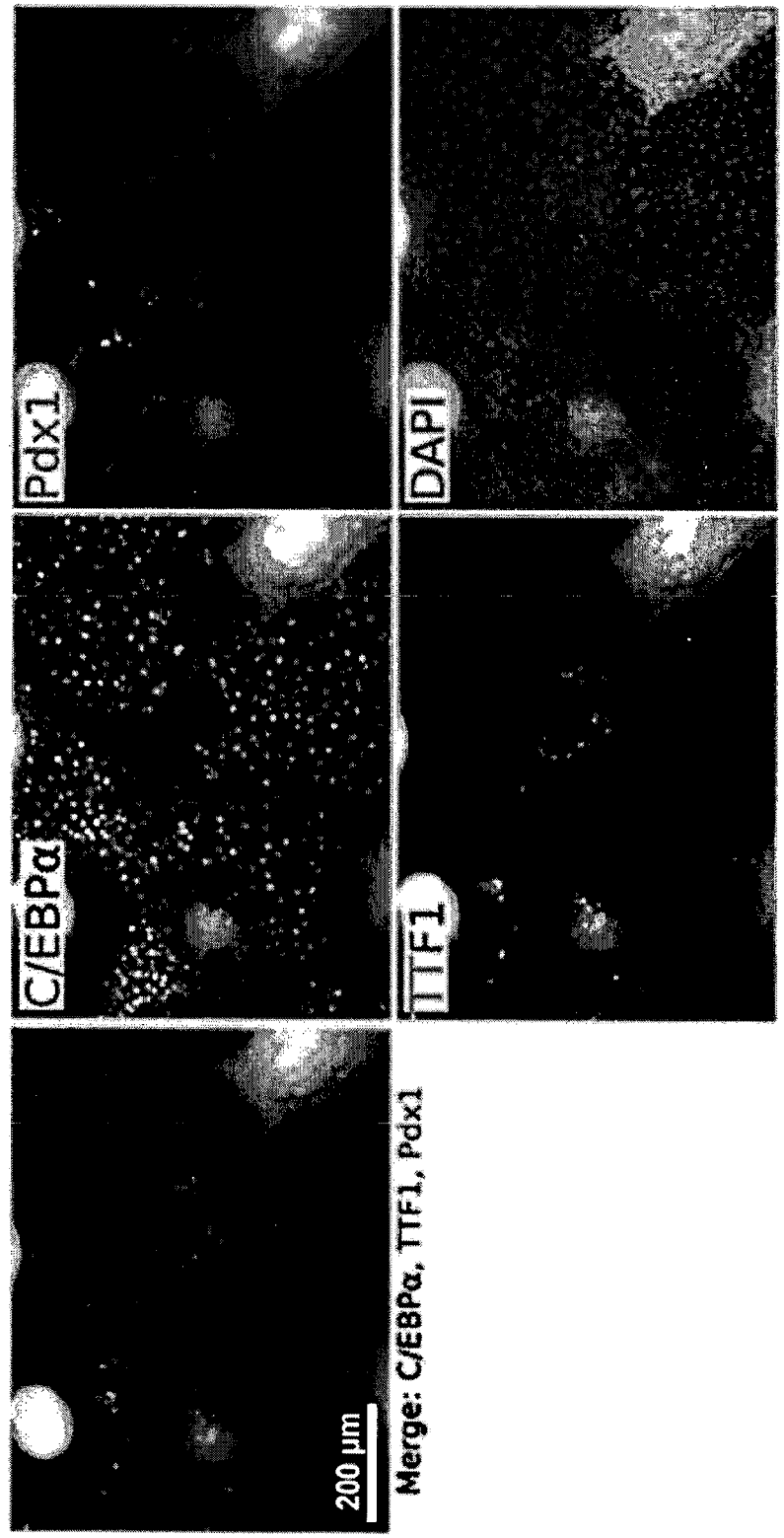

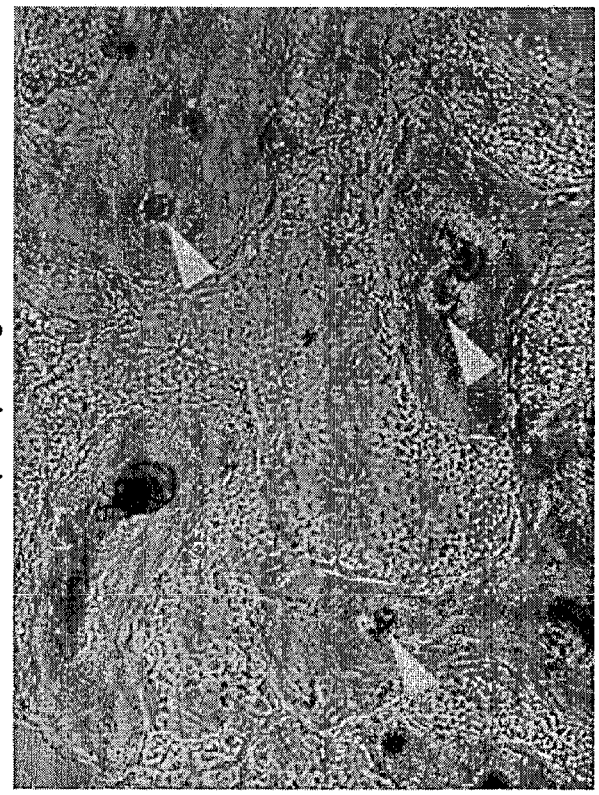
FIG. 13A

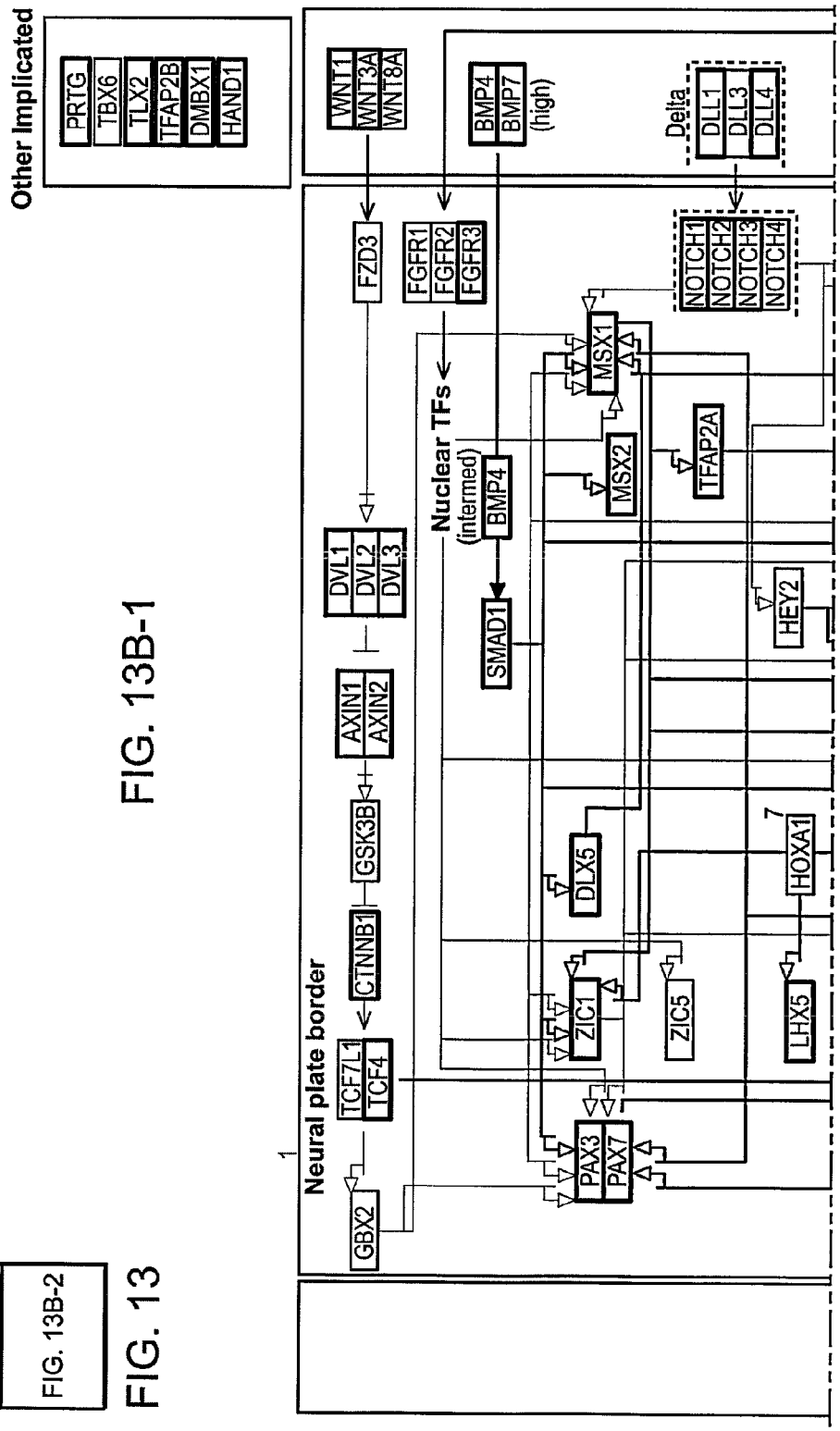

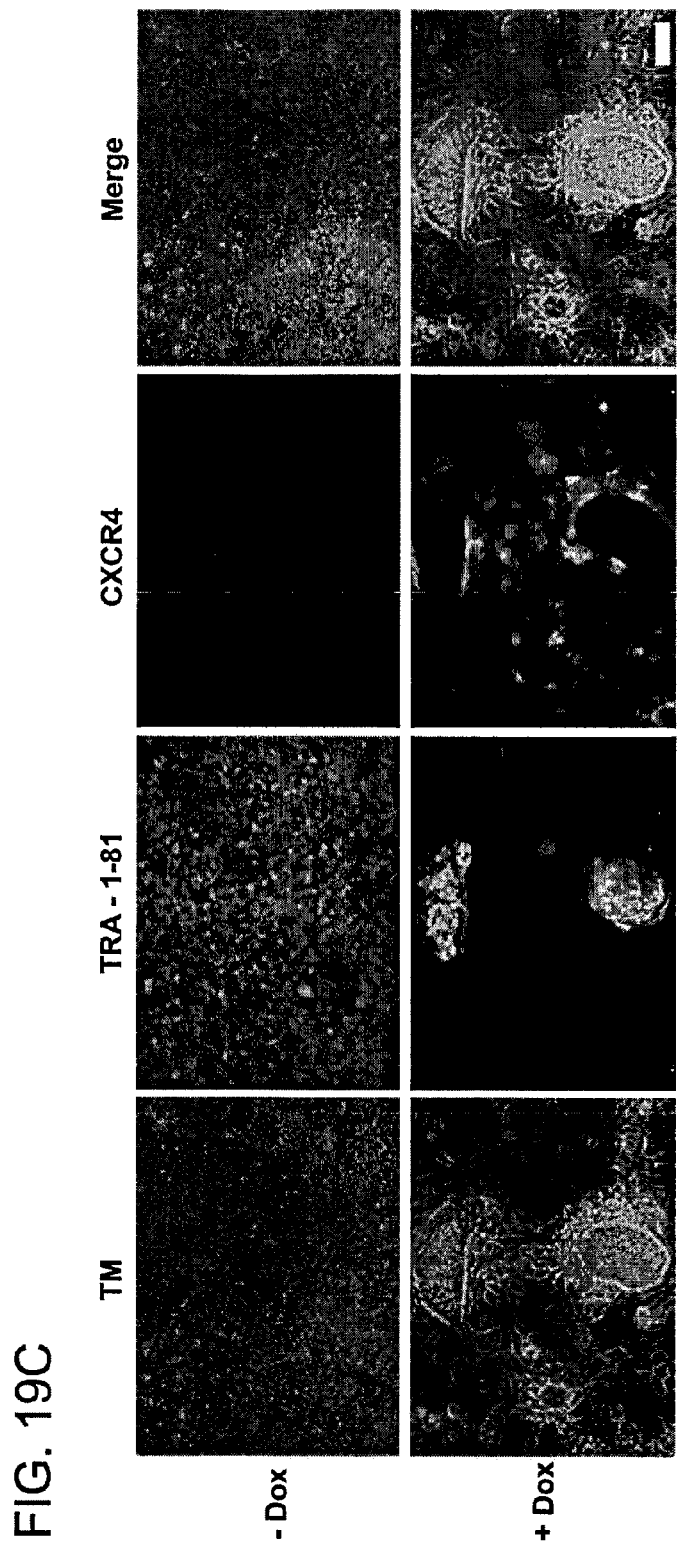

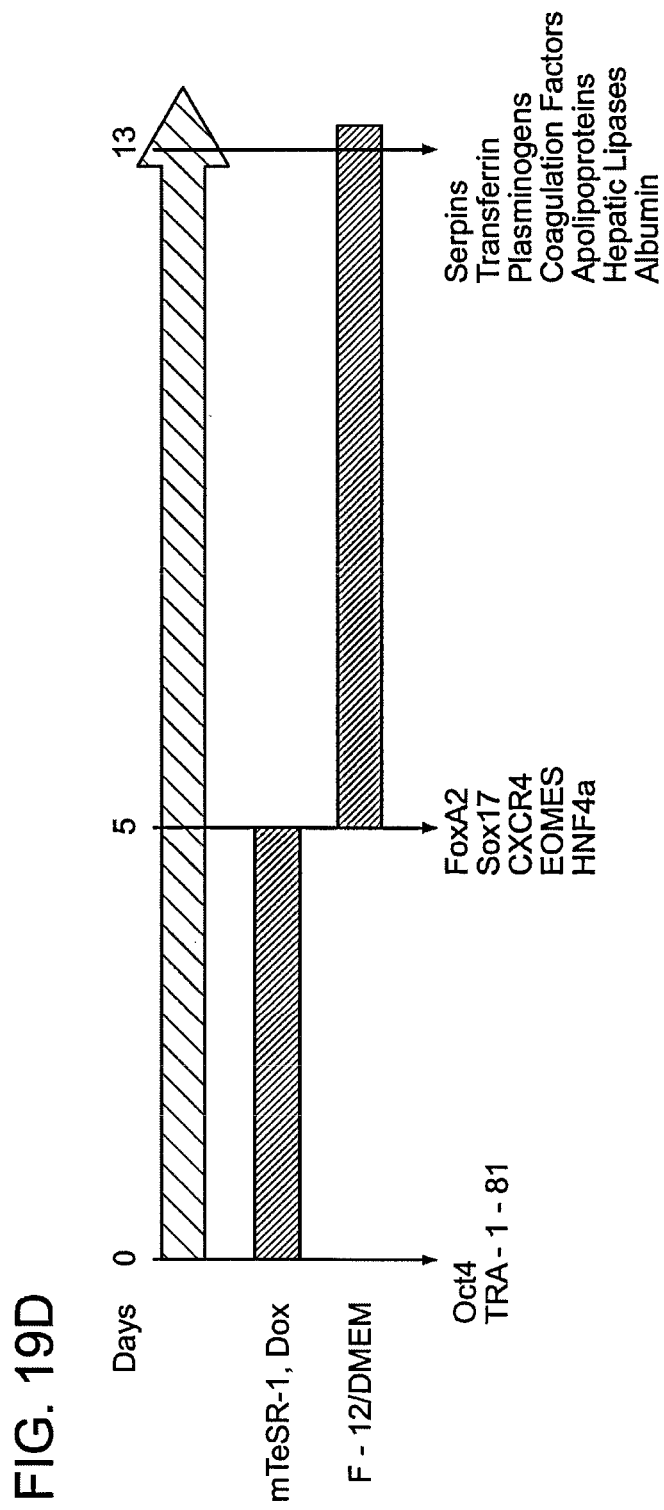

`US 9,677,085 B2`

ENGINEERING A HETEROGENEOUS TISSUE FROM PLURIPOTENT STEM CELLS

RELATED APPLICATIONS

This application claims the benefit under 35 U.S.C. §119 (e) of U.S. provisional application No. 61/802,931, filed Mar. 18, 2013, which is incorporated by reference herein in its entirety.

FEDERALLY SPONSORED RESEARCH

This invention was made with government support under Grant No.s R01 CA155320 awarded by the National Institutes of Health. The government has certain rights in the invention.

FIELD OF THE INVENTION

Aspects of the present disclosure are in the field of stem cell technology.

BACKGROUND OF THE INVENTION

Human induced pluripotent stem (hiPS) cells have tremendous potential for personalized and regenerative medicine[1], possibly addressing the critical shortage of donor organs and tissues that exists for a variety of diseases. While the generation of hiPS cells became a routine process in recent years[2], current methods of taking advantage of these promising cells focus mostly on deriving a homogenous population of specialized cells and have had modest success for producing stable or complex tissues[3].

SUMMARY OF THE INVENTION

The present disclosure provides, inter alia, methods and compositions for generating and co-differentiating human induced pluripotent stem (hiPS) cell-derived progenitor cells with minimal guidance or external interference, resulting in complex, organ-like tissues. In the course of embryonic and fetal development, tissues and organs do not develop as homogenous populations or by merging populations of differentiated cells. Rather, tissues and organs emerge as the product of a heterogeneous environment where complex interactions among progenitor cells guide developmental processes in a self-contained and step-wise fashion[4]. Surprisingly, as described herein, a symmetry break was introduced in hiPS cells by engineering in the cells a pulse of expression a single transcription factor (e.g., GATA6). A "symmetry break" refers to a switch from a homogeneous cell population (e.g., all pluripotent cells) to a heterogeneous cell population (e.g., a mixture of endodermal cells, ectodermal cells and mesodermal cells). This break in symmetry initiated a gastrulation-like event and a rapid emergence and co-differentiation of all three germ layers (i.e., ectoderm, mesoderm, endoderm). Within two weeks of the symmetry break, an organized, heterogeneous tissue developed under standard cell culture conditions, the heterogeneous tissue containing a mixture of cells types, including, for example, mesenchymal stem cells, hepatoblasts, cholangiocytes, angiogenic endothelium, endothelial cells, stellate cells and definitive hematopoietic progenitors as well as spatially separated anterior neural folds developing.

This approach demonstrates a new, powerful way of unlocking the potential of hiPS cells by engineering control at a single cell level from within the cell and embracing heterogeneity as well as emergence to recapitulate embryonic morphogenetic processes, thereby producing complex homeostatic (e.g., self-regulatory, self-replenishing) tissues.

Aspects of the present disclosure provide methods that comprise culturing in cell culture media human induced pluripotent stem (hiPS) cells modified to overexpress a gene encoding GATA6 protein.

In some embodiments, hiPS cells of the present disclosure overexpress a gene encoding GATA6 protein at levels sufficient to produce mesodermal cells, endodermal cells, ectodermal cells, or any combination thereof. In some embodiments, hiPS cells are cultured for a time sufficient to produce pluripotent cells, mesodermal cells, endodermal cells, ectodermal cells, or any combination thereof.

In some embodiments, hiPS cells of the present disclosure overexpress the gene encoding GATA6 protein at levels sufficient to produce heterogeneous tissue. In some embodiments, hiPS cells are cultured for a time sufficient to produce heterogeneous tissue. In some embodiments, hiPS cells are cultured for at least 7 to 15 days.

In some embodiments, heterogeneous tissue produced from hiPS cells that overexpress a gene encoding GATA6 protein comprises hepatic endodermal cells, hepatoblast-like cells, cholangiocyte-like cells, endothelial progenitor cells, endothelial-like cells, hemogenic endothelial cells, erythrocyte-like cells, hematopoietic progenitor-like cells, mesenchymal progenitor cells, stellate-like cells, neurectodermal cells, neural plate-like cells, neural fold-like cells, or any combination thereof.

In some embodiments, cells of heterogeneous tissue of the present disclosure are FOXA2$^+$ and/or SOX17$^+$.

In some embodiments, cells of heterogeneous tissue of the present disclosure are CEBPA$^+$, HNF4A$^+$, FOXA2$^+$ and/or HHEX$^+$.

In some embodiments, cells of heterogeneous tissue of the present disclosure are CD133$^+$, AAT$^+$, CEBPA$^+$, FOXA2$^+$, AFP$^+$, LGR5$^+$, CK19$^+$, DLK1$^+$ and/or ALB$^+$.

In some embodiments, cells of heterogeneous tissue of the present disclosure are CK7$^+$ and/or AQP1$^+$.

In some embodiments, cells of heterogeneous tissue of the present disclosure are Brachyury$^+$ (T$^+$).

In some embodiments, cells of heterogeneous tissue of the present disclosure are CD51$^+$, NES$^+$ and/or PDGFRA$^+$.

In some embodiments, cells of heterogeneous tissue of the present disclosure are CD34$^+$ and/or CEBPA$^-$.

In some embodiments, cells of heterogeneous tissue of the present disclosure are NES$^+$ and/or PDGFRA$^+$.

In some embodiments, cells of heterogeneous tissue of the present disclosure are DES$^+$.

In some embodiments, cells of heterogeneous tissue of the present disclosure are CD31$^+$.

In some embodiments, cells of heterogeneous tissue of the present disclosure are CD34$^+$, TAL1$^+$, FLK1$^+$ and/or CD93$^+$.

In some embodiments, cells of heterogeneous tissue of the present disclosure are hemoglobin$^+$.

In some embodiments, cells of heterogeneous tissue of the present disclosure are CD45$^+$.

In some embodiments, cells of heterogeneous tissue of the present disclosure are OCT4$^+$, SOX10$^+$ and/or NES$^+$.

In some embodiments, cells of heterogeneous tissue of the present disclosure are OCT4$^+$, SOX10$^+$ and/or AP2A$^+$.

In some embodiments, cells of heterogeneous tissue of the present disclosure are OCT4$^-$, SOX10$^+$ and/or AP2A$^-$.

In some embodiments, cells of heterogeneous tissue of the present disclosure are PAX7$^+$, DLX5$^+$, FOXG1$^+$ and/or PAX6$^+$.

In some embodiments, cells of heterogeneous tissue of the present disclosure secrete albumin.

In some embodiments, hiPS cells of the present disclosure are modified to stably express a gene encoding GATA6 protein. Human iPS cells, in some embodiments, comprise a nucleic acid that comprises a promoter operably linked to a gene encoding GATA6 protein. A promoter may be, for example, an inducible promoter.

Some aspects of the present disclosure provide human induced pluripotent stem (hiPS) cells modified to overexpress a gene encoding GATA6 protein. In some embodiments, a cell comprises a nucleic acid that comprises a promoter operably linked to a gene encoding GATA6 protein. In some embodiments, a promoter is an inducible promoter. In some embodiments, a nucleic acid is a lentiviral vector.

Some aspects of the present disclosure provide methods that comprise overexpressing a gene encoding GATA6 protein in human induced pluripotent stem (hiPS) cells. In some embodiments, methods comprise transfecting hiPS cells with a nucleic acid that comprises a promoter operably linked to a gene encoding GATA6 protein. In some embodiments, a promoter is an inducible promoter. In some embodiments, a nucleic acid is a lentiviral vector.

In some embodiments, methods comprise (a) transfecting hiPS cells with a nucleic acid that constitutively expresses a doxycycline-activatable transactivator (rtTA), (b) transfecting hiPS cells with a nucleic acid encoding a promoter operably linked to the gene encoding GATA6 protein, wherein the promoter comprises a binding site for rtTA, and (c) culturing hiPS cells in the presence of doxycycline, thereby activating expression of GATA6 protein.

Some aspects of the present disclosure provide methods that comprise (a) isolating somatic cells from a human, (b) inducing pluripotency in isolated somatic cells of (a), thereby producing human induced pluripotent stem (hiPS) cells, (c) overexpressing in hiPS cells of (b) a gene encoding GATA6 protein at a level sufficient to produce heterogeneous tissue, and (d) culturing hiPS cells of (c) for a time sufficient to produce heterogeneous tissue that comprises cells selected from hepatic endodermal cells, hepatoblast-like cells, cholangiocyte-like cells, endothelial progenitor cells, endothelial-like cells, hemogenic endothelial cells, erythrocyte-like cells, hematopoietic progenitor-like cells, mesenchymal progenitor cells, stellate-like cells, neurectodermal cells, neural plate-like cells, neural fold-like cells, and any combination thereof. In some embodiments, methods further comprise banking heterogeneous tissue produced from hiPS cells that overexpress a gene encoding GATA6 protein. In some embodiments, methods further comprise transplanting heterogeneous tissue produced from hiPS cells that overexpress a gene encoding GATA6 protein into a subject (e.g., a human subject, such as the human from whom somatic cells were isolated).

In some embodiments, methods further comprise isolating from heterogeneous tissue cells selected from hepatic endodermal cells, hepatoblast-like cells, cholangiocyte-like cells, endothelial progenitor cells, endothelial-like cells, hemogenic endothelial cells, erythrocyte-like cells, hematopoietic progenitor-like cells, mesenchymal progenitor cells, stellate-like cells, neurectodermal cells, neural plate-like cells, neural fold-like cells, and any combination thereof, thereby producing isolated cells. In some embodiments, methods further comprise banking isolated cells. In some embodiments, methods further comprise transplanting isolated cells into subject (e.g., a human subject, such as the human from whom somatic cells were isolated).

Aspects of the present disclosure provide methods that comprise culturing in cell culture media human induced pluripotent stem (hiPS) cells modified to overexpress a gene encoding GATA4 protein.

In some embodiments, hiPS cells overexpress a gene encoding GATA4 protein at levels sufficient to produce mesodermal cells, endodermal cells, ectodermal cells, or any combination thereof. In some embodiments, hiPS cells are cultured for a time sufficient to produce pluripotent cells, mesodermal cells, endodermal cells, ectodermal cells, or any combination thereof.

In some embodiments, hiPS cells overexpress a gene encoding GATA4 protein at levels sufficient to produce heterogeneous tissue. In some embodiments, hiPS cells are cultured for a time sufficient to produce heterogeneous tissue. In some embodiments, hiPS cells are cultured for at least 7 to 15 days.

In some embodiments, heterogeneous tissue produced from hiPS cells that overexpress a gene encoding GATA4 protein comprises hepatic endodermal cells, hepatoblast-like cells, cholangiocyte-like cells, endothelial progenitor cells, endothelial-like cells, hemogenic endothelial cells, erythrocyte-like cells, hematopoietic progenitor-like cells, mesenchymal progenitor cells, stellate-like cells, neurectodermal cells, neural plate-like cells, neural fold-like cells, or any combination thereof.

Some aspects of the present disclosure provide human induced pluripotent stem (hiPS) cells modified to overexpress a gene encoding GATA4 protein.

Some aspects of the present disclosure provide methods that comprise overexpressing a gene encoding GATA4 protein in a human induced pluripotent stem (hiPS) cell.

In some embodiments, hiPS cells are modified to stably express a gene encoding GATA4 protein. hiPS cells, in some embodiments, comprise a nucleic acid that comprises a promoter operably linked to a gene encoding GATA4 protein. A promoter may be, for example, an inducible promoter.

Some aspects of the present disclosure provide human induced pluripotent stem (hiPS) cells modified to overexpress a gene encoding GATA4 protein. In some embodiments, a cell comprises a nucleic acid that comprises a promoter operably linked to a gene encoding Gata4 protein. In some embodiments, a promoter is an inducible promoter. In some embodiments, a nucleic acid is a lentiviral vector.

Some aspects of the present disclosure provide methods that comprise overexpressing a gene encoding GATA4 protein in a human induced pluripotent stem (hiPS) cell. In some embodiments, methods comprise transfecting hiPS cells with a nucleic acid that comprises a promoter operably linked to a gene encoding GATA4 protein. In some embodiments, a promoter is an inducible promoter. In some embodiments, a nucleic acid is a lentiviral vector.

In some embodiments, methods comprise (a) transfecting hiPS cells with a nucleic acid that constitutively expresses a doxycycline-activatable transactivator (rtTA), (b) transfecting hiPS cells with a nucleic acid encoding a promoter operably linked to the gene encoding GATA4 protein, wherein the promoter comprises a binding site for rtTA, and (c) culturing hiPS cells in the presence of doxycycline, thereby activating expression of Gata4 protein.

Some aspects of the present disclosure provide methods that comprise (a) isolating somatic cells from a human, (b) inducing pluripotency in isolated somatic cells of (a), thereby producing human induced pluripotent stem (hiPS) cells, (c) overexpressing in hiPS cells of (b) a gene encoding GATA4 protein at a level sufficient to produce heterogeneous tissue, and (d) culturing hiPS cells of (c) for a time sufficient to produce heterogeneous tissue that comprises cells selected from hepatic endodermal cells, hepatoblast-like cells, cholangiocyte-like cells, endothelial progenitor cells, endothelial-like cells, hemogenic endothelial cells, erythrocyte-like cells, hematopoietic progenitor-like cells, mesenchymal progenitor cells, stellate-like cells, neurectodermal cells, neural plate-like cells, neural fold-like cells, and any combination thereof. In some embodiments, methods further comprise banking heterogeneous tissue produced from hiPS cells that overexpress a gene encoding GATA4 protein. In some embodiments, methods further comprise transplanting heterogeneous tissue produced from hiPS cells that overexpress a gene encoding GATA4 protein into a subject (e.g., a human subject, such as the human from whom somatic cells were isolated).

In some embodiments, methods further comprise isolating from heterogeneous tissue cells selected from hepatic endodermal cells, hepatoblast-like cells, cholangiocyte-like cells, endothelial progenitor cells, endothelial-like cells, hemogenic endothelial cells, erythrocyte-like cells, hematopoietic progenitor-like cells, mesenchymal progenitor cells, stellate-like cells, neurectodermal cells, neural plate-like cells, neural fold-like cells, and any combination thereof, thereby producing isolated cells. In some embodiments, methods further comprise banking isolated cells. In some embodiments, methods further comprise transplanting isolated cells into a subject (e.g., a human subject, such as the human from whom somatic cells were isolated).

Aspects of the present disclosure provide methods that comprise culturing in cell culture media human induced pluripotent stem (hiPS) cells modified to overexpress a gene encoding SOX17 protein.

In some embodiments, hiPS cells overexpress a gene encoding SOX17 protein at levels sufficient to produce mesodermal cells, endodermal cells, ectodermal cells, or any combination thereof. In some embodiments, hiPS cells are cultured for a time sufficient to produce pluripotent cells, mesodermal cells, endodermal cells, ectodermal cells, or any combination thereof.

In some embodiments, hiPS cells overexpress a gene encoding SOX17 protein at levels sufficient to produce heterogeneous tissue. In some embodiments, hiPS cells are cultured for a time sufficient to produce heterogeneous tissue. In some embodiments, hiPS cells are cultured for at least 7 to 15 days.

In some embodiments, heterogeneous tissue produced from hiPS cells that overexpress a gene encoding SOX17 protein comprises hepatic endodermal cells, hepatoblast-like cells, cholangiocyte-like cells, endothelial progenitor cells, endothelial-like cells, hemogenic endothelial cells, erythrocyte-like cells, hematopoietic progenitor-like cells, mesenchymal progenitor cells, stellate-like cells, neurectodermal cells, neural plate-like cells, neural fold-like cells, or any combination thereof.

Some aspects of the present disclosure provide human induced pluripotent stem (hiPS) cells modified to overexpress a gene encoding SOX17 protein.

Some aspects of the present disclosure provide methods that comprise overexpressing a gene encoding SOX17 protein in a human induced pluripotent stem (hiPS) cell.

In some embodiments, hiPS cells of the present disclosure are modified to stably express a gene encoding SOX17 protein. Human iPS cells, in some embodiments, comprise a nucleic acid that comprises a promoter operably linked to a gene encoding SOX17 protein. A promoter may be, for example, an inducible promoter.

Some aspects of the present disclosure provide human induced pluripotent stem (hiPS) cells modified to overexpress a gene encoding SOX17 protein. In some embodiments, a cell comprises a nucleic acid that comprises a promoter operably linked to a gene encoding SOX17 protein. In some embodiments, a promoter is an inducible promoter. In some embodiments, a nucleic acid is a lentiviral vector.

Some aspects of the present disclosure provide methods that comprise overexpressing a gene encoding SOX17 protein in human induced pluripotent stem (hiPS) cells. In some embodiments, methods comprise transfecting hiPS cells with a nucleic acid that comprises a promoter operably linked to a gene encoding SOX17 protein. In some embodiments, a promoter is an inducible promoter. In some embodiments, a nucleic acid is a lentiviral vector.

In some embodiments, methods comprise (a) transfecting hiPS cells with a nucleic acid that constitutively expresses a doxycycline-activatable transactivator (rtTA), (b) transfecting hiPS cells with a nucleic acid encoding a promoter operably linked to the gene encoding SOX17 protein, wherein the promoter comprises a binding site for rtTA, and (c) culturing hiPS cells in the presence of doxycycline, thereby activating expression of SOX17 protein.

Some aspects of the present disclosure provide methods that comprise (a) isolating somatic cells from a human, (b) inducing pluripotency in isolated somatic cells of (a), thereby producing human induced pluripotent stem (hiPS) cells, (c) overexpressing in hiPS cells of (b) a gene encoding SOX17 protein at a level sufficient to produce heterogeneous tissue, and (d) culturing hiPS cells of (c) for a time sufficient to produce heterogeneous tissue that comprises cells selected from hepatic endodermal cells, hepatoblast-like cells, cholangiocyte-like cells, endothelial progenitor cells, endothelial-like cells, hemogenic endothelial cells, erythrocyte-like cells, hematopoietic progenitor-like cells, mesenchymal progenitor cells, stellate-like cells, neurectodermal cells, neural plate-like cells, neural fold-like cells, and any combination thereof. In some embodiments, methods further comprise banking heterogeneous tissue produced from hiPS cells that overexpress a gene encoding SOX17 protein. In some embodiments, methods further comprise transplanting heterogeneous tissue produced from hiPS cells that overexpress a gene encoding SOX17 protein into a subject (e.g., a human subject, such as the human from whom somatic cells were isolated).

In some embodiments, methods further comprise isolating from heterogeneous tissue cells selected from hepatic endodermal cells, hepatoblast-like cells, cholangiocyte-like cells, endothelial progenitor cells, endothelial-like cells, hemogenic endothelial cells, erythrocyte-like cells, hematopoietic progenitor-like cells, mesenchymal progenitor cells, stellate-like cells, neurectodermal cells, neural plate-like cells, neural fold-like cells, and any combination thereof, thereby producing isolated cells. In some embodiments, methods further comprise banking isolated cells. In some embodiments, methods further comprise transplanting isolated cells into a subject (e.g., a human subject, such as the human from whom somatic cells were isolated).

In some embodiments, cell culture media is hiPS cell pluripotency media. hiPS cell pluripotency media may be, for example, pure Iscove's Modified Dulbecco's Medium (IMDM) media. In some embodiments, cell culture media does not contain additional cytokines and/or growth factors. In some embodiments, cell culture media does not contain serum.

In some embodiments, hiPS cells are from a cell line selected from PGP-1, PGP-5, PGP-9 and C1.

Some aspects provide cells produced by a method of the present disclosure.

Other aspects provide heterogeneous tissues produced by a method of the present disclosure.

Yet other aspects provide methods of culturing an agent in the presence of a heterogeneous tissue of the present disclosure, and assessing toxic effects of the agent on the tissue. In some embodiments, the agent is a nucleic acid, a protein, or a small molecule drug.

Still other aspects provide methods of culturing an agent in the presence of a heterogeneous tissue of the present disclosure, and assessing metabolic activity of the tissue. In some embodiments, the agent is a nucleic acid, a protein, or a small molecule drug.

Some aspects of the present disclosure provide methods of culturing heterogeneous tissue for a time sufficient to produce an organ, or an organ-like tissue (e.g., liver, or liver-like tissue). Also provided herein are organs produced by culturing heterogeneous tissue of the present disclosure.

BRIEF DESCRIPTION OF THE DRAWINGS

FIG. 1A shows examples of lentiviral constructs used to generate stable cell lines of the present disclosure. FIG. 1B shows an example of a general timeline for experiments, media conditions and cell extractions for an exome microarray analysis.

FIG. 2A shows that an engineered human induced pluripotent stem (hiPS) cell line B (mKate2-expressing cells) localized to a non-endodermal sub-population, while high GATA6-2A-EGFP-expressing cells segregated to the endodermal sub-population. Left panel: lentiviral constructs. Middle panel: cell culture at day 0 (addition of doxycycline (Dox) to the cell culture medium). Right panel: day 5 (5 days after Dox was added to the cell culture medium). FIG. 2B shows that Dox-induced ectopic expression of lentivirally-delivered GATA6 lead to segregation into GATA6$^+$ and NANOG$^+$ cell populations. Left panel: day 3, without addition of Dox. Middle panel: day 3, with addition of Dox, shows segregation of GATA6$^+$ and NANOG$^+$ cell populations. Right panel: day 3, shows Brachyury/T$^+$ cells interspersed with FOXA2$^+$ endodermal cells. FIG. 2C, left panel, shows an immunostain of Dox-induced GATA6-expressing hiPS cells for FOXA2, GATA6-HA and NANOG. Middle panel: Image analysis of the image in the left panel using Cellprofiler (BROAD Institute, Cambridge Mass.). Within the endodermal sub-population little GATA6-HA expression suffices to acquire the endodermal marker FOXA2, while FOXA2 expression is repressed within the NANOG+ sub-population. FIG. 2D shows CXCR4$^+$ cells at day 3 (Left panel) and day 5 (middle panel) and their transcriptional profiling (heat map on left). Scale bars: 200 µm. D: day of the experiment (D0=Addition of Dox to the cell culture medium). Log 2NI: log 2 normalized intensities. Scale bar: 200 µm.

FIG. 3A, right panel, shows that CD34 and CD93 co-localize in endothelial-like cells at day 7. CEBPA expression marks hepatic endoderm in the background. Middle panel: Development of endothelial progenitors is marked by expression of CD31 (arrows indicate CD31 signal) at day 10. CD34 expression is present in the hepatoblast-like cell fraction (CEBPA$^+$/CD146$^-$) as well as in the endothelial-like cell fraction (CEBPA$^-$/CD146$^+$). Right panel: CD51$^+$/NES$^+$/PDGFRA$^+$ mesenchymal stem cell-like cells developed in conjunction with the hepatoblasts at day 10. Heatmap below: Temporal upregulation of markers indicative of endothelial and hematopoietic development. CD34$^+$ isolated/enriched cells at day 10.

FIG. 4A shows an example of cultured cells of the present disclosure developing into a complex, heterogeneous tissue. Top left panel: shows immunostaining for CD34$^+$ cells, CD31$^+$ cells and CEBPA$^+$ cells at day 14. Top middle panel: shows immunostaining for DES$^+$ cells and DLK1$^+$ cells at day 14. Top right panel: shows immunostaining for CK19$^+$ cells, CD146$^+$ cells and ATT$^+$ cells at day 14. Bottom left panel: shows immunostaining for CK7$^+$ cells, CK19$^+$ cells and CEBPA$^+$ cells at day 14. CK7-positive bile duct-like channels developed within hepatoblasts; XZ and YZ slices on the left and bottom. Bottom middle panel: further maturation of the liver-like tissue was evidenced by increasing albumin (ALB) production (ELISA) and increasing numbers of ALB$^+$ cells. Bottom right panel: phALB_RFP: Lentivirally-integrated reporter with a short human albumin promoter driving expression of a red fluorescent protein (RFP) in cells at day 18.

FIGS. 5A-5C show that ectopic expression of GATA6 induces segregation into a GATA6$^+$ endodermal sub-population and clusters of an OCT4$^+$/NANOG$^+$ pluripotent sub-population. FIG. 5A shows rapid expression of ectopic GATA6 resulting in segregation of cells into a NANOG$^+$ and FOXA2$^+$ sub-population. FIG. 5B shows segregation into an OCT4$^+$ and GATA6+ sub-population. FIG. 5C shows daily immunostaining for FOXA2. Scale bar: 200 µm.

FIG. 6A shows Dox-titration and impact on endoderm generation. Increasing amounts of Dox shift the endoderm ratio within the population. FIG. 6B shows that mixing GATA6-expressing and non-expressing cells enables modulation of an endoderm to non-endoderm ratio within the population. Scale bar: 200 µm.

FIGS. 7A-7D show results from a symmetry break analysis at the single cell level. FIG. 7A shows an example of cultured cells of the present disclosure expressing the endodermal biomarker, FOXA2$^+$, induced by Gata6-hemagglutinin (HA) expression. FIG. 7B shows that GATA6 expression must reach a defined threshold for FoxA2 to be expressed. FIGS. 7C and 7D show that cells with intermediate GATA6(-HA) expression levels localize to an endoderm sub-population if NANOG expression is low, otherwise the cells localize to the NANOG$^+$ sub-population. D: day. Scale bar: 200 µm.

FIGS. 8A-8E show maturation of specific cell populations. FIG. 8A shows endodermal-like CD34$^+$ cells at day 5 and endothelial-like CD34$^+$ cells at day 7. FIG. 8B shows cells expressing TAL1/CD34, biomarkers indicative of hematopoietic commitment of these cells. FIG. 8C shows DES$^+$ cells in a population of NES$^+$ cells around day 10.

FIG. 8D shows CD133+/CEBPA+ co-expression, indicative of hepatoblast cells, around day 10. FIG. 8E shows a confocal image of cells co-expressing LGR5 and AAT in hepatoblasts at day 10.

FIGS. 10A-10B show that clusters of cells not differentiating to mesendoderm acquire a neural cell fate. FIG. 10A shows increased expression of OCT4 in the non-endodermal clusters within the first five days. FIG. 10B shows that islands of formerly pluripotent cells within the endodermal layer (FOXA2+ cells) acquired a neuroectodermal identity (SOX10+, AP2+ cells). Scale bars: 200 µm. Log 2NI: log 2 normalized intensities. Heatmap of the 15 most upregulated genes in the neural-fold like tissue and three control genes (UBC, EEF1A, NANOG); uat=unknown anti-sense transcript. All scale bars are 200 µm. U: Uninduced (no Dox), EO: Ectodermal outgrowths. Log 2NI: log 2 normalized intensities.

FIG. 11A shows PGP1, PGP5 and PGP9 hiPS cell-derived liver-like tissue fixed on day 14 and stained for CD34 (Endothelial progenitors/EnLCs), CD31 (EnLCs), CEBPA (HpLCs) and DAPI (Nucleus). FIG. 11B shows PGP1, PGP5, PGP9 hiPS cell-derived heterogeneous tissue fixed on day 14 and stained for Desmin (DES) (stellate-like cells) and DLK1 (hepatoblast-like cells). FIG. 11C shows and C1 hiPS cell-derived heterogeneous tissue fixed on day 14 and stained for CD31 (endothelial-like cells), CK19 (hepatoblast-like cells), AAT (hepatoblast-like cells) and DAPI, respectively. Scale bar: 200 µm.

FIG. 12 shows an example of cultured cells at day 10 immunostained cells for CEBPA (hepatic endoderm), TTF1 (lung endoderm) and PDX1 (pancreatic endoderm). Small clusters of both lung and pancreatic endoderm are present and suggests that methods of the present disclosure can generate lung-like and as well as pancreas-like tissue.

FIGS. 13A-13B show that an ectodermal cell sub-population expressed markers of neural crest. FIG. 13A shows extracted ectodermal outgrowths. FIG. 13B shows a neural crest differentiation pathway (Dark gray: upregulated genes on day 14 vs. uninduced hiPS cells).

FIG. 14A shows that CXCR4+ cells were hypermotile and localized to edges of the endodermal layer. FIG. 14B shows a Microarray analysis of sub-populations at day 5 post-induction. The CXCR4-enriched subpopulation expressed markers of anterior and posterior foregut.

FIG. 15A shows that a significant 10-fold decrease of fibrinogen was observed with the addition of doxycycline to cell media. FIG. 15B shows microscopy images of cells cultured with 500 mg/mL (left) and 50 mg/mL (right) of doxycycline in media. There are decreased areas of differentiated cells in culture. FIG. 15C shows that fibrinogen production is also significantly decreased with the introduction of wild-type cells to modified cells expressing GATA6. FIG. 15D shows microscopy images of cultures seeded with WT:GATA6 ratios of 0:50, 1:49 and 10:40, respectively. The WT cells modified to express red fluorescent protein (RFP) migrated to form a distinct boundary with the cells modified to express GATA6. Both imaging and media assay were performed at day 13 of cultures.

FIG. 16A shows a flow cytometry quantitation of HNF4A positive cells using intracellular staining for days 6, 10, and 14 of culture. Histograms of the cell population with their negative control are shown. FIG. 16B shows AAT production on days 6, 10, and 14 of culture per million HNF4A positive cells. FIG. 16C shows fibrinogen production on days 6, 10, and 14 of culture per million HNF4A positive cells.

FIG. 17A shows histograms of EGFP expression in uninduced (left) or 2 day-induced GATA6 modified iPS cells (right). After 2 days of induction Gata6-EGFP+ cells were sorted into four populations based on EGFP signal intensity, then reseeded. P1, P2, P3 and P4 are listed from lowest EGFP expression to highest. FIG. 17B shows images of each sorted population for days 4, 8 and 12 of cultures. At day 14, cells were fixed and stained for AAT (hepatocyte) and CD34 (vascular endothelial cells).

FIGS. 19A-19D show an overview over a differentiation process. FIG. 19A shows schematics of transgenes used in Example 2: constitutively expressed rtTA3 binds upon addition of doxycycline (Dox) to TRET and induces expression of GATA6 or GATA6 and MIX1-1. FIG. 19B shows immunofluorescence staining for FOXA2 and SOX17 five days post-induction. FIG. 19C shows immunofluorescence staining for TRA-1-81 (pluripotency biomarker) and CXCR-4 (endoderm biomarker) five days post-induction, indicative of GATA6-induced endoderm and islands containing pluripotent iPS cells. FIG. 19D shows a timeline for the experiments present in Example 2 and upregulated markers in relation to two additional time points (immunofluorescence and Agilent microarrays on total RNA).

FIG. 20A shows images acquired for 8 days after Dox induction. Pluripotent islands and GATA6-induced cells were still recognizable. Emergent structures began to grow in the center of the pluripotent islands. FIG. 20B shows images acquired 13 days after Dox induction. Left: emergent structures on a background of GATA6-induced endoderm. Right: harvested tissue for total RNA extraction (used for the Agilent microarray transcriptome analysis). FIG. 20C shows images acquired 35 days after Dox induction. A stable layer of hepatocyte-like cells has formed.

DETAILED DESCRIPTION OF THE INVENTION

Figure 1C:
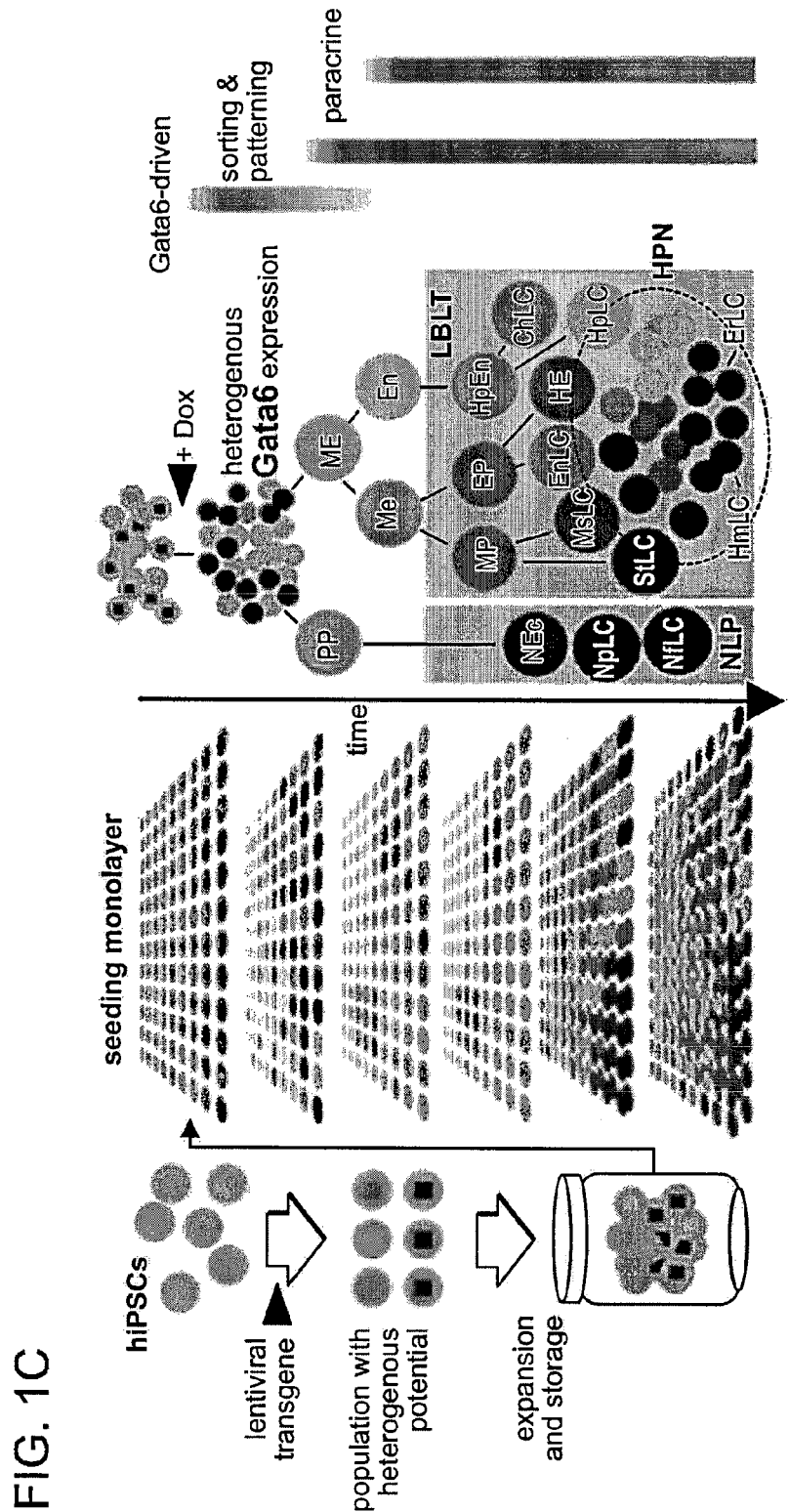
FIG. 1C shows an overview of a method of the present disclosure and cell types generated during the method.

Self-organization and emergence are two inherent capabilities of human induced pluripotent stem (hiPS) cells. Organs usually include cells derived from more than one germ layer and develop from autologous, singly derived hiPS cells, as this is likely to yield the best chance for practical therapeutic applications in the long term[8]. The liver, for example, is an important target for growing replacement organs. Viral hepatitis affects approximately 500 million people around the world, and liver diseases are a major and increasingly common cause of premature death[9]. The ability to re-grow a liver-like organ, as well as other organs, from hiPS cells would not only eliminate the donor bottleneck, but it would also make it possible to genetically engineer[10] these cells, for example, to correct for genetic disorders or to better resist specific diseases.

There is also a need for better in vitro tissue models with human cells to bridge the gap to existing animal models. Such in vitro tissue models can be used, for example, for developing and screening new drugs and for understanding complex diseases in the context the human physiology.

Both regenerative medicine approaches as well as in vitro models depend on a robust protocol to grow organ-like tissue. Organ morphogenesis during embryonic and fetal development is an inherently complex process. During liver morphogenesis, for example, definitive endoderm and mesoderm are generated as cells of the epiblast undergo gastrulation in the late blastocyst. Definitive endoderm differentiates to the foregut lineage and then to hepatic endoderm by morphogen gradients and other local cues. Cells of the hepatic endoderm then delaminate and invade the neighboring septum transversum mesenchyme (STM), forming the early liver bud. Endothelial progenitors emerge and begin to vascularize the tissue. The yolk sac adjacent to the liver bud provides hematopoietic progenitors, which invade the liver bud, where they expand as well as mature further. Signals from the developing heart are involved in liver bud formation and maturation as well. Orchestration of these processes requires interplay between mesenchymal, hepatic endodermal, endothelial and extraembryonic progenitors cells[11,12]. The spatial relationships within the developing embryo of these disparate and seemingly unrelated cell types also have an important role.

Provided herein, in some embodiments, are methods for engineering differentiation processes involving multiple germ layers. Transcription factors involved in directing the differentiation of endodermal and mesodermal lineages were investigated, and results demonstrated that the ectodermal fate could be acquired 'for free' without engineering, as it is the default pathway. Further, examples presented herein show that ectopic expression of transcription factor GATA6 induces the production of complex, heterogeneous tissue that includes myriad cell types of the three germ layers. GATA6 is involved in a wide range of functions such as segregation of the blastocyst's inner cell mass (ICM) into epiblast and primitive endoderm, gastrulation, mesoderm specification, cardiac development, lung endoderm branching, mesenchymal to epithelial transitions, and organogenesis of pancreas, gut and liver, among others[14,15,16].

An overview of a method of the present disclosure and cell types generated during the method are shown in FIG. 1C. Human inducible pluripotent stem (hiPS) cells containing a nucleic acid encoding an inducible Gata6 transgene were seeded in a monolayer, Gata6 transgene expression was triggered with a small molecule (e.g., Dox), and the cells were left to co-differentiate into a variety of different cell types. Starting with an undifferentiated monolayer of hiPS cells, complex three-dimensional tissue was obtained after 15 days. (LBLT: Liver bud-like tissue, NPL: Neuronal progenitor-like, HPN: Hematopoietic Niche, ME: Mesendoderm, PP: pluripotent cells (expressing pluripotency markers, not induced to mesendoderm), En: Endoderm, Me: Mesoderm, Ec: Ectoderm, HpEn: Hepatic endoderm, EP: Endothelial progenitors, MP: Mesenchymal progenitors, NEc: Neurectoderm, HpLC: Hepatoblast-like cells, ChLC: Cholangiocyte-like cells, EnLC: Endothelial-like cells, NpLC: Neural plate-like cells, HE: Hemogenic Endothelium, ErLC: Erythrocyte-like cells, HmLC: Hematopoietic progenitor-like cells, StLC: Stellate-like cells, MsLC: Mesenchyme-like cells, NfLMC: Neural fold-like cells).

A "human induced pluripotent stem cell," or "hiPS cell," refers to a somatic (e.g., mature or adult) cell that has been reprogrammed to an embryonic stem cell-like state by being forced to express genes and factors important for maintaining the defining properties of embryonic stem cells (see, e.g., Takahashi and Yamanaka, *Cell* 126 (4): 663-76, 2006, incorporated by reference herein). Human iPS cells express stem cell markers and are capable of generating cells characteristic of all three germ layers (ectoderm, endoderm, mesoderm). Human iPS cells can be produced, for example, by expressing four transcription factor genes encoding OCT4, SOX2, KLF4 and c-MYC. Other methods for producing hiPS cells are also contemplated herein.

A "stem cell" refers to a cell with the ability to divide for indefinite periods in culture and to give rise to specialized cells. A "pluripotent stem cell" refers to a type of stem cell that is capable of differentiating into all tissues of an organism, but not alone capable of sustaining full organismal development.

A cell, such as a hiPS cell, is considered "modified" if it contains a nucleic acid that is not present in an unmodified cell. In some embodiments, a cell is modified by introducing into the cell a nucleic acid that expresses a gene encoding a protein of interest (e.g., GATA6, GATA4 or SOX17). In some embodiments, a cell is modified by introducing a recombinant nucleic acid into the cell in order to produce a genetic change of interest (e.g., via insertion or homologous recombination). In some embodiments, a cell is modified to overexpress an endogenous protein of interest (e.g., via introducing or modifying a promoter or other regulatory element near the endogenous gene that encodes the protein of interest to increase its expression level). In some embodiments, a cell is modified by mutagenesis.

In some embodiments, a hiPS cell is modified to overexpress a gene and/or protein. "Overexpression" refers to expression of a gene and/or protein in a modified cell at a level greater than a level of expression of the same respective gene and/or protein in an unmodified cell. In some embodiments, a gene and/or protein is considered overexpressed in a modified cell if the expression level of the respective gene and/or protein is at least 10%, at least 20%, at least 30%, at least 40% or at least 50% greater than the expression level of the same respective gene and/or protein in an unmodified cell. For example, the expression level of an overexpressed gene and/or protein may be 10%, 15%, 20%, 25%, 30%, 35%, 40%, 45%, 50%, 60%, 65%, 70%, 75%, 80%, 85%, 90%, 95%, 100%, 200%, or greater than the expression level of the same respective gene and/or protein in an unmodified cell.

"Transient cell expression" herein refers to expression by a cell of a nucleic acid that is not integrated into the nuclear genome of the cell. By comparison, "stable cell expression" herein refers to expression by a cell of a nucleic acid that remains in the nuclear genome of the cell and its daughter cells. Typically, to achieve stable cell expression, a cell is co-transfected with a marker gene and an exogenous nucleic acid that is intended for stable expression in the cell. The marker gene gives the cell some selectable advantage (e.g., resistance to a toxin, antibiotic, or other factor). Few transfected cells will, by chance, have integrated the exogenous nucleic acid into their genome. If a toxin, for example, is then added to the cell culture, only those few cells with a toxin-resistant marker gene integrated into their genomes will be able to proliferate, while other cells will die. After applying this selective pressure for a period of time, only the cells with a stable transfection remain and can be cultured further. In some embodiments, puromycin, an aminonucleoside antibiotic, is used as an agent for selecting stable transfection of hiPS cells. Thus, in some embodiments, hiPS cells are modified to express puromycin N-acetyltransferase, which confers puromycin resistance to the hiPS cells expressing puromycin N-acetyltransferase. Other marker genes/selection agents are contemplated herein. Examples of such marker genes and selection agents include, without limitation, dihydrofolate reductase with methotrexate, glutamine synthetase with methionine sulphoximine, hygromycin phosphotransferase with hygromycin, and neomycin phosphotransferase with Geneticin, also known as G418.

Human iPS cells of the present disclosure may, in some embodiments, overexpress a gene encoding a protein (e.g., GATA6, GATA4 or SOX17) at levels sufficient to produce mesodermal cells, endodermal cells, ectodermal cells, or any combination thereof. "Mesoderm" refers to the middle layer of a group of cells (e.g., mesodermal cells) derived from the inner cell mass of a blastocyst. Mesoderm gives rise to bone, muscle, connective tissue, kidneys, and related structures. "Endoderm" refers to the innermost layer of the cells (e.g., endodermal cells) derived from the inner cell mass of the blastocyst. Endoderm gives rise to lungs, other respiratory structures, and digestive organs, or generally "the gut." "Ectoderm" refers to the outermost germ layer of cells (e.g., ectodermal cells) derived from the inner cell mass of the blastocyst. Ectoderm gives rise to the nervous system, sensory organs, skin, and related structures.

Gene or protein expression levels "sufficient to produce" a particular cell type are respectively gene or protein levels that induce (e.g., cause) expression of biomarkers typically detected in that particular cell type. For example, a GATA6 protein expression level sufficient to produce mesodermal cells is a protein expression level that induces hiPS cells to express mesodermal cell biomarkers (e.g., T (Brachyury) CD31, CD34). As another example, a GATA6 protein expression level sufficient to produce endodermal cells is a protein expression level that induces hiPS cells to express endodermal cell biomarkers (e.g., FOXA2, SOX17). As yet another example, a GATA6 protein expression level sufficient to produce ectodermal cells is a protein expression level that induces hiPS cells to express ectodermal cell biomarkers (e.g., SOX6, SOX10). In some embodiments, hiPS cells that express no, or low, levels of GATA6 protein differentiate into ectodermal cells.

Gene or protein levels sufficient to produce a particular cell or tissue (e.g., heterogeneous tissue) may depend, in some instances, on spatial organization and patterning of cells/cellular environment (see, e.g., FIG. 2C) and temporal sequence.

Human iPS cells of the present disclosure, in some embodiments, are cultured for a time sufficient to produce pluripotent cells, mesodermal cells, endodermal cells, ectodermal cells, or any combination thereof. A time "sufficient to produce" a particular cell type is a period of time necessary for a particular gene to be expressed and to induce (e.g., cause) expression of biomarkers typically detected in that particular cell type. A sufficient time for induction of expression of a particular biomarker may depend on several factors, including gene and/or protein expression levels in the cell and other intracellular and extracellular factors. In some embodiments, hiPS cells are cultured for at least 1 day to at least 50 days, or more. In some embodiments, hiPS cells are cultured for at least 1 day to at least 25 days, or at least 1 day to at least 15 days. In some embodiments, hiPS cells are cultured for 1 to 20 days, 1 to 15 days, 1 to 10 days, 1 to 5 days, 3 to 20 days, 3 to 15 days, 3 to 10 days, 5 to 20 days, 5 to 15 days, or 5 to 10 days. In some embodiments, hiPS cells are cultured for 1, 2, 3, 4, 5, 6, 7, 8, 9, 10, 11, 12, 13, 14, 15, 16, 17, 18, 19, 20, or 21 days. In some embodiments, hiPS cells are cultured for 1 week, 2 weeks, 3 weeks, 4 weeks, 1 month, 2 months, 3 months, 4 months, 5 months, or 6 months, or more. In some embodiments, hiPS cells are cultured for a foregoing period of time, and then transplanted (e.g., in a permeable capsule, e.g., alginate-based capsule[36]) into a subject (e.g., human subject) for continued maturation of the cells/heterogeneous tissue.

"Heterogeneous tissue" refers to three-dimensional tissue (e.g., more than one monolayer) that includes cells that express biomarkers indicative of the presence of mesodermal, endodermal and ectodermal cells and/or cell lineages (e.g., indicative of cells of, or cells derived from (e.g., daughter cells of), each of the three germ layers). Cells that express at least one (e.g., at least one, at least two, at least three, or more) biomarkers indicative of a specific cell type may be referred to as "X-like cells," where X is a known cell type. For example, cells that express at least one hepatoblast biomarker may be referred to as "hepatoblast-like cells." As another example, cells that express as least one erythrocyte biomarker may be referred to as "erythrocyte-like cells." Heterogeneous tissue of the present disclosure may, in some embodiments, include cells (e.g., growing/developing together) that expression biomarkers indicative of hepatic endoderm (HpEn), endothelial progenitors (EP), mesenchymal progenitors (MP), neuroectoderm (NEc), hepatoblast-like cells (HpLC), cholangiocyte-like cells (ChLC), endothelial-like cells (EnLC), neural plate-like cells (NpLC), hemogenic endothelium (HE), erythrocyte-like cells (ErLC), hematopoietic progenitor-like cells (HmLC), stellate-like cells (StLC), mesenchyme-like cells (MsLC), neural fold-like cells (NfLC), or any combination of at least two of the foregoing cell types. Biomarkers for each of the cell types are shown in Table 1.

TABLE 1

| Cell type | Biomarkers |
| --- | --- |
| pluripotent cells | OCT4+, NANOG+, TRA-1-80+ |
| mesendoderm (ME) | MIXL1+ |
| endoderm (En) | FOXA2+, SOX17+ |
| hepatic endoderm (HpEn) | CEBPA+, HNF4A+, FOXA2+, HHEX+ |
| hepatoblast-like cells (HpLC) | CD133+, AAT+, CEBPA+, FOXA2+, AFP+, LGR5+, CK19+, often DLK1+, later stages: ALB+ |
| cholangiocyte-like cells (ChLC) | CK7+, AQP1+ |
| mesoderm (Me) | Brachyury+ (T+) |
| mesenchymal progenitors (MP) | CD51+, NES+, PDGFRA+ |
| endothelial progenitors (EP) | CD34+, CEBPA− |
| mesenchyme-like cells (MsLC) | NES+, PDGFRA+ |
| stellate-like cells (StLC) | DES+ |
| endothelial-like cells (EnLC) | CD31+ |
| hemogenic endothelium (HE) | CD34+, TAL1+, FLK1+, CD93+ |
| erythrocyte-like cells (ErLC) | Hemoglobin+ |
| hematopoietic progenitor-like cells (HmLC) | CD45+ |
| ectoderm (Ec) | OCT4+, SOX10+, NES+ |
| neuroectoderm (NEc) | OCT4+, SOX10+, AP2A+ |
| neural plate-like cells (NpLC) | OCT4−, SOX10+, AP2A− |
| neural fold-like cells (NfLC) | PAX7+, DLX5+, FOXG1+, PAX6+ |

In some embodiments, hiPS cells overexpress a gene encoding a protein (e.g., GATA6, GATA4 or SOX17) at levels sufficient to produce heterogeneous tissue. Gene or protein expression levels "sufficient to produce heterogeneous tissue" are respectively gene or protein levels that induce (e.g., cause) expression of biomarkers typically detected in cells of, or cells derived from, each of the three germ layers. For example, a GATA6 protein expression level sufficient to produce heterogeneous tissue is a protein expression level that induces hiPS cells to express mesodermal cell biomarkers (e.g., CD31, CD34), endodermal cell biomarkers (e.g., FOXA2), and ectodermal cell biomarkers (e.g., SOX10, PAX6).

Human iPS cells of the present disclosure, in some embodiments, are cultured for a time sufficient to produce heterogeneous tissue. A time "sufficient to produce heterogeneous tissue" is a period of time necessary for at least one gene to be expressed and to induce (e.g., cause) expression of biomarkers typically detected in cells of, or cells derived from, each of the three germ layers.

"Differentiation" refers to the process whereby an unspecialized cell (e.g., embryonic cell or stem cell) acquires the features of a specialized cell such as, for example, a heart, liver, or muscle cell. Differentiation is controlled by the interaction of a cell's genes with the physical and chemical conditions outside the cell, usually through signaling pathways involving proteins embedded in the cell surface. An "undifferentiated cell" refers to a cell that has not yet developed into a specialized cell type.

A cell that expresses a particular biomarker at a detectable level (e.g., detectable by immunostaining) is referred to as a positive (+) cell with respect to that particular biomarker. Thus, a cell that expresses GATA6 at a detectable level is a GATA6$^+$ cell. A cell that does not express a particular biomarker at a detectable level is referred to as a negative (−) cell with respect to that particular biomarker. Thus, a cell that does not express GATA6 at a detectable level is a GATA6$^-$ cell. In some embodiments, a cell that is "negative" for a biomarker may express the biomarker, albeit at an undetectable (e.g., low) level.

Human iPS cells may be modified through transgene expression or delivery of protein (e.g., purified protein). Transgene expression methods that may be used, as provided herein include, without limitation, lentiviral gene delivery, use of RNA replicons or modified RNA[30]. In some embodiments, protein (e.g., GATA6, GATA4 or SOX17) is delivered directly to hiPS cells by, for example, electroporation[34]. In some embodiments, a protein is delivered to a hiPS cell using a cell penetrating peptide (CPP) (e.g., a peptide that includes a high proportion of arginine or lysine)[39]. Thus, provided herein, in some aspects, are methods that comprise culturing in cell culture media human induced pluripotent stem (hiPS) cells modified to include GATA6 protein.

Aspects of the present disclosure relate to hiPS cells that overexpress a gene encoding GATA6 protein. In some embodiments, a GATA6 gene is encoded by a nucleic acid sequence that comprises the sequence set forth as NCBI Accession No. NM_005257.4 (SEQ ID NO: 1). In some embodiments, a GATA6 protein is encoded by an amino acid sequence that comprises the sequence set forth as NCBI Accession No. NP_005248.2 (SEQ ID NO: 2).

Aspects of the present disclosure relate to hiPS cells that overexpress a gene encoding GATA4 protein. In some embodiments, a GATA6 gene is encoded by a nucleic acid sequence that comprises the sequence set forth as NCBI Accession No. NM_002052.3 (SEQ ID NO: 3). In some embodiments, a GATA4 protein is encoded by an amino acid sequence that comprises the sequence set forth as NCBI Accession No. NP_002043.2 (SEQ ID NO: 4).

Aspects of the present disclosure relate to hiPS cells that overexpress a gene encoding GATA4 protein. In some embodiments, a GATA6 gene is encoded by a nucleic acid sequence that comprises the sequence set forth as NCBI Accession No. NM_022454.3 (SEQ ID NO: 5). In some embodiments, a GATA4 protein is encoded by an amino acid sequence that comprises the sequence set forth as NCBI Accession No. NP_071899.1 (SEQ ID NO: 6).

Human iPS cells may be cultured, in some embodiments, using standard cell culture methods[35,38]. Several factors influence the quality, robustness and utility of hiPS cell culture methods including, for example, culture medium, extracellular matrices, and environmental cues, including cues from both physical and physiological environments (e.g., temperature, humidity, osmosity, acidity, rigidity of growth surfaces, cell density, gas diffusion exchange, and modes of multicellular associations).

In some embodiments, the culture medium (also referred to, in some instances, as growth medium) is serum-free, xeno-free and/or chemically defined. In other embodiments, serum (e.g., fetal bovine serum (FBS)) may be added to the culture medium. In some embodiments, the culture medium is a defined culture medium such as, for example, TeSR1[37], which includes FGF-2, lithium chloride, γ-aminobutric acid, TGF-β and pipeolic acid. In some embodiments E8 medium may be used, which is a derivative of TeSR1 containing eight components and lacks both serum albumin and b-mercaptoethanol. In some embodiments, additional cytokines and/or growth factors are added to the growth medium. In some embodiments, the culture medium does not contain additional cytokines and/or growth factors.

In some embodiments, hiPS cells are grown in the absence of feeder cells, while in other embodiments, feeder cells may be used.

Extracellular components for use herein include, without limitation, diverse organic matrices from animal cells, hydrogel, individual matrix proteins, synthetic surfaces and some commercially well-defined and xenogeneic-free components. In some embodiments Matrigel is used as an extracellular component for hiPS cell culture. It is a basement membrane matrix, rich in types I and IV collagens, laminin, entactin, heparan sulfate proteoglycan, matrix metalloproteinases, growth factors and chemical compounds. In some embodiments, the extracellular component (e.g., Matrigel) is diluted in growth medium (e.g., DMEM/F-12) at a dilution of 1:10 to 1:100, optionally with HEPES medium. In some embodiments, the dilution of the extracellular component (e.g., Matrigel) in growth medium is 1:10, 1:15, 1:20, 1:25, 1:30, 1:35, 1:40, 1:45, 1:50, 1:55, 1:60, 1:65, 1:70, 1:75, 1:80, 1:85, 1:90, 1:95 or 1:100. In some embodiments, the dilution of the extracellular component (e.g., Matrigel) in growth medium is 1:75. In some embodiments, extracellular matric components are coated onto tissue culture plates prior to the addition of hiPS cells for culture.

Human iPS cells may be cultured, in some embodiments, in an incubator (e.g., humidified incubator) at a temperature of between 30° C. and 40° C. In some embodiments, the temperature of the incubator is 37° C. The level of $CO_2$ in the incubator may be, for example, between 0% and 10%. In some embodiments, the level of $CO_2$ in the incubator is 5%. In some embodiments, hiPS cells are cultured in an incubator at a temperature of 37° C. in the presence of 5% $CO_2$.

In some embodiments, hiPS cells are cultured as single cell suspensions. In some embodiments, hiPS cells are first plated as a monolayer.

Some aspects of the present disclosure relate to hiPS cells modified to comprise nucleic acids, for example, encoding one or more proteins of interest (e.g., GATA6, GATA4 or SOX7). As used herein, the term "nucleic acid" refers to at least two nucleotides covalently linked together, and in some instances, may contain phosphodiester bonds (e.g., a phosphodiester "backbone"). Nucleic acids (e.g., components, or portions, of the nucleic acids) of the invention may be naturally occurring or engineered. Engineered nucleic acids include recombinant nucleic acids and synthetic nucleic acids. "Recombinant nucleic acids" refer to molecules that are constructed by joining nucleic acid molecules (e.g., naturally-occurring or synthetic) and, in some embodiments, can replicate in a living cell. "Synthetic nucleic acids" refer to molecules that are chemically, or by other means, synthesized or amplified, including those that are chemically or otherwise modified but can base pair with naturally occurring nucleic acid molecules. Recombinant and synthetic nucleic acids also include those molecules that result from the replication of either of the foregoing.

Nucleic acids may be single-stranded (ss) or double-stranded (ds), as specified, or may contain portions of both single-stranded and double-stranded sequence. The nucleic acid may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xanthine, hypoxanthine, isocytosine, and isoguanine.

In some embodiments, a nucleic acid comprises a promoter sequence, or promoter, operably linked to a nucleotide sequence encoding a protein of interest. As used herein, a "promoter" refers to a control region of a nucleic acid sequence at which initiation and rate of transcription of the remainder of a nucleic acid sequence are controlled. A promoter may also contain subregions at which regulatory proteins and molecules may bind, such as RNA polymerase and other transcription factors. Promoters may be constitutive, inducible, activatable, repressible, tissue-specific or any combination thereof. A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence.

A promoter may be classified as strong or weak according to its affinity for RNA polymerase (and/or sigma factor); this is related to how closely the promoter sequence resembles the ideal consensus sequence for the polymerase. The strength of a promoter may depend on whether initiation of transcription occurs at that promoter with high or low frequency. Different promoters with different strengths may be used to vary levels of gene/protein expression (e.g., the level of expression initiated from a weak promoter is lower than the level of expression initiated from a strong promoter).

A promoter may be one naturally associated with a gene or sequence, as may be obtained by isolating the 5' non-coding sequences located upstream of the coding segment and/or exon of a given gene or sequence. Such a promoter can be referred to as "endogenous." Similarly, an enhancer may be one naturally associated with a nucleic acid sequence, located either downstream or upstream of that sequence.

In some embodiments, a coding nucleic acid segment may be positioned under the control of a recombinant or heterologous promoter, which refers to a promoter that is not normally associated with the encoded nucleic acid sequence in its natural environment. A recombinant or heterologous enhancer refers to an enhancer not normally associated with a nucleic acid sequence in its natural environment. Such promoters or enhancers may include promoters or enhancers of other genes; promoters or enhancers isolated from any other mammalian cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR).

As used herein, an "inducible promoter" is one that is characterized by initiating or enhancing transcriptional activity when in the presence of, influenced by or contacted by an inducer or inducing agent. An "inducer" or "inducing agent" may be endogenous or a normally exogenous condition, compound or protein that contacts a genetic circuit in such a way as to be active in inducing transcriptional activity from the inducible promoter. In some embodiments, gene expression is induced using a tetracycline-controlled transcription activation system or a doxycycline-controlled transcription activation system. With such systems, gene transcription is reversibly turned on or off in the presence of the antibiotic tetracycline or one of its derivatives (e.g., doxycycline). For example, hiPS cells may be transfected with a first nucleic acid that constitutively expresses a doxycycline-activatable transactivator (rtTA) protein and a second nucleic acid encoding a promoter operably linked to the gene encoding GATA6 protein, wherein the promoter comprises a binding site for rtTA (referred to as an operator). In the presence of doxycycline, for example, the rtTa protein is capable of binding to the operator in the promoter, thereby activating expression of GATA6 protein.

In some embodiments, a promoter may or may not be used in conjunction with an "enhancer," which refers to a cis-acting regulatory sequence involved in the transcriptional activation of a nucleic acid sequence downstream of the promoter. The enhancer may be located at any functional location before or after the promoter.

Also contemplated herein are methods and assays for patient-driven dug discovery and clinical applications, such as, for example, transplantation medicine. Human iPS cells derived from patients, and heterogeneous tissue produced therefrom, can provide, in some embodiments, physiologically relevant cells in the quantity necessary to support in vitro assays used to understand basic mechanisms of disease and to identify safe and efficacious clinical compounds as well as iteratively relating patient information from the clinic back to a drug discovery laboratory[44]. A hiPS cells is considered to be derived from a patient (e.g., human having a paritcular condition or disease) if the hiPS cell is reprogrammed from a cell (e.g., somatic cell) obtained from that patient.

Provided herein, in some embodiments, are methods that include isolating somatic cells from a human, inducing pluripotency in the isolated somatic cells, thereby producing human induced pluripotent stem (hiPS) cells, overexpressing in the hiPS cells a gene encoding GATA6, GATA4 or SOX17 protein at a level sufficient to produce heterogeneous tissue, and culturing the hiPS cells for a time sufficient to produce heterogeneous tissue that comprises cells selected from hepatic endodermal cells, hepatoblast-like cells, cholangiocyte-like cells, endothelial progenitor cells, endothelial-like cells, hemogenic endothelial cells, erythrocyte-like cells, hematopoietic progenitor-like cells, mesenchymal progenitor cells, stellate-like cells, neurectodermal cells, neural plate-like cells, neural fold-like cells, and any combination thereof.

A "somatic cell" refers to a biological cell forming the body of an organism. In a human, a somatic cell is any cell other than a gamete, germ cell, gametocyte or undifferentiated stem cell. Methods of isolating somatic cells from humans are known in the art, any of which may be used herein.

Likewise, methods of producing hiPS cells (e.g., reprogramming somatic cells to a pluripotent state) are known in the art, any of which may be used herein. For example, induced pluripotent cells can be reprogrammed from human somatic cells by inducing in the somatic cells expression of four factors, including OCT4, SOX2, NANOG and L/N28[31]. Induced pluripotent cells can also be reprogrammed from fibroblast cells by inducing in the somatic cells expression of OCT3/4, SOX2, KLF4 and c-MYC[32,33]. Other methods of producing hiPS cells are also contemplated herein.

In some embodiments, heterogeneous tissue produced from hiPS cells that overexpress a gene encoding GATA6, GATA4 or SOX17 protein may be banked (e.g., protected and stored) for use at a later time.

In some embodiments, the heterogeneous tissue produced, or cells isolated from the tissue, are transplanted into the human from whom the somatic cells were isolated.

Also contemplated herein are methods and assays for assessing the toxic effects of an agent on a heterogeneous tissue. For example, heterogeneous tissue of the present disclosure may be used in assays (e.g., high-throughput assays) for identifying harmful agents (e.g., hazardous chemicals such as teratogens)[40,41]. In some embodiments, heterogeneous tissue may be used to recapitulate human physiology "in a dish." Such assays reduce the overall reliance on animal studies for predicting the risk of toxic responses in humans. Thus, in some embodiments, methods of the present disclosure include culturing an agent (e.g., an agent suspected of being harmful to humans) in the presence of a heterogeneous tissue, and assessing toxic effects of the agent on the heterogeneous tissue. In some embodiments, the heterogeneous tissue is assessed for changes in cell death, growth, proliferation, differentiation, presence or absence of biomarkers, and general "health" of the tissue. In some embodiments, teratogenicity of the agent is assessed.

Other aspects of the present disclosure contemplate methods and assays for assessing the effects of agents on metabolic activity in a heterogeneous tissue. In some embodiments, heterogeneous tissues provided herein may be used, for example, to model metabolic disorders such as, for example, liver disease[42,43]. Such assays may be used, in some embodiments, to recapitulate pathological features of diseases that affect humans (e.g., humans from whom the hiPS cells are derived). Thus, in some embodiments, methods of the present disclosure include culturing an agent in the presence of a heterogeneous tissue of the present disclosure, and assessing metabolic activity of the tissue. These assays may be used, for example, to test the efficacy and/or adverse effects of certain treatments (e.g., drug therapies) on patient-specific heterogeneous tissue (e.g., tissue produced from hiPS cells derived from the patient).

As used herein, an agent is any atom or molecule or compound. The agent may be without limitation a protein, a polypeptide, a peptide, a nucleic acid, a virus-like particle, a steroid, a proteoglycan, a lipid, a carbohydrate, and analogs, derivatives, mixtures, fusions, combinations or conjugates thereof, a pharmaceutical drug (e.g., small molecule drug), chemical (e.g., industrial chemical) or other small molecule. The agent may be a prodrug that is metabolized and thus converted in vivo to its active (and/or stable) form.

An agent may be naturally occurring or non-naturally occurring. Naturally occurring agents include those capable of being synthesized by a human. Non-naturally occurring are those that do not exist in nature normally, whether produced by plant, animal, microbe or other living organism. One class of agents is peptide-based agents such as (single or multi-chain) proteins and peptides. Examples include antibodies, single chain antibodies, antibody fragments, enzymes, co-factors, receptors, ligands, transcription factors and other regulatory factors, some antigens (as discussed below), cytokines, and chemokines. These peptide-based agents may or may not be naturally occurring. Another class of agents includes those agents that are not peptide-based and which could not be synthesized by a human. Examples include chemical compounds that are non-naturally occurring, or chemical compounds that are not naturally synthesized by mammalian (and in particular human) cells.

A variety of agents used for therapeutic or diagnostic purposes can be assessed as provided herein and include, without limitation, imaging agents, immunomodulatory agents such as immunostimulatory agents and immunoinhibitory agents, antigens, adjuvants, cytokines, chemokines, anti-cancer agents, anti-infective agents, nucleic acids, antibodies or fragments thereof, fusion proteins such as cytokine-antibody fusion proteins, and Fc-fusion proteins.

EXAMPLES

Example 1

The following experiments show that GATA6 induces exit of a pluripotent cell state in a similar fashion to intracellular matrix (ICM) segregation in a blastocyst and also generates different cell types depending on the expression levels and tissue context. Cell lines were generated by means of lentiviral gene delivery. The cell lines ectopically expressed GATA6 upon addition of the small inducer molecule, Doxycycline (Dox) (FIG. 1, Y: Rock-inhibitor; Dox: Doxycycline; PP-Med.: pluripotency-supporting medium (e.g., mTeSR-1, Stem Cell Technologies, Vancouver); Basal medium: medium without additional growth factors or serum (e.g., APEL, Stem Cell Technologies, Vancouver, or IMDM); filled arrows: RNA isolation and microarray analysis from total cells; open arrows: RNA isolation and microarray analysis from enriched cells (CXCR4, CD34: enrichment using MACS® MicroBead Technology; picking: manual extraction)).

Figures 1, 11A:
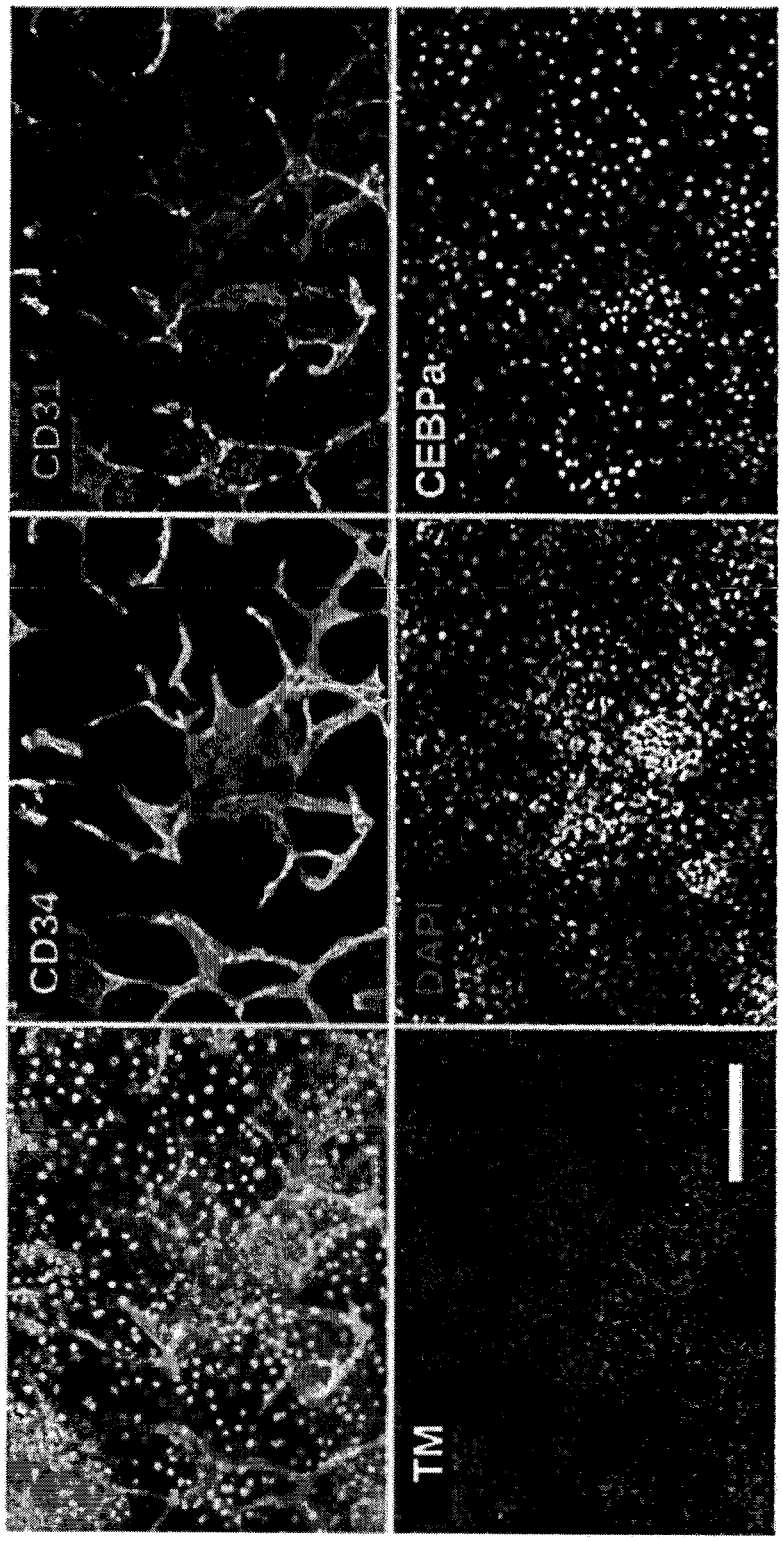
FIGS. 11A-11C show the generation of liver-like tissue in multiple hiPS cell lines (e.g., PGP1, PGP5, PGP9 and C1).
Figures 2, 11A:
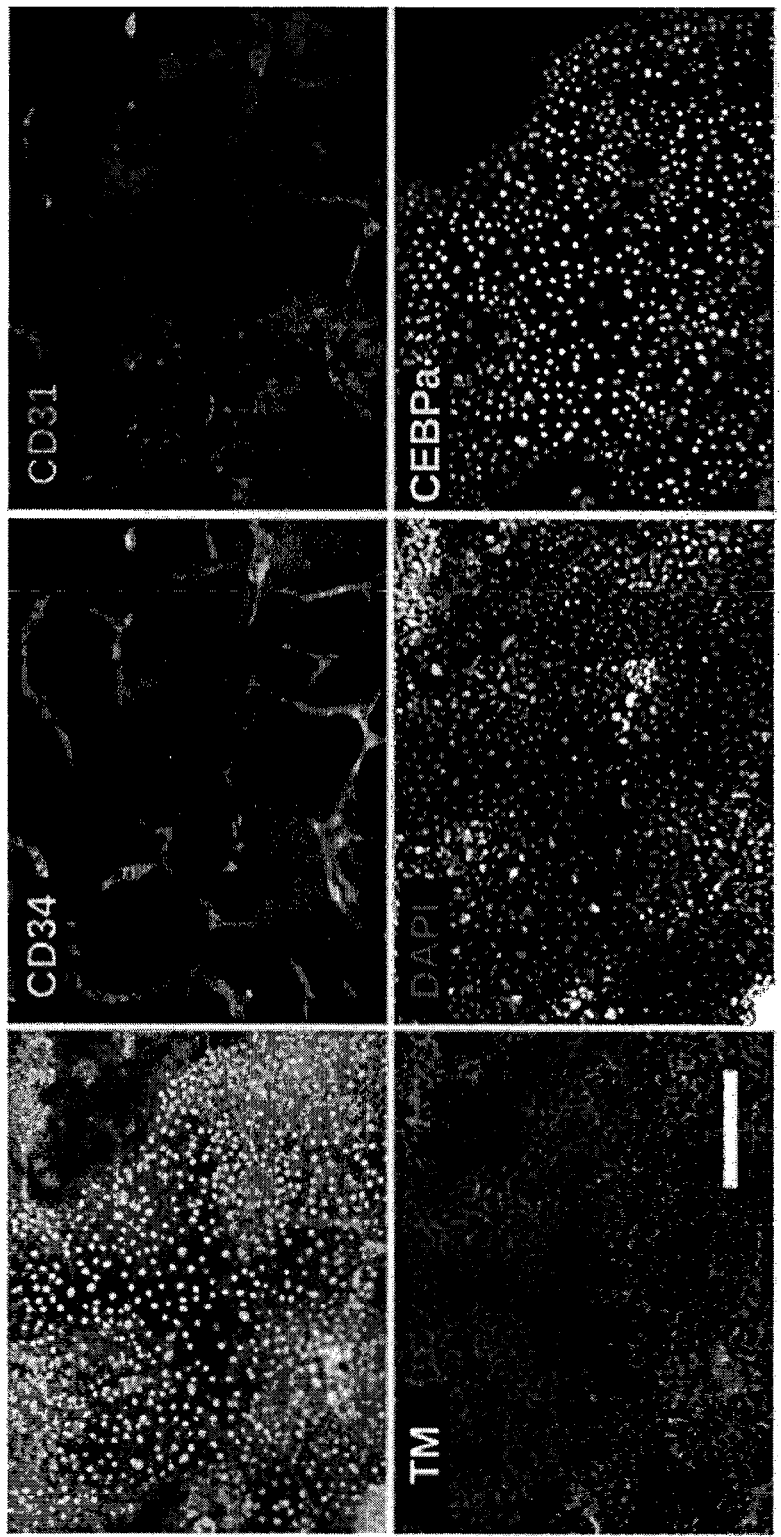
Figures 3, 11A:
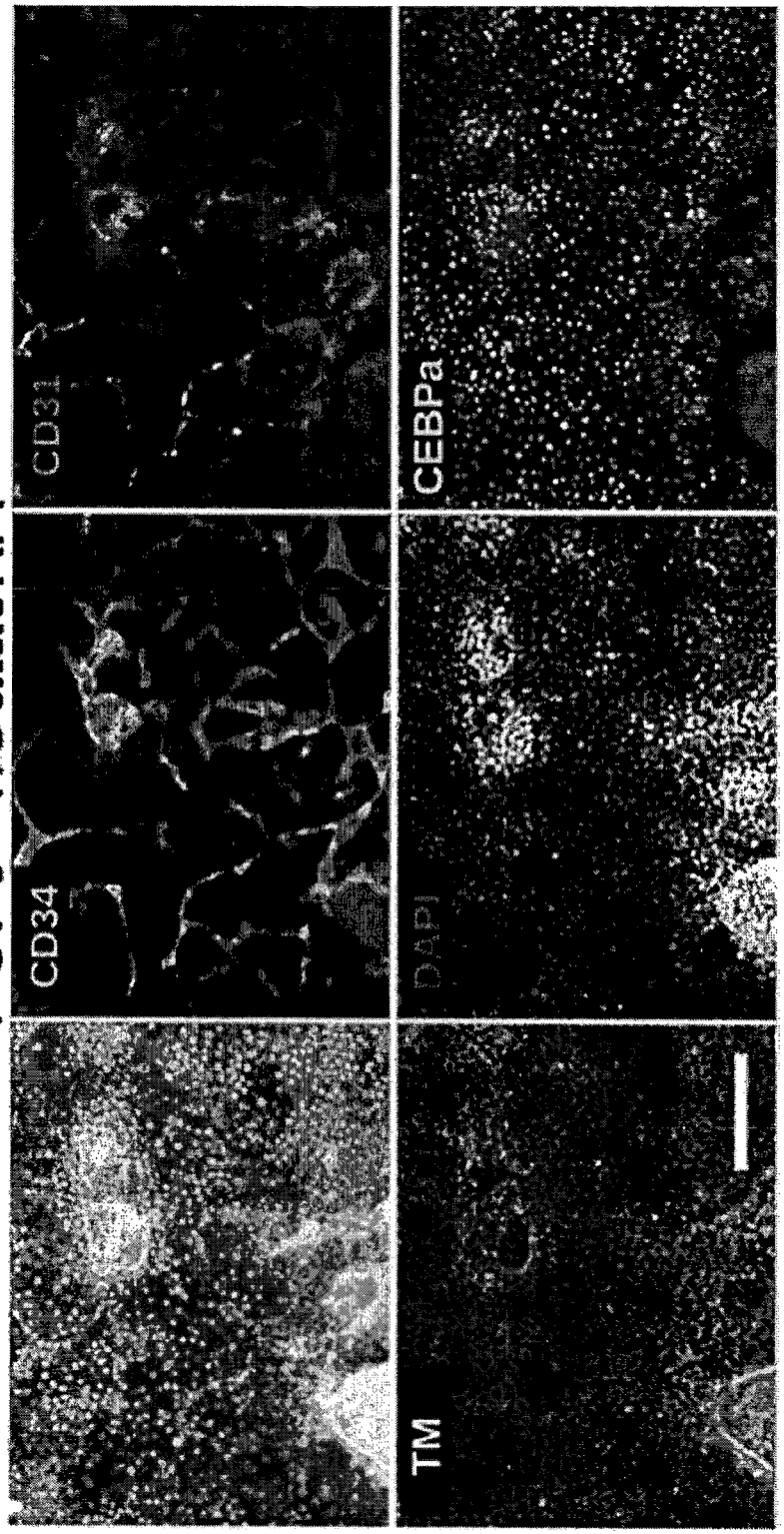
Figures 4, 11A:
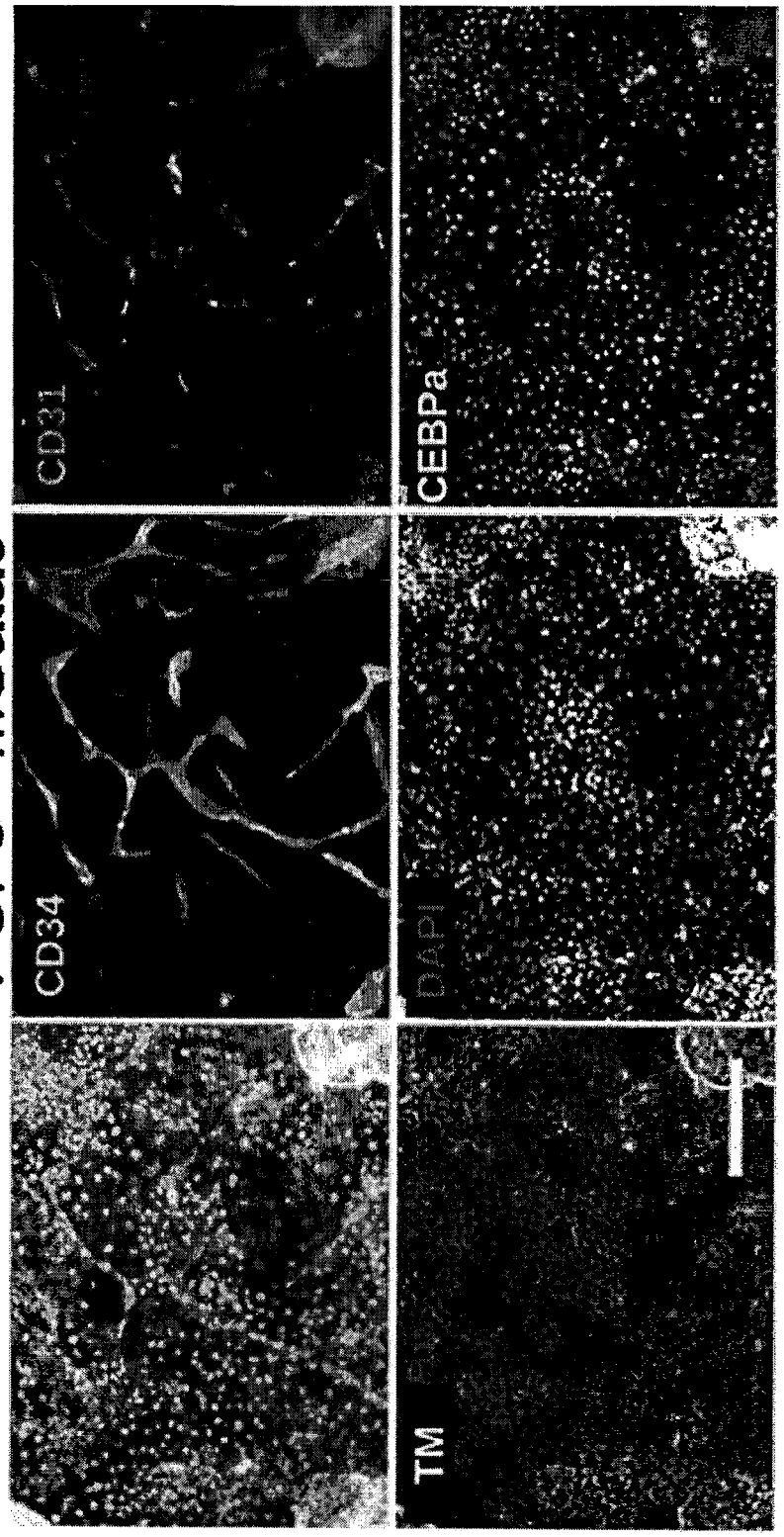
Figures 5, 11A:
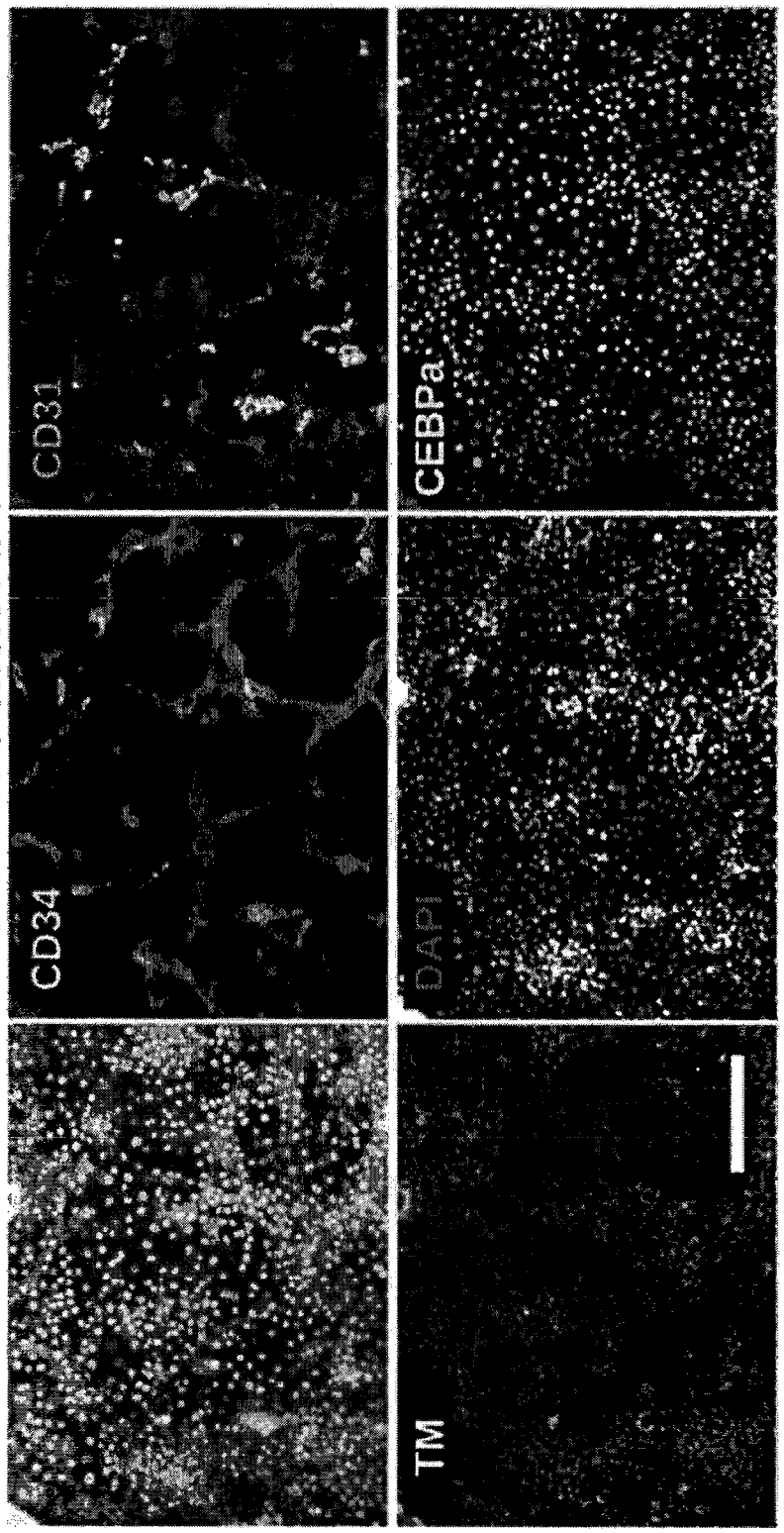
Figures 6, 11A:
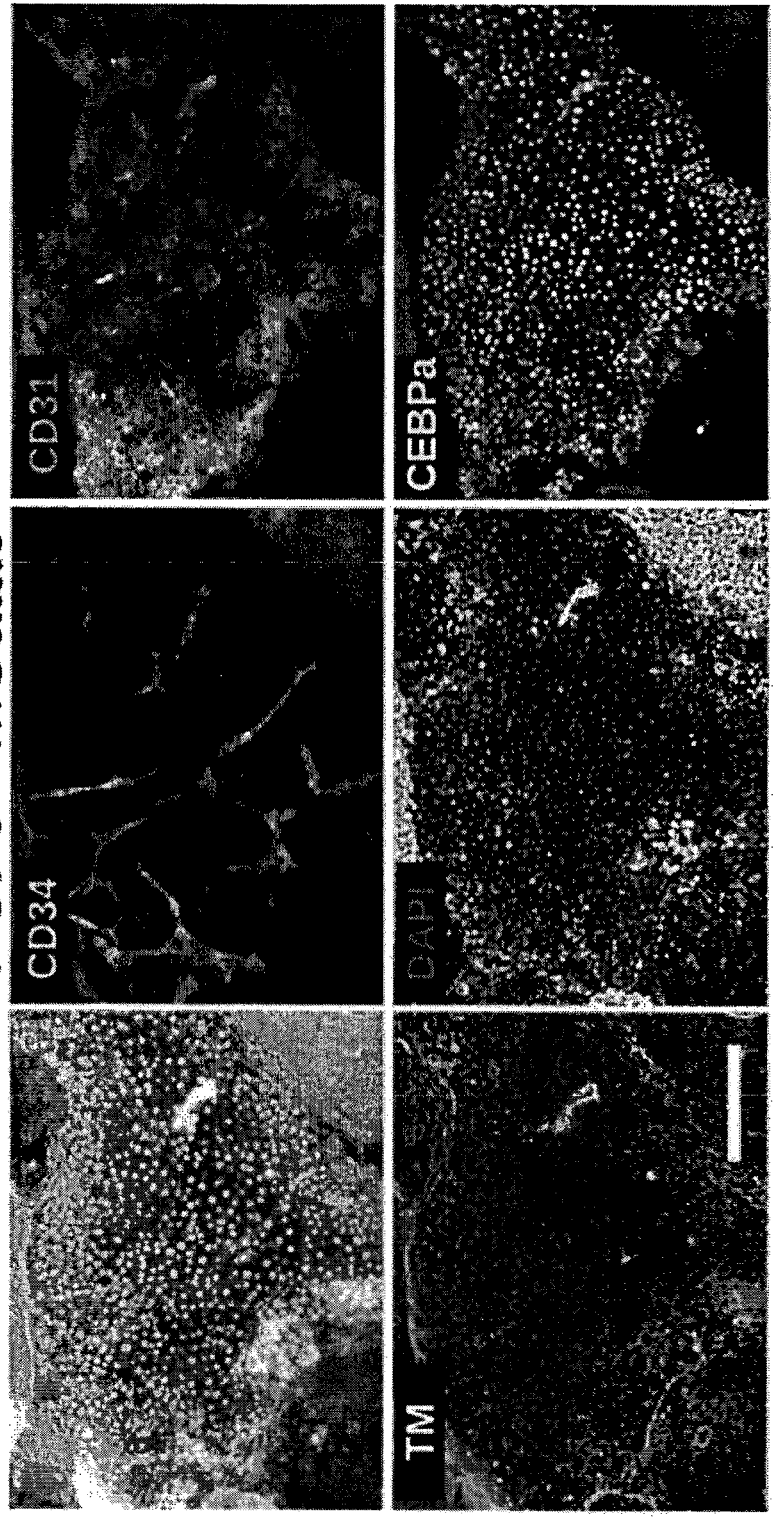

Rapid expression of a range of ectopic GATA6 levels was observed in cultured cells, and cultured cells segregated into an epithelial GATA6+ endodermal sub-population and compact clusters of an OCT4+/NANOG+ pluripotent sub-population (FIGS. 2A-2C, and FIGS. 5A-5C). Similar cell population segregation took place when Gata6 was co-translationally coupled to a puromycin (GATA6-2A-puromycin) resistance marker and the population was selected for resistant cells (FIGS. 5A-5C), indicating that while low GATA6-2A-puromycin expression was sufficient to confer cell resistance to the antibiotic, it was not sufficient to induce differentiation. In cell lines expressing GATA6-2A-EGFP or HA epitope-tagged GATA6 (GATA6-HA), EGFP or GATA6-HA were readily detectable in the endodermal fraction as well as in the pluripotent sub-population, albeit at lower levels (FIG. 2B, FIGS. 5A-5C). In a separate experiment that included two engineered hiPS cell lines, one with inducible GATA6 transgene and one without inducible GATA6 transgene, cells without an inducible GATA6 transgene translocated to the pluripotent clusters (FIGS. 6A-6B). These observations suggest two competing mechanisms in action: induction of an endodermal phenotype as a function of GATA6 expression levels coupled with location-dependent suppression of the endodermal phenotype. Cells expressing high levels of GATA6 localized to the endodermal sub-population and acquired an endodermal phenotype. Cells expressing low levels of GATA6 acquired an endodermal phenotype if they were located within the endoderm sub-population, but were kept from acquiring an endodermal fate if they were located within a pluripotent population (FIG. 2C, FIGS. 7A-7D).

Figure 7A:
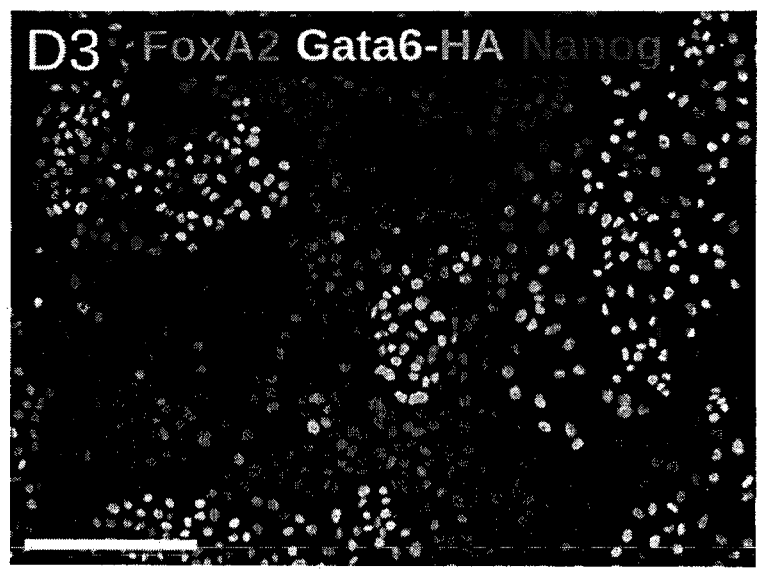
Figure 7B:
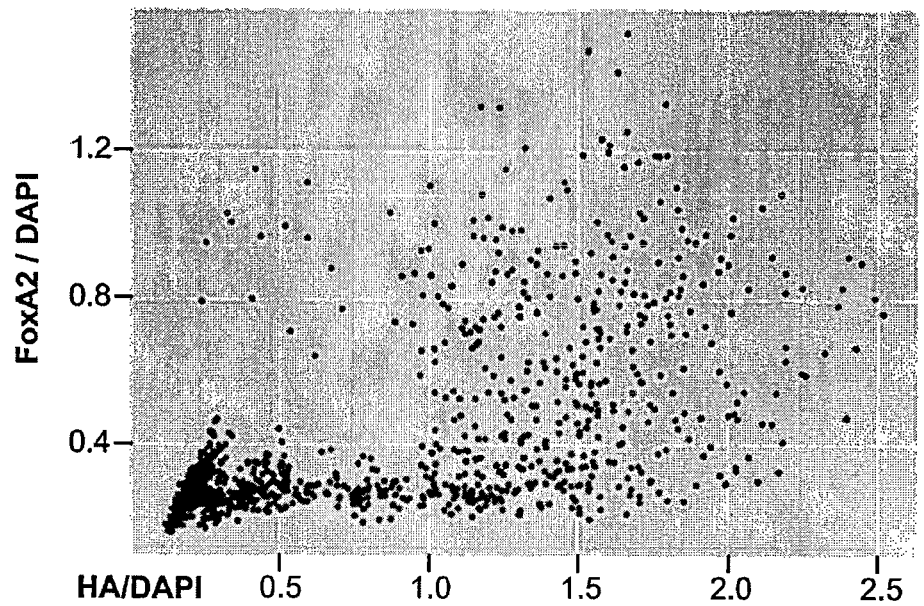
Figure 7D:
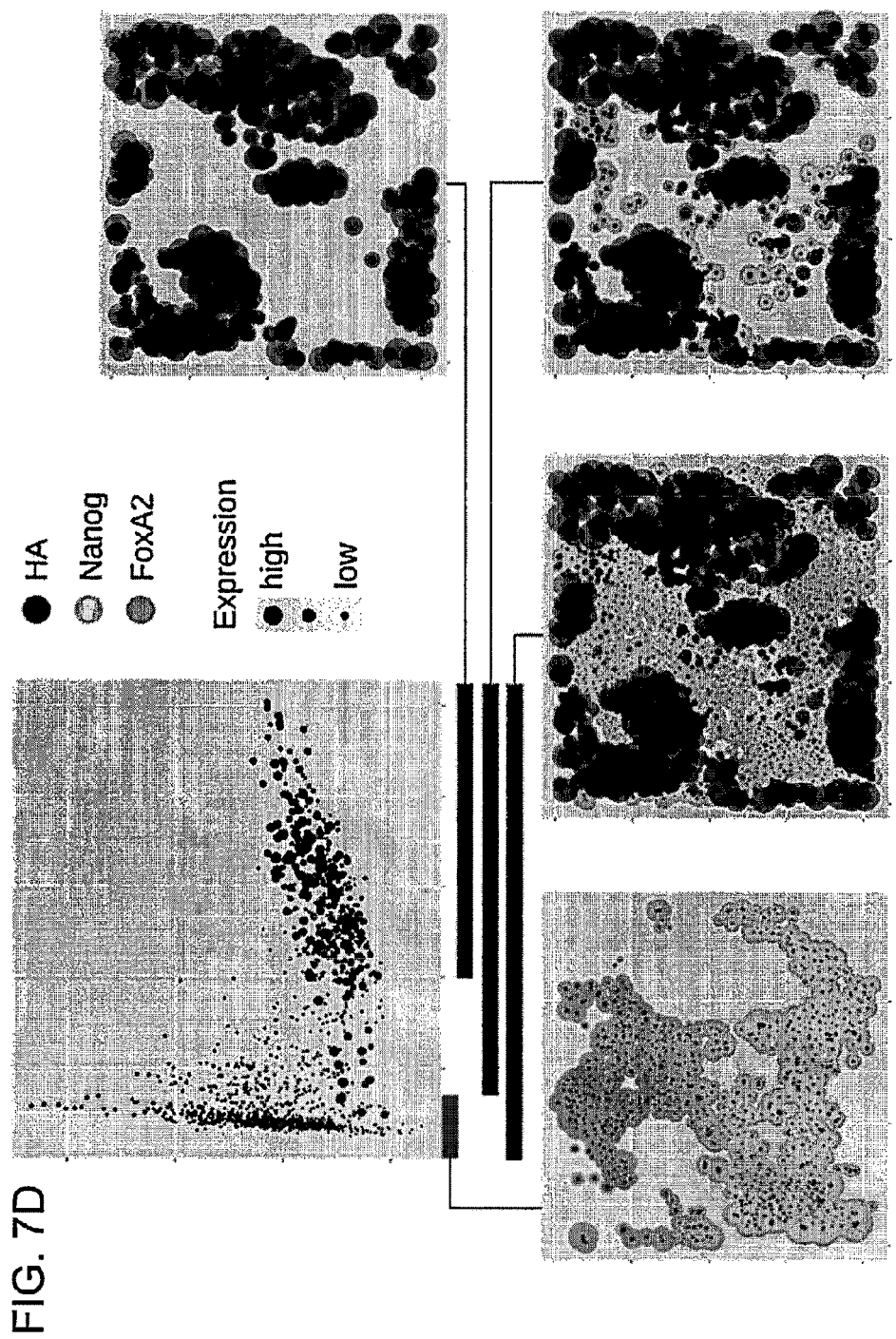
Figure 8C:
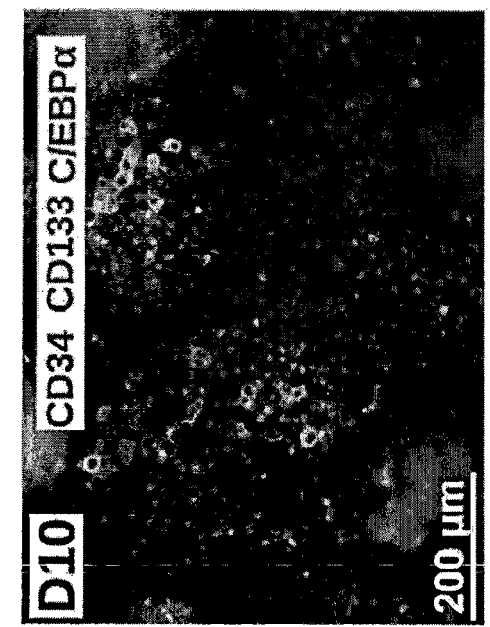
Figure 8D:
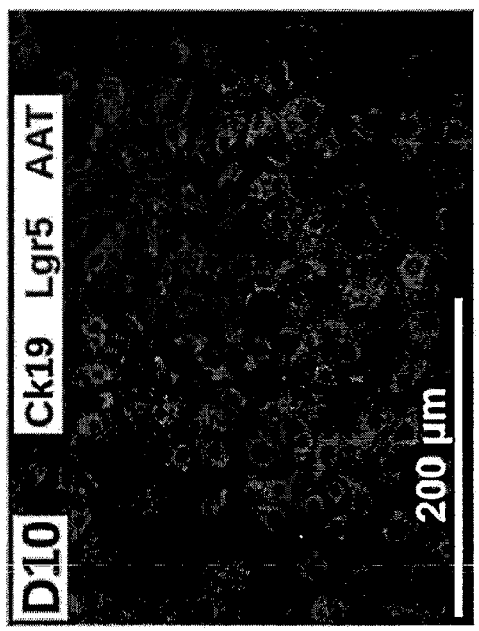
Figure 8E:
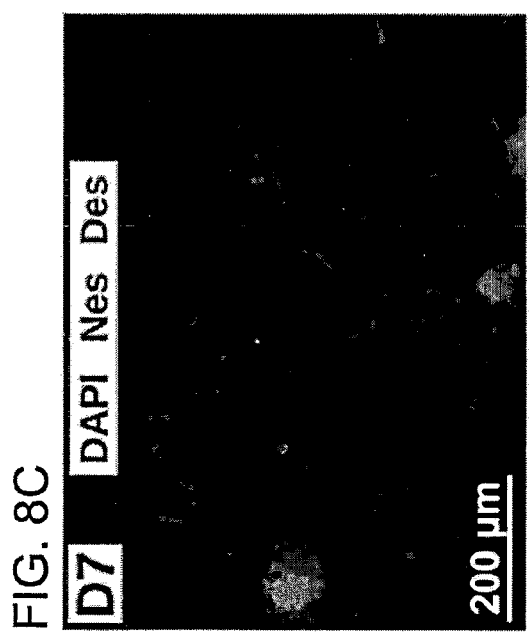
Figure 8F:
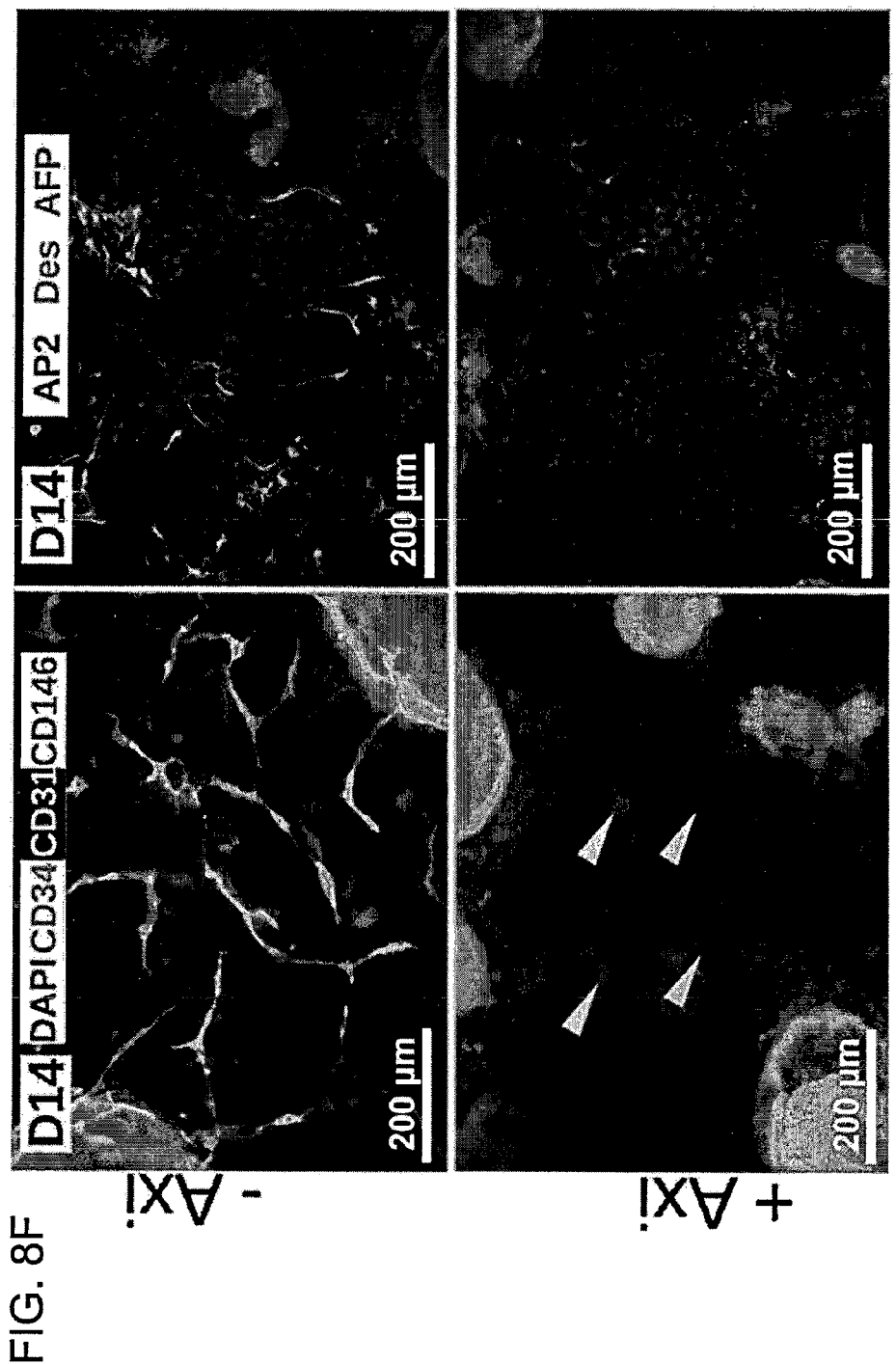
FIG. 8F shows that Axitinib (Axi) abolishes the emergence of endothelial-like CD34+ cells, but not endodermal-like CD34+ cells. Reduced numbers of Des+ stellate-like cells were observed in Axitinib-treated cells.

Cells expressing endoderm biomarkers SOX17 and FOXA2 appeared at day 1-2 (FIGS. 1B and 1C, FIGS. 5A-5C, and FIGS. 6A-6B). The feasibility of further engineering the sub-populations was demonstrated by starting with multiple modified cell populations and varying the Dox concentration (FIG. 6A), yielding variable expression patterns and numbers for the endoderm cells. A sharp transition in a scatter plot of GATA6-HA versus FOXA2 expression suggested that GATA6 expression must reach a defined threshold for FOXA2 to be expressed (FIG. 7B). The mesoderm/gastrulation marker Brachyury (T) was expressed within two days (FIG. 2B). To further characterize specific sub-populations within this system, additional surface markers were identified, permitting cell isolation and downstream analysis. Cells positive for the surface marker CXCR4 appeared on day 2, and they were distributed in the endoderm-like population co-localizing with the GATA6-expressing cells (FIG. 2D). While CXCR4 has previously been associated with definitive endoderm and is still being used in many studies for this purpose, it is also expressed at the surface of other cell types (visceral endoderm in mice, mesendoderm, trophoblasts)[19,20]. Species-specific divergences in early development may also explain, to some extent, the discrepancy in the literature[21]. In the present system, CXCR4$^+$ cells exhibited a high degree of motility and migrated to the leading edges of the endoderm layer (FIGS. 6A-6B). CXCR4$^+$ cells were isolated on day 5 using MACS beads (Miltenyi Biotech) and transcriptional profiling was performed using exome microarrays. Markers enriched in day 5 CXCR4$^+$ cells encompassed primitive streak, mesendoderm, definitive endoderm, foregut and initial markers of hepatic endoderm (FIG. 2D, FIGS. 7A-7D). Without being bound by theory, this profile might represent asynchronously developing sub-populations, and the presence of some primitive or visceral endoderm cells cannot be excluded. Markers depleted in the day 5 CXCR4$^+$ sub-population included CXCL12/SDF-1, the ligand binding the CXCR4 receptor as well as FGF2, FGF4, HGF, indicating that these important factors for hepatoblast specification and expansion were provided by the CXCR4$^-$ fraction.

Figure 3B:
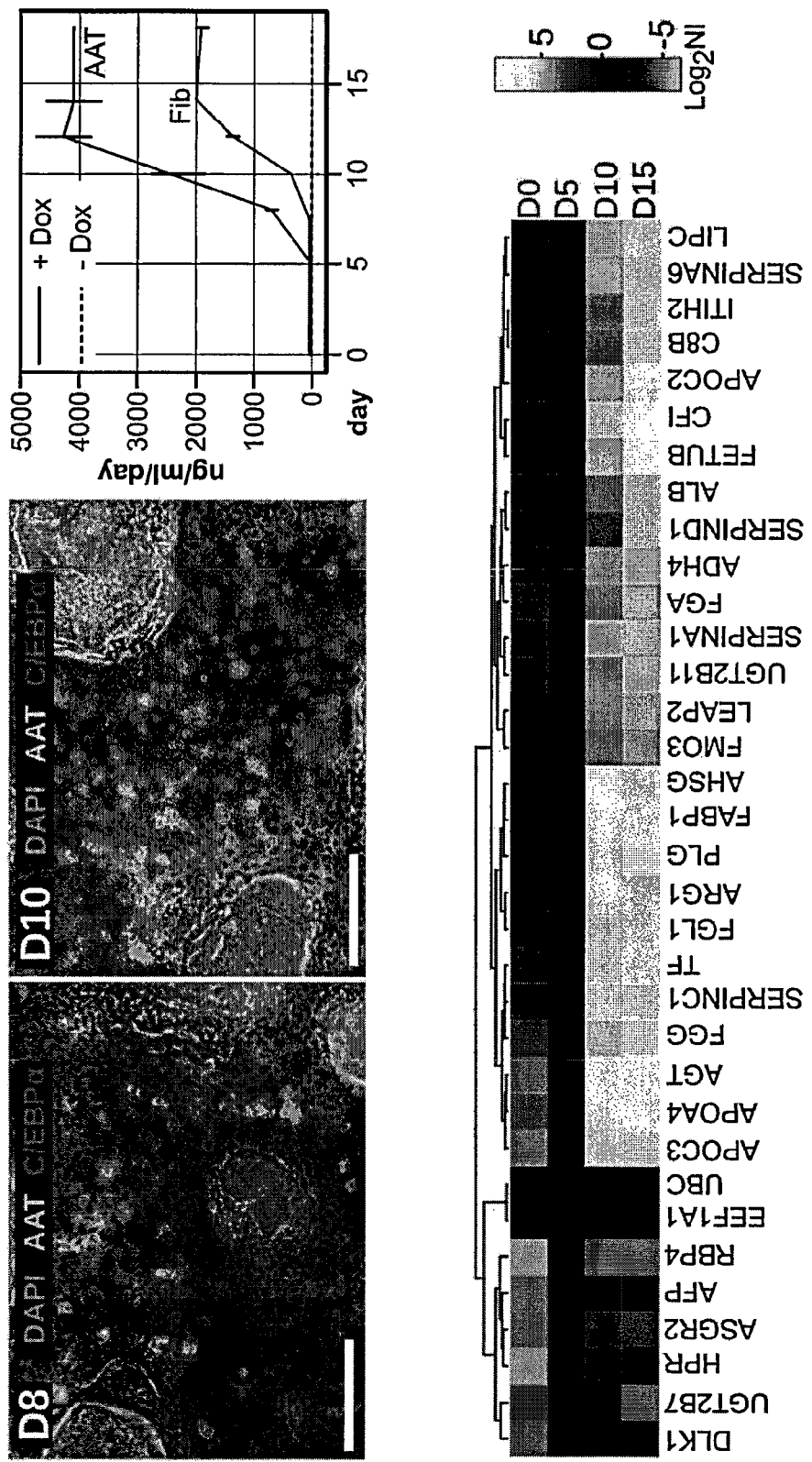
FIG. 3B shows maturation of hepatic endoderm at day 8 (left panel) and day 10 (middle panel), evidenced by upregulation of AAT and Fibrinogen (Fib) synthesis (right panel). Heatmap below: upregulation of hepatic genes in between day 5 and 10. (UBC and EEF1A1 were used as control/housekeeping genes). Scale bar: 200 µm.
Figure 4B:
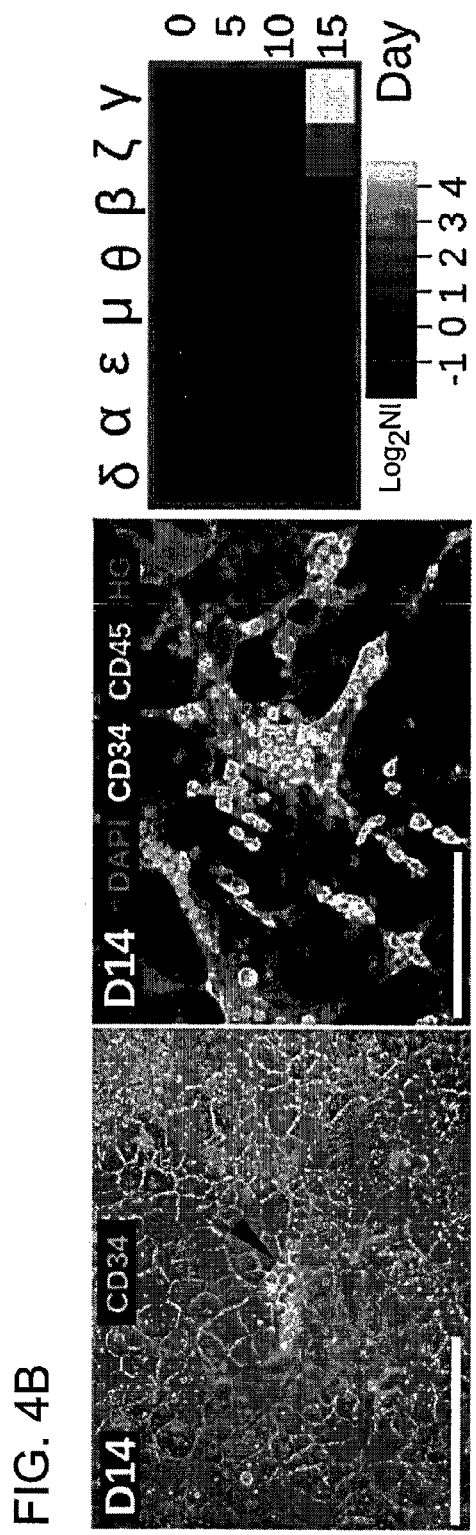
FIG. 4B, left panel, shows hematopoietic processes developed within the liver-like tissue at day 14 (black arrow: endothelial-like tube embedded in hepatoblast-like tissue and filled with CD34+ cells). Middle panel: shows immunostaining for CD34$^+$ cells, CD45$^+$ cells and HG$^+$ cells (pan-hemoglobin) at day 14. Right panel: microarray analysis showed hemoglobin gamma expression is strongly upregulated, particularly at day 15. Scale bar: 200 µm.
Figure 5B:
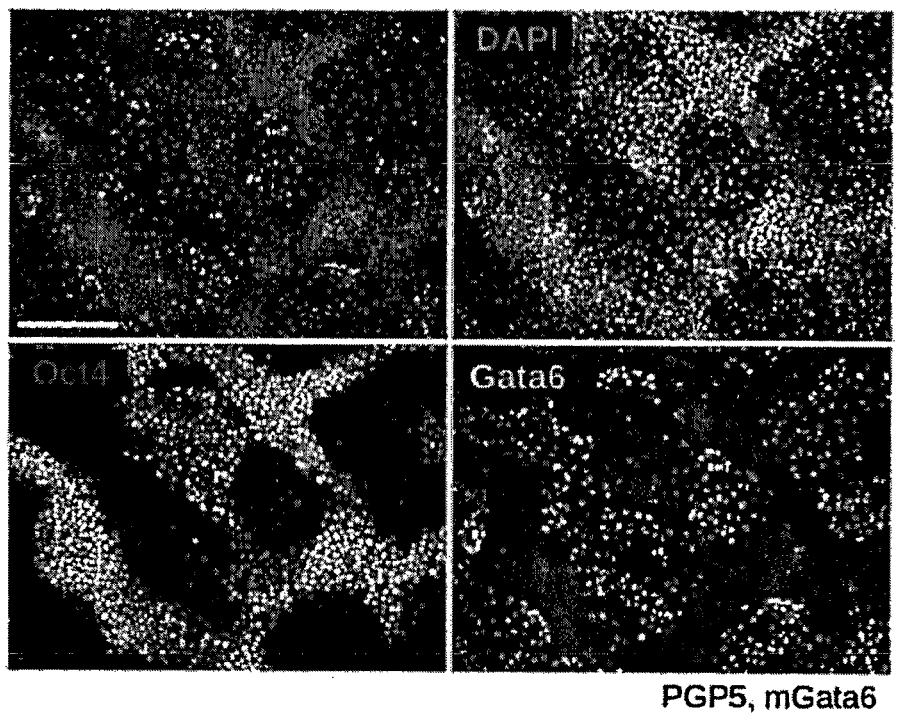
Figure 5C:
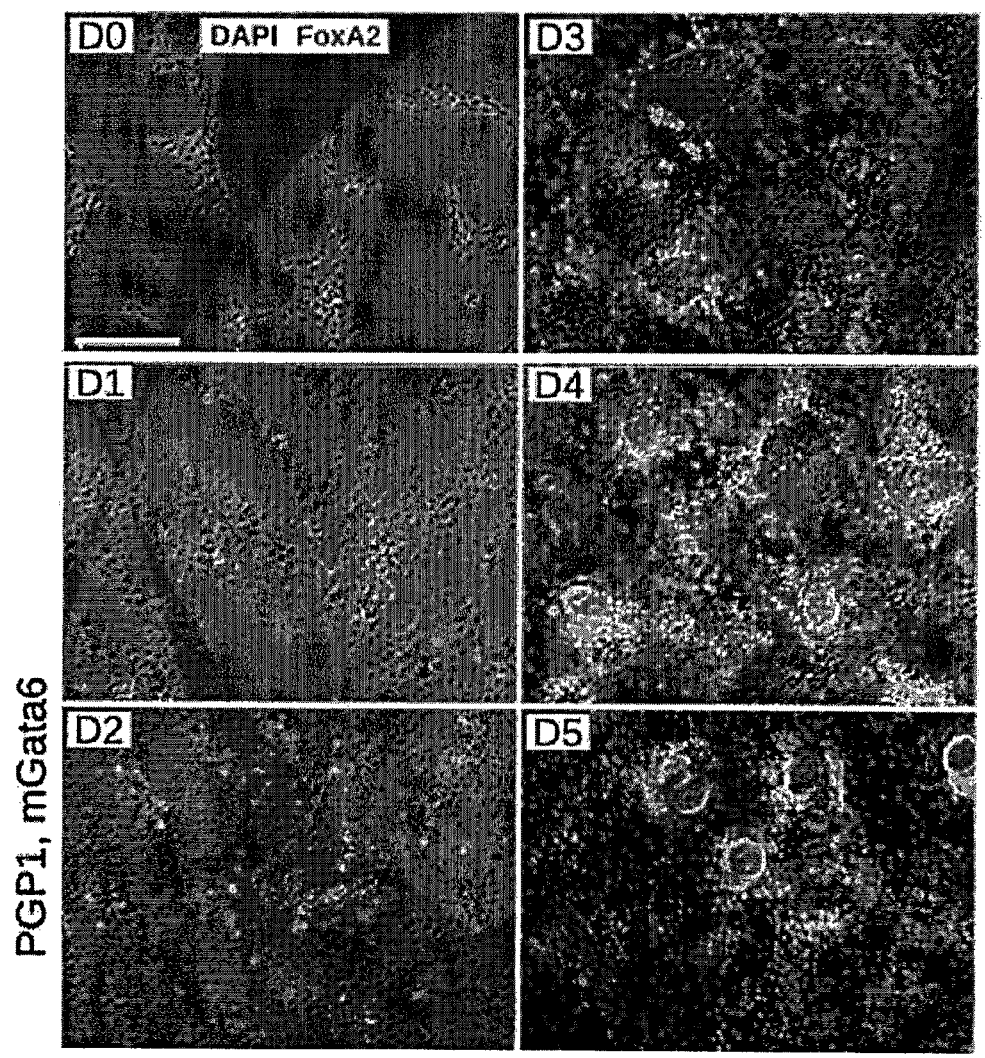
Figure 9:
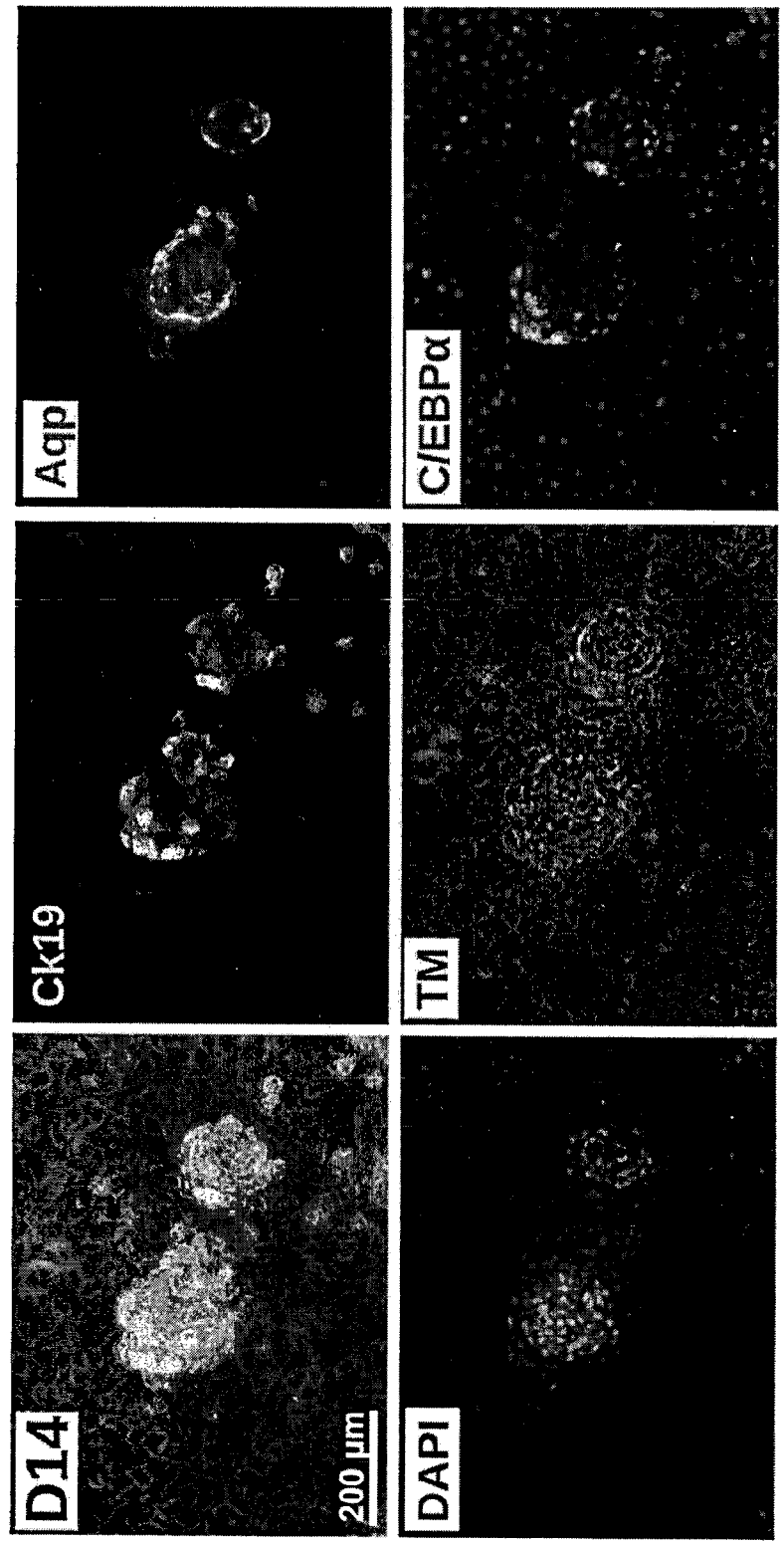
FIG. 9 shows cholangiocyte-like cells developing within the hepatoblast layer. Immunostaining for CK19, aquaporin (AQP), CEBPA and DAPI on day 14 in cells of the PGP1 cell line.
Figure 11B:
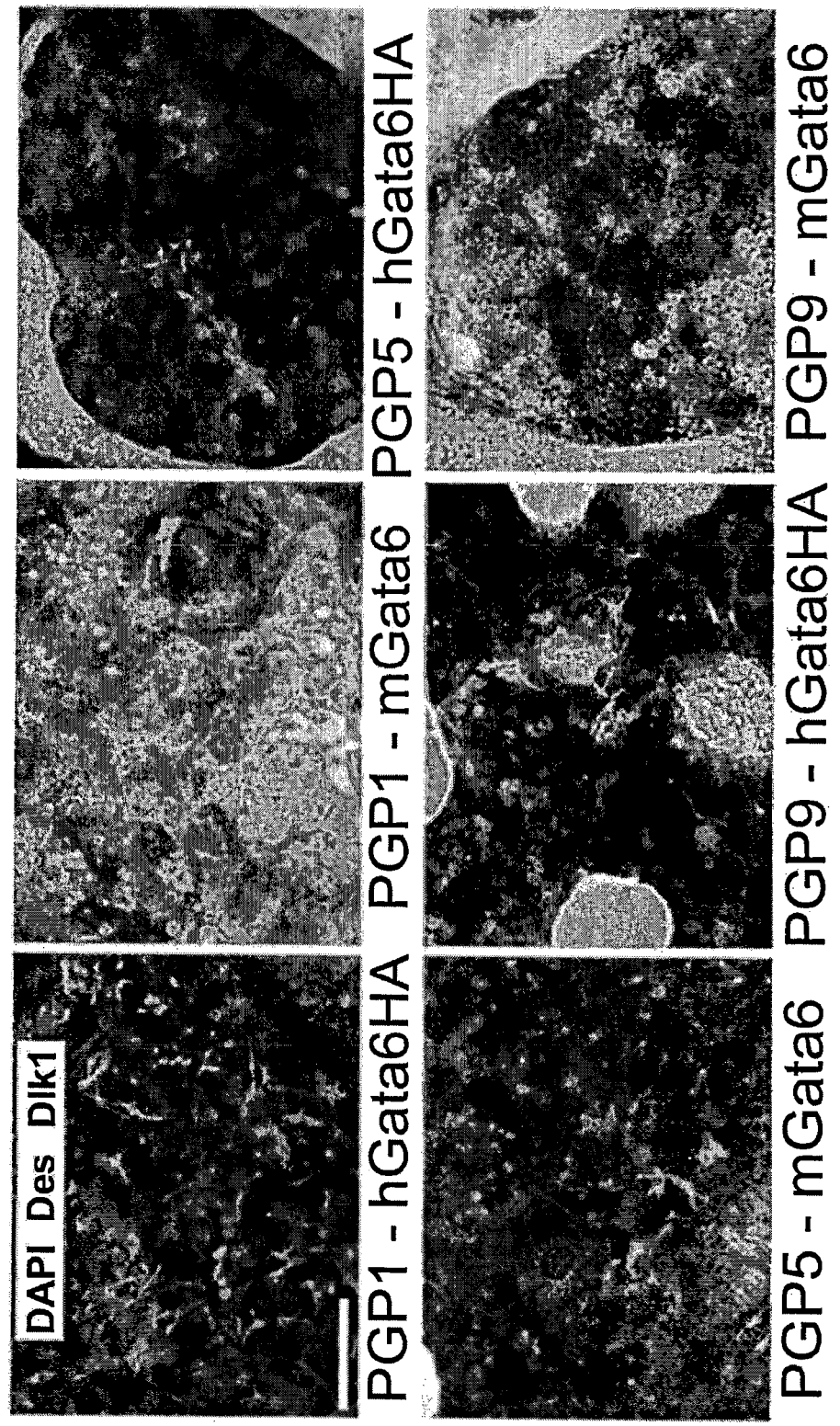
Figure 11C:
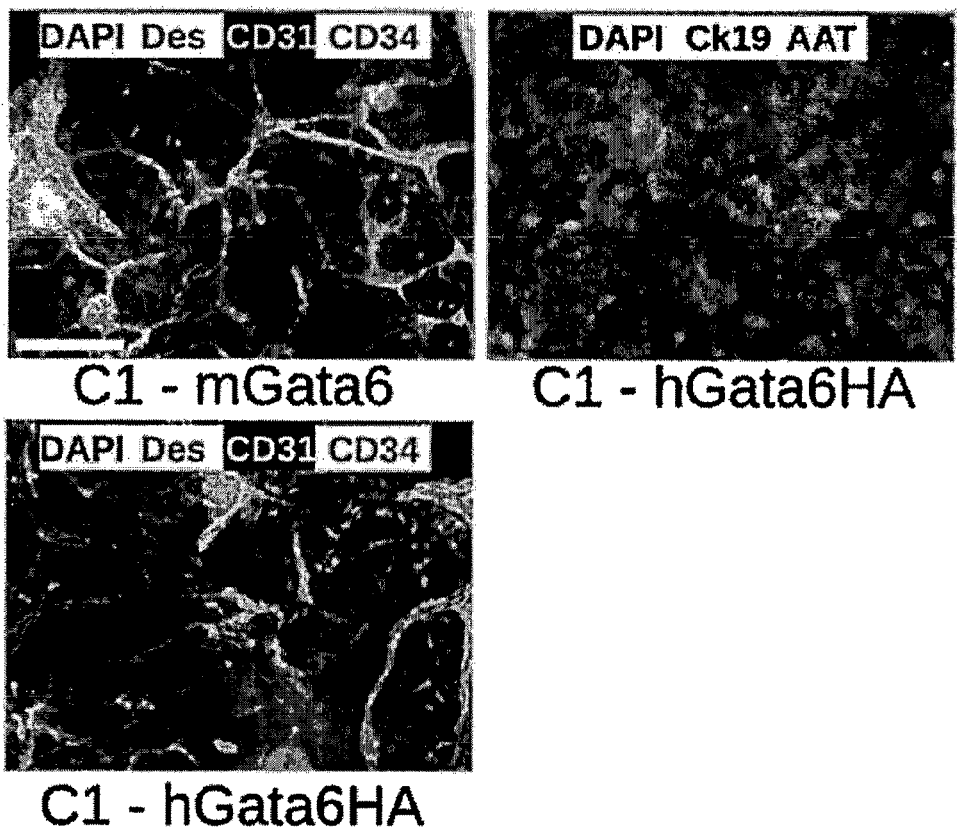
Figures 2, 13B:
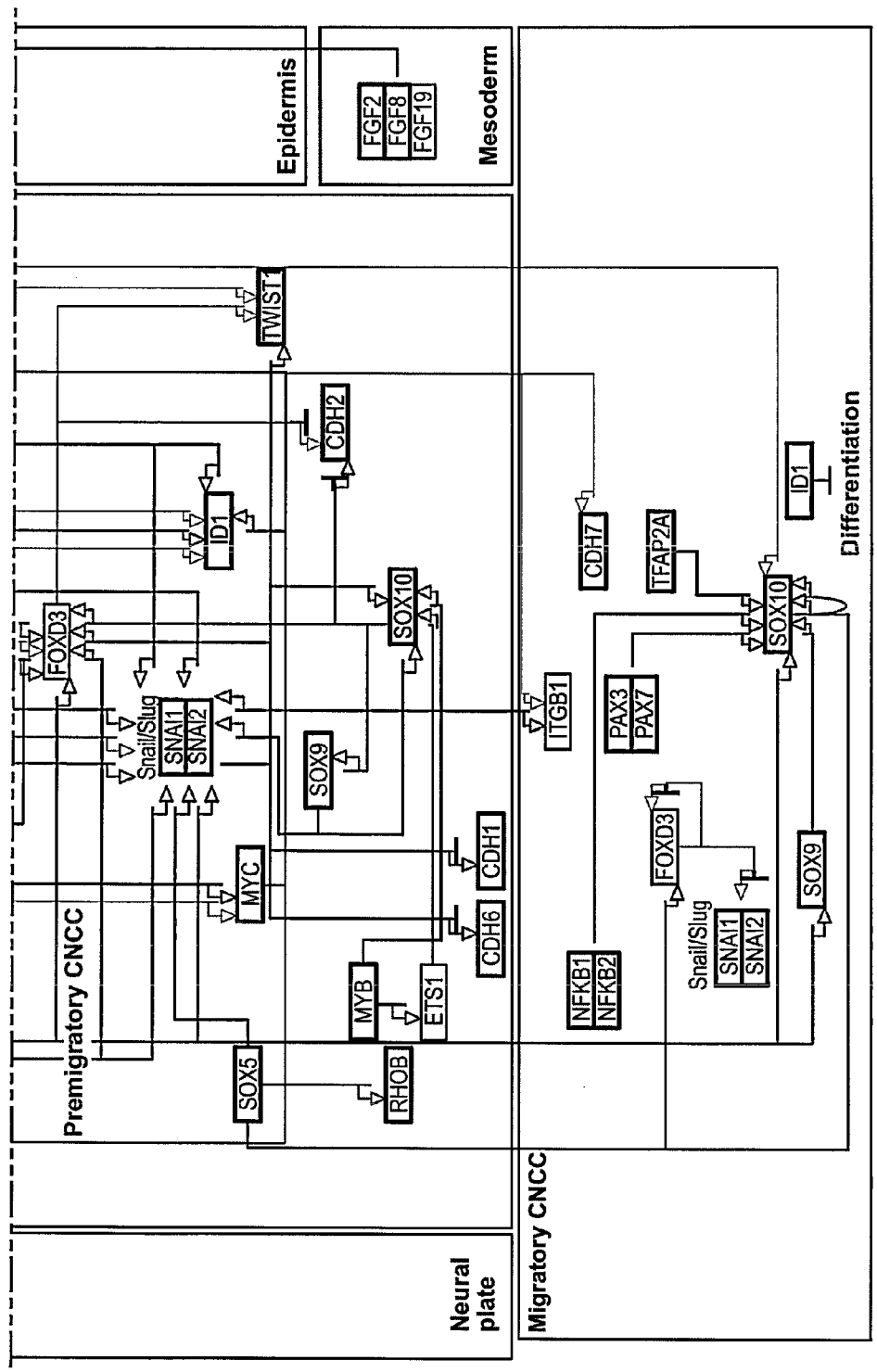
Figure 14A:
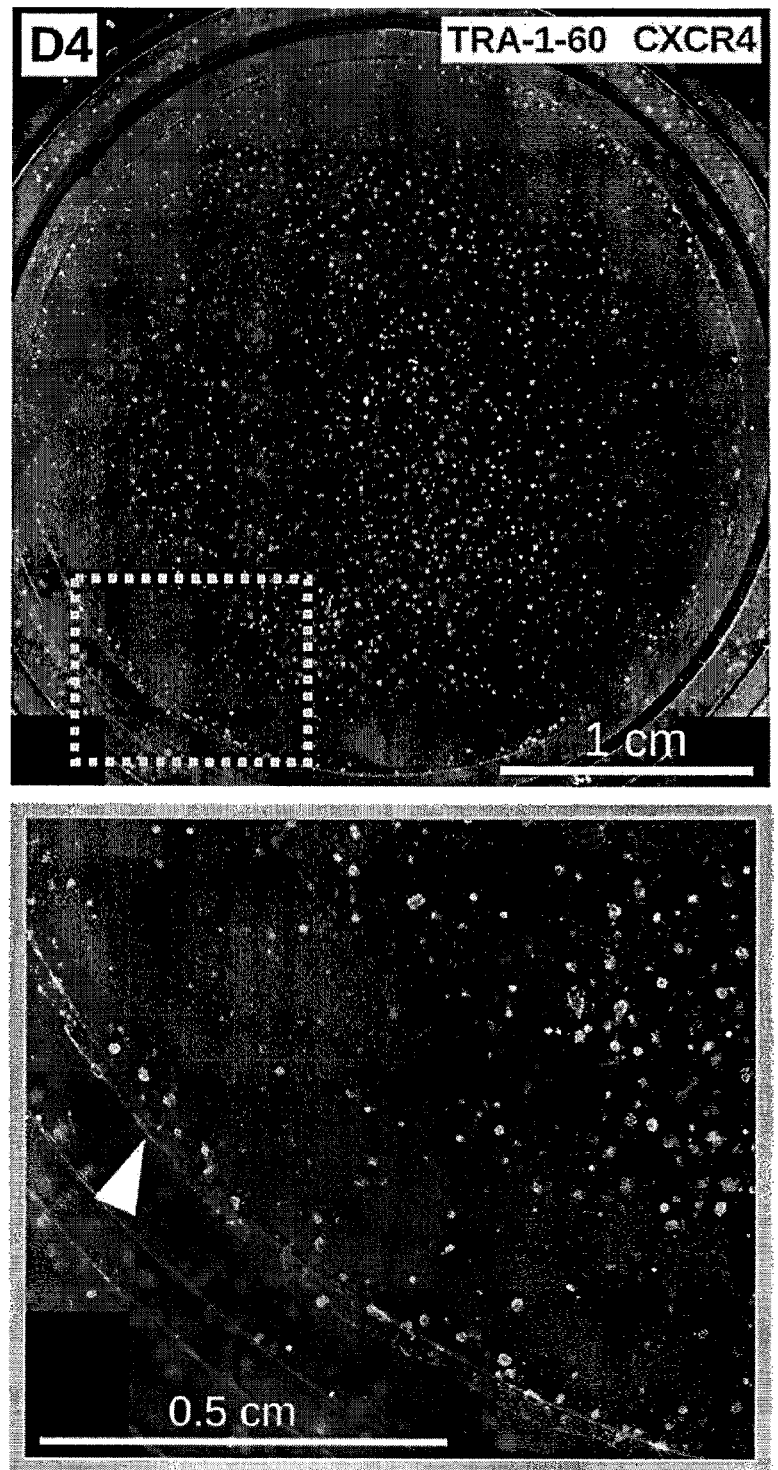
FIGS. 14A-14B show Gata6-induced CXCR4+ endoderm.
Figure 14B:
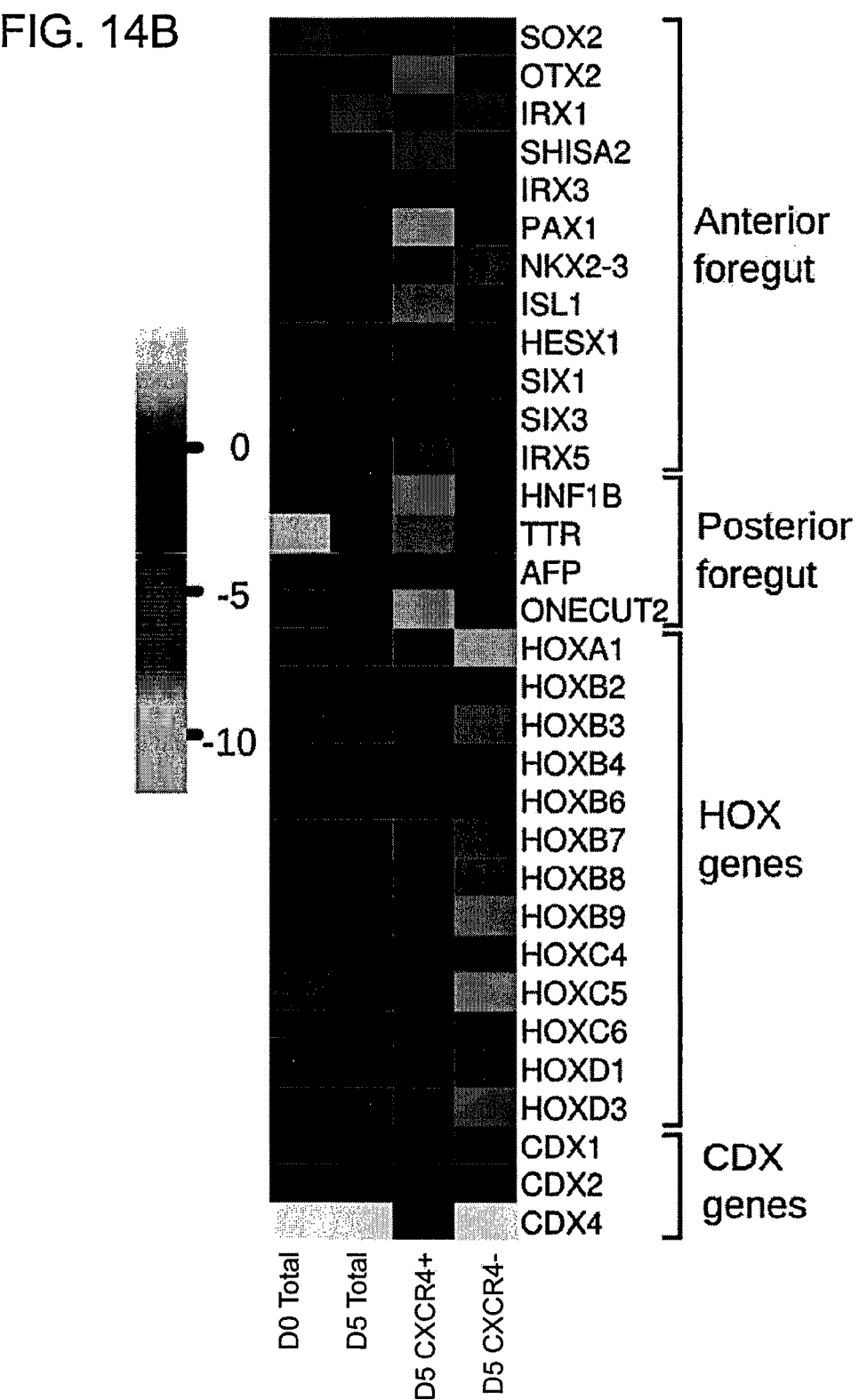
Figure 15A:
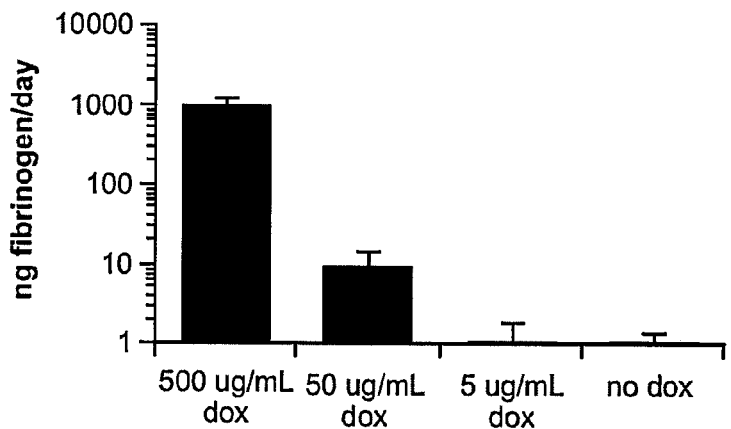
FIGS. 15A-15D show that fibrinogen production, a marker of hepatocyte differentiation, varied with Dox concentration and ratio of wild type (WT) to modified cells expressing GATA6 engineered cells.
Figure 15B:
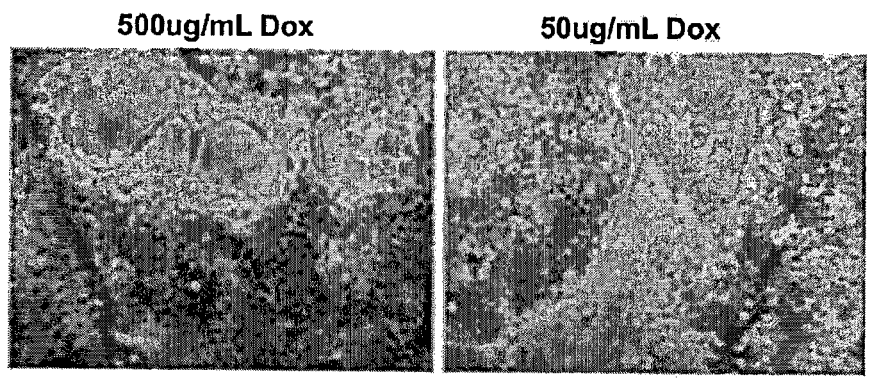
Figure 15C:
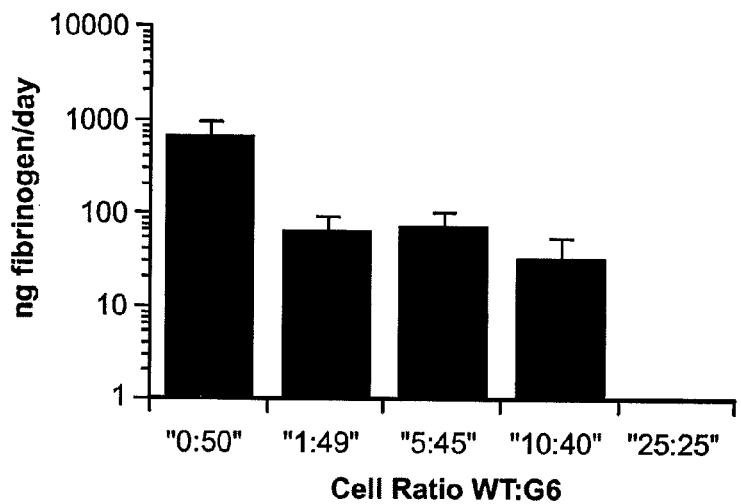
Figure 15D:
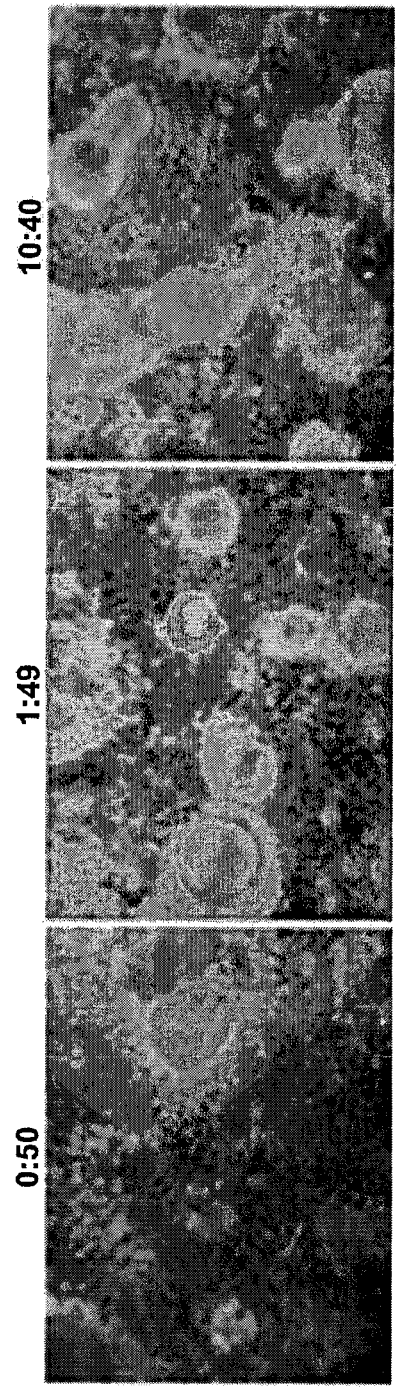
Figure 16A:
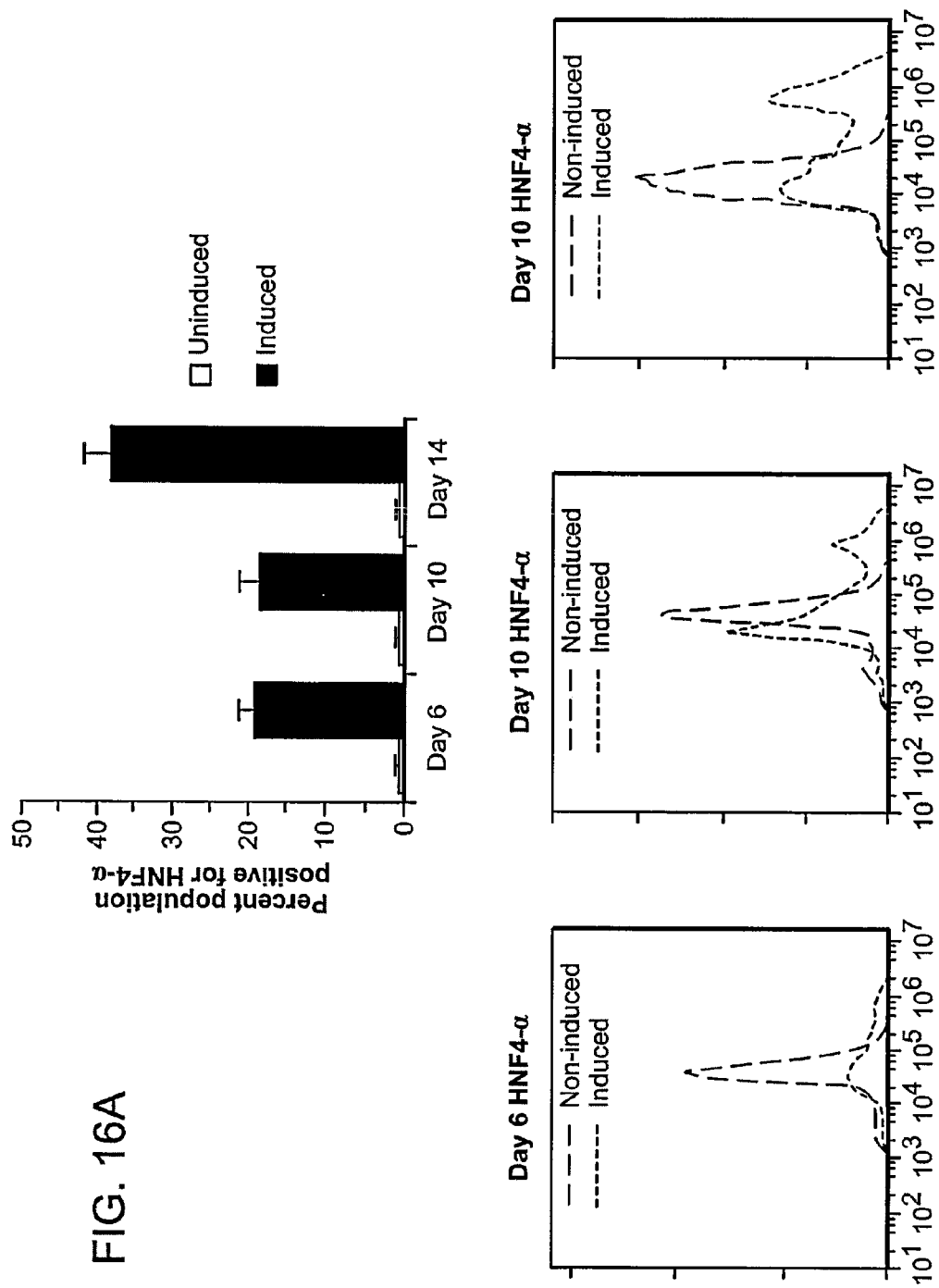
FIGS. 16A-16C show alpha-1 antitrypsin (AAT) and fibrinogen quantification for days 6, 10, and 14 of culture.
Figure 16B:
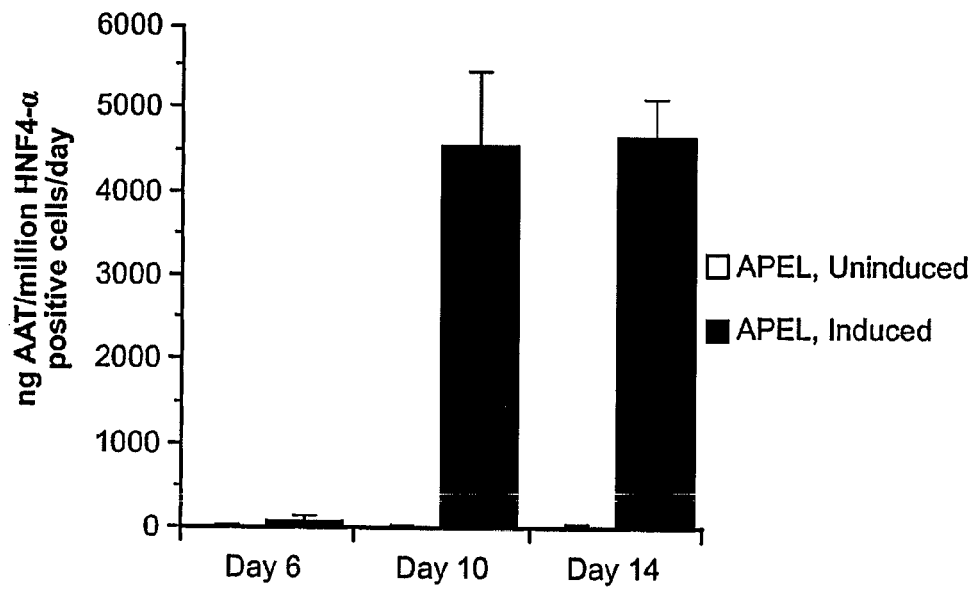
Figure 16C:
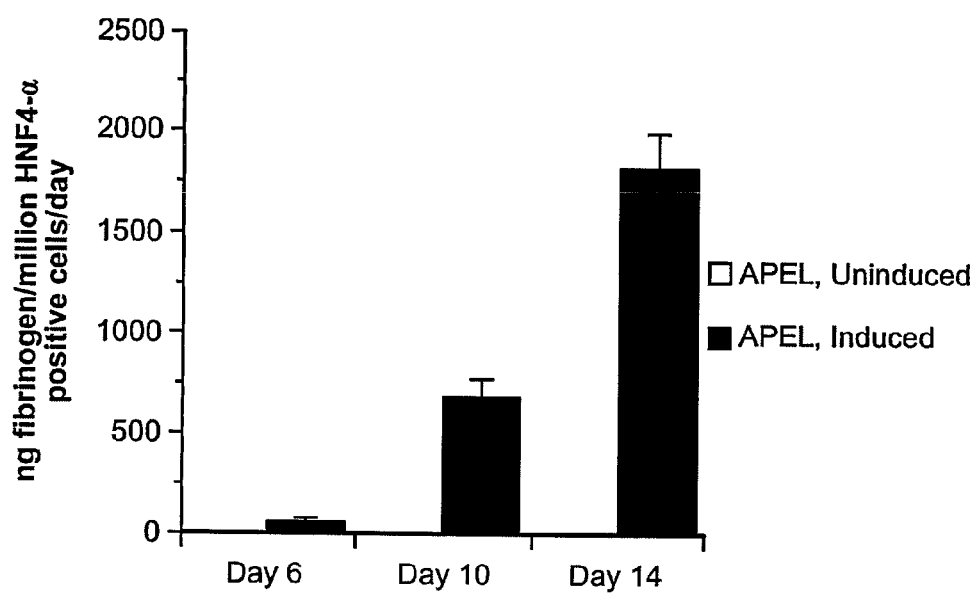
Figure 17A:
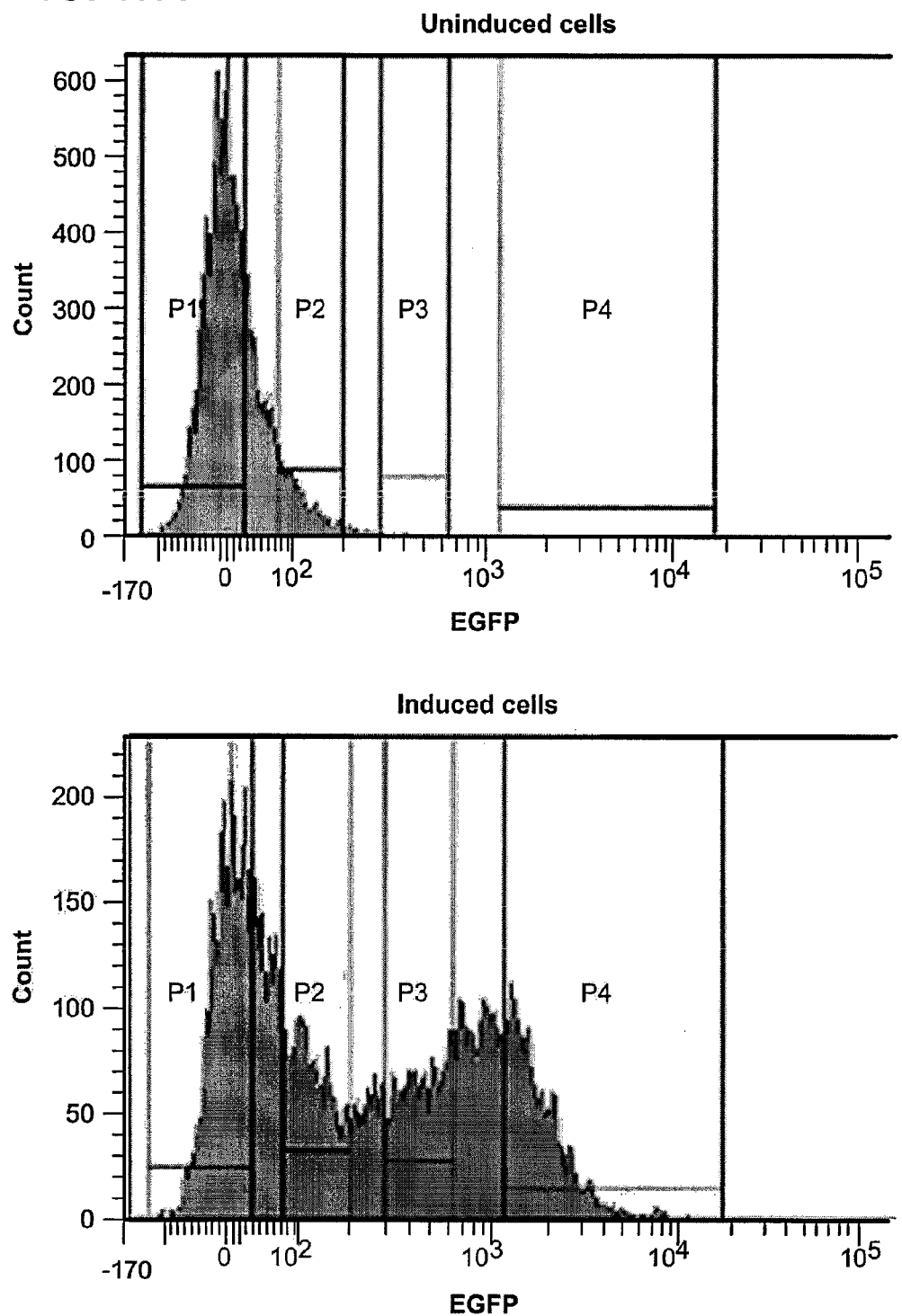
FIGS. 17A-17B show differentiation of cells expressing Gata6-EGFP sorted based on EGFP expression.
Figure 17B:
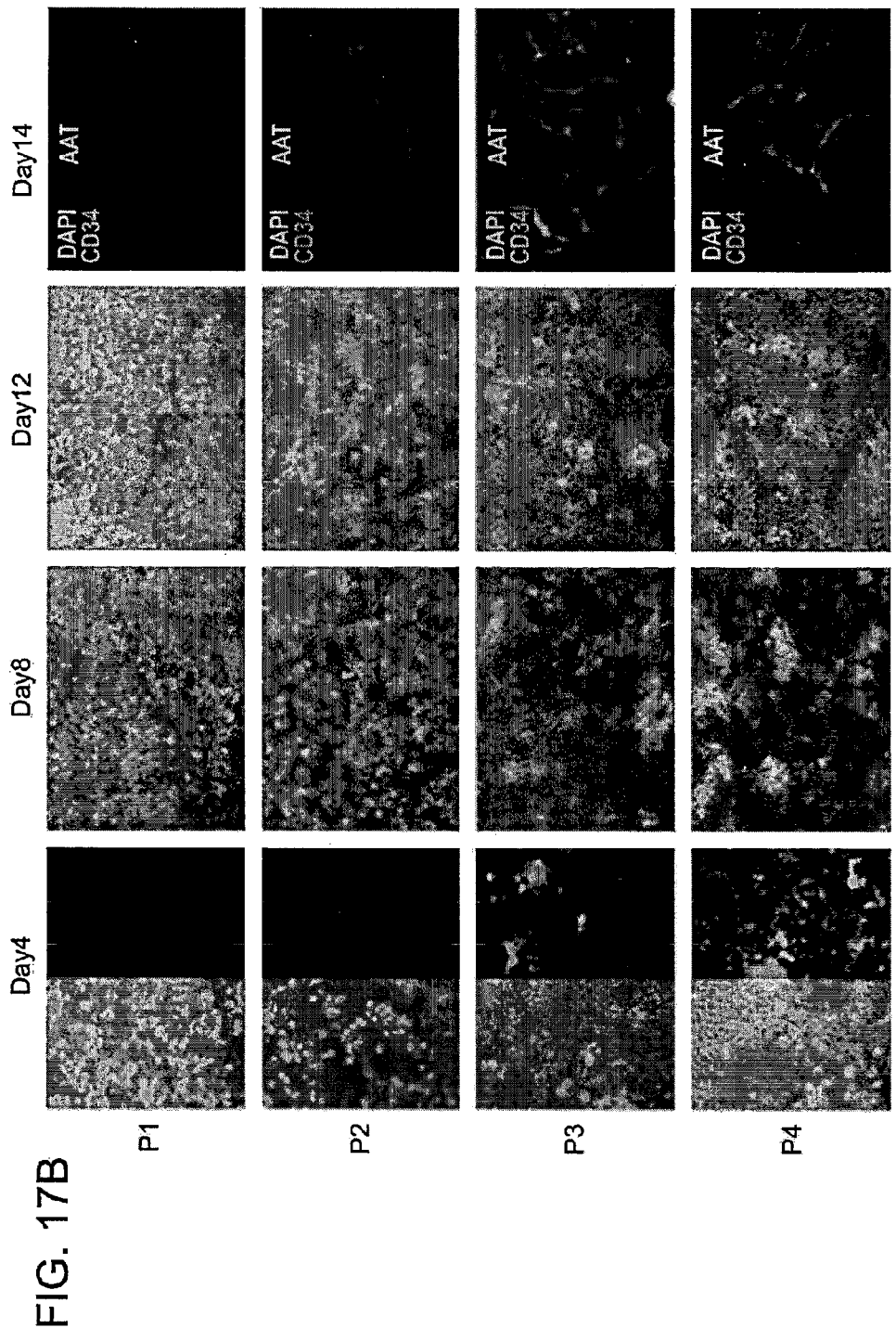

The surface biomarker CD34 was expressed early (day 4) in the endoderm layer as well later in endothelial-like tubes that emerged on day 6-7 (CD34$^+$/CD146$^+$/TAL1$^+$/FLK1$^+$/CEBPA$^-$/HNF4A$^-$) (FIGS. 3A-3B, FIGS. 8A-8B). Cells expressing Nestin (NES) and PDGFRA, biomarkers of mesenchymal precursors and associated with enhanced liver maturation as well as expansion of hematopoietic progenitors[22,23], developed within endodermal layer (FIG. 3A). The hepatic endoderm matured further as intracellular CEBPA, secreted Alpha-1 Antitrypsin (AAT) and Fibrinogen (Fib), three important biomarkers of HpLC function, strongly increase their expression between day 8 and 10 as measured in the supernatant by means of ELISA (AAT, FIB)) and with immunostaining (CEBPA, AAT) (FIG. 3B). CD34$^+$ cells with an endodermal morphology were CD34$^+$/CD146$^-$/CEBPA$^+$/HNF4A$^+$/AAT$^+$ and therefore belong to the hepatic lineage. CD34$^+$/CD146$^+$ cells additionally acquired CD31 in between days 7 and 10 and become endothelial-like cells (EnLCs), while the CD34$^+$/CD146$^-$/CEBPA$^+$/HNF4A$^+$/Ck19$^+$/AAT$^+$ cells developed a typical hepatoblast morphology (FIG. 4A). Most HpLCs expressed the markers Ck19, EpCAM, DLK1, CEBPA, LGR5, CK19, HNF4A, AAT and were CD34$^-$/CD 146$^-$ on day 14, while a sub-population was additionally CD34$^+$ (FIG. 3B, FIG. 4A, FIG. 8F)[24]. Treatment starting at day 5 with Axitinib, a small molecule tyrosine kinase inhibitor targeting VEGFR-1/-2/-3, PDGFRA and c-Kit, inhibited a later emergence of CD34$^+$/CD146$^+$/CD31$^+$ EnLCs but not of CD34$^+$/CEBPA$^+$/AAT$^+$ HpLCs (FIGS. 11A-11C). Desmin (Des) positive cells with a typical stellate-like cell (StLC) morphology appeared from the NES$^+$ population around day 10 interspersed with the HpLCs (FIG. 4A, FIGS. 8A-8F). Circular ducts containing cholangiocyte-like cells (ChLCs) (Ck7$^+$ and Aqp1$^+$) also developed within the HpLC layer (FIG. 4A, FIG. 9). Albumin was detectable in the supernatant around day 12 and increased steadily afterwards, indicating further maturation of the HpLCs (FIG. 4A). Gene enrichment analysis revealed a significant overrepresentation for liver-associated pathways including the complement cascade, a set of proteins synthesized by the liver being part of the innate immune system (Table 2).

TABLE 2

| | | | | |
|---|---|---|---|---|
| ALL GENES UP 4x and more in between day 5 and day 10 | | | | |
| Collections | # Overlaps Shown | # Gene Sets in Collections | # Genes in Comparison (n) | # Genes in Universe (N) |
| CP: BIOCARTA, CP: KEGG | 10 | 403 | 616 | 45956 |
| Gene Set Name [# Genes (K)] | | Description | # Genes in Overlap (k) | p-value | FDR q-value |
| KEGG_COMPLEMENT_ AND_COAGULATION_ CASCADES [69] | | Complement and coagulation cascades | 20 | 0.00E+000 | 0.00E+000 |
| KEGG_DRUG_METABOLISM_ CYTOCHROME_P450 [72] | | Drug metabolism - cytochrome P450 | 11 | 3.31E−009 | 6.68E−007 |
| BIOCARTA_AMI_ PATHWAY [20] | | Acute Myocardial Infarction | 7 | 5.01E−009 | 6.73E−007 |

TABLE 2-continued

ALL GENES UP 4x and more in between day 5 and day 10

| Collections | # Overlaps Shown | # Gene Sets in Collections | # Genes in Comparison (n) | # Genes in Universe (N) |
|---|---|---|---|---|
| BIOCARTA_EXTRINSIC_PATHWAY [13] | Extrinsic Prothrombin Activation Pathway | 6 | 8.97E−009 | 9.04E−007 |
| BIOCARTA_FIBRINOLYSIS_PATHWAY [12] | Fibrinolysis Pathway | 5 | 3.12E−007 | 2.51E−005 |
| KEGG_METABOLISM_OF_XENOBIOTICS_BY_CYTOCHROME_P450 [70] | Metabolism of xenobiotics by cytochrome P450 | 9 | 4.14E−007 | 2.71E−005 |
| BIOCARTA_INTRINSIC_PATHWAY [23] | Intrinsic Prothrombin Activation Pathway | 6 | 4.71E−007 | 2.71E−005 |
| KEGG_STEROID_HORMONE_BIOSYNTHESIS [55] | Steroid hormone biosynthesis | 8 | 6.97E−007 | 3.51E−005 |
| KEGG_PENTOSE_AND_GLUCURONATE_INTERCONVERSIONS [28] | Pentose and glucuronate interconversions | 6 | 1.66E−006 | 7.43E−005 |
| KEGG_RETINOL_METABOLISM [64] | Retinol metabolism | 8 | 2.28E−006 | 9.18E−005 |
| CP: BIOCARTA, CP: KEGG | 7 | 403 | 309 | 45956 |

| Gene Set Name [# Genes (K)] | Description | # Genes in Overlap (k) | k/K | p-value | FDR q-value |
|---|---|---|---|---|---|
| KEGG_COMPLEMENT_AND_COAGULATION_CASCADES [69] | Complement and coagulation cascades | 8 | | 2.24E−008 | 9.01E−006 |
| KEGG_CYTOKINE_CYTOKINE_RECEPTOR_INTERACTION [267] | Cytokine-cytokine receptor interaction | 11 | | 2.32E−006 | 4.67E−004 |
| KEGG_NEUROACTIVE_LIGAND_RECEPTOR_INTERACTION [272] | Neuroactive ligand-receptor interaction | 10 | | 1.79E−005 | 2.41E−003 |
| KEGG_PPAR_SIGNALING_PATHWAY [69] | PPAR signaling pathway | 5 | | 1.05E−004 | 1.06E−002 |
| KEGG_TGF_BETA_SIGNALING_PATHWAY [86] | TGF-beta signaling pathway | 5 | | 2.97E−004 | 2.39E−002 |
| KEGG_STEROID_HORMONE_BIOSYNTHESIS [55] | Steroid hormone biosynthesis | 4 | | 5.22E−004 | 3.51E−002 |
| KEGG_PURINE_METABOLISM [159] | Purine metabolism | 6 | | 7.60E−004 | 4.37E−002 |

Presence of hematopoietic processes was investigated in the heterogeneous tissue, as tissue with similar characteristics is an important source of hematopoietic progenitor cells[12]. Microarray data for day 5 cells showed growth factors and transcription factors upregulated in hemangioblast induction such as VEGF-A (CXCR4+ cells, FIG. 2D), CSF2/GM-CSF, TEK, GATA1 and TGFβ1 (Total cells, FIG. 3B). CD34+ cells at day 10 were enriched for genes critical for endothelial tube and hematopoietic development (FIG. 3B). Between day 10 and 14, CD34+ endothelial tubes constricted and budded off small spherical cells expressing CD45 or hemoglobin. Hemoglobin gamma was most prominently upregulated around day 15 (FIG. 4B), indicating definitive fetal erythropoiesis. Primary DLK1+ hepatoblasts isolated from mice fetal liver secrete cytokines promoting hematopoiesis/erythropoiesis[25], and CD34+ cells from midgestation human fetal liver can efficiently reconstitute human hematopoietic cells as well as hepatoblast-like cells[26]. The complex, heterogeneous tissue environment induced and supported definitive fetal hematopoiesis/erythropoiesis and maturation of HmLCs, for example, as the fetal liver bud does, and might provide a source of therapeutically valuable cells[27].

Figure 10B:
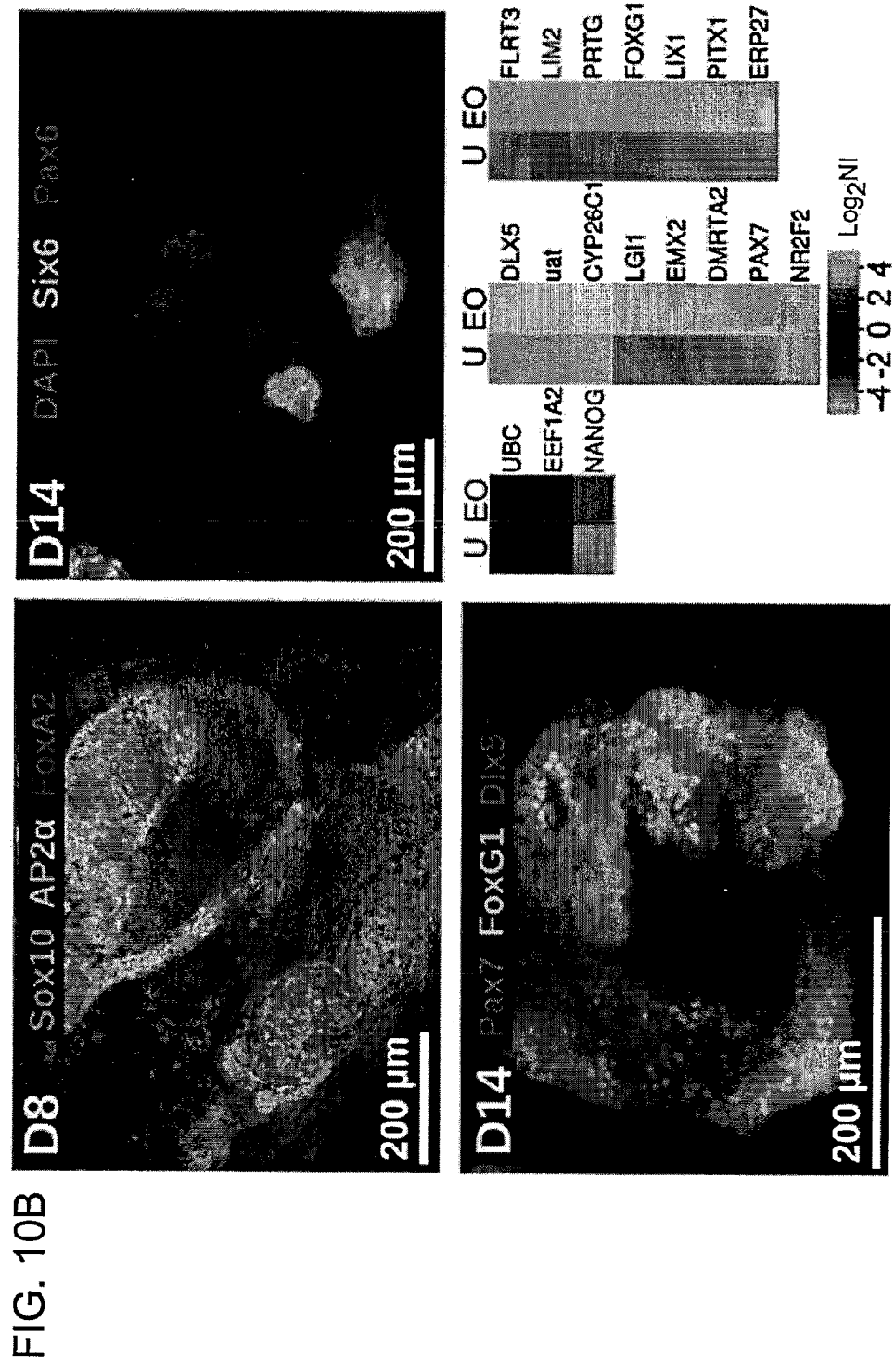

Clusters of cells with GATA6 expression too low for mesendoderm differentiation maintained high NANOG expression during the first few days (FIGS. 1A-1B). In these cells, the pluripotency and ectoderm marker OCT4 increased over the first five days (FIGS. 10A-10B), and they acquired ectodermal markers in between days 5 and 7 (AP2+/Sox10+, FIG. 3c), finally exhibiting prominent fold-like outgrowths of cells expressing markers such as AP2+, SOX9+, FOXG1+, SIX6+, PAX7+ cells, indicating differentiation to a neural lineage. Microarray analysis performed on day 15 post-induction on these outgrowths indicated an anterior/rostral fate containing markers for neural crest and anterior neural folds (FIGS. 8A-8F). Most prominently expressed is Cyp26C1, a retinoic acid-catabolizing enzyme expressed first in the anterior-most part of the embryo and later in the rostral hindbrain next to the developing forebrain[28]. Immunostaining revealed PAX6 and SIX6 expression at the top of these outgrowths in cup-like structures similar to optic cups (FIGS. 10A-10B)[29].

Methods provided herein therefore generated organized tissues comprising cells from all three developing germ layers. Notably, cytokines or growth factors, beyond factors required for maintaining hiPS cell pluripotency, were not added to the cell culture medium; however, hybrid liver-like and early neuronal tissues were induced after a short induction phase in pure IMDM medium without serum or other additives (FIG. 9). Methods of the present disclosure were verified in the following four hiPS cell lines: PGP-1, PGP-5, PGP-9 and C1 (FIGS. 11A-11C). HpLCs, ChLCs, EnLCs, HmLCs, and StLCs that co-develop in a tissue-like environment were generated and spatially separated within the same cell culture well. Maturation of the ectodermal fraction to NpLCs was also observed.

The methods provided herein open up exciting prospects for developing tissue models (e.g., drug screening) as well as for therapeutic applications (e.g., regenerative medicine) or as a model to study development. The Examples provided herein show the advantages of co-differentiating complex populations of progenitors, recapitulating the intricate processes of embryogenesis, and setting into motion processes that lead to emergence of tissues and organ(oids).

Example 2

Figure 18:
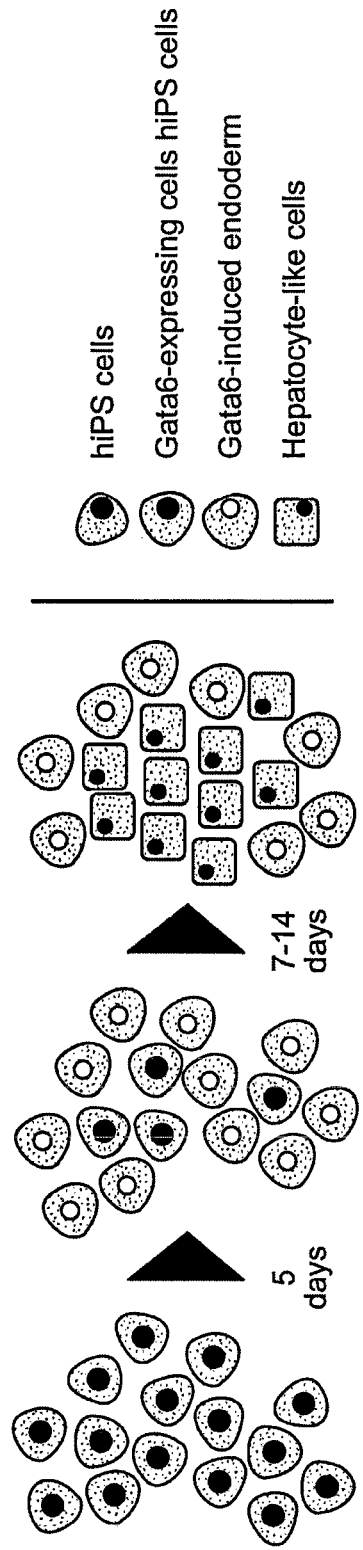
FIG. 18 shows a schematic of modified GATA6+ hiPS cells differentiating to primitive-like endoderm.

Provided herein is a method for generating hepatocytes from hiPS cells by emulating early embryonic development. Gata transcription factors were ectopically expressed in hiPS cells, inducing them to differentiate to primitive-like endoderm (FIG. 18). At the same time, these cells were co-cultivated with wild-type hiPS cells (not expressing Gata factors). This generated, after about two weeks, cells having a transcriptional profile and morphology very close to mature hepatocytes. Without being bound by theory, the interaction of primitive endoderm and pluripotent hiPS cells may induce definitive endoderm and subsequently hepatic lineages. Hepatocytes generated using this method expressed many important markers for mature hepatocytes at high levels and appeared to be stable in cell culture. Thus, provided herein are methods for re-creating conditions close to gastrulation/early embryogenesis in vitro using engineered (e.g., modified), complex populations of cells for generating mature, specialized cell types and self-assembling complex tissues (e.g., heterogeneous tissues).

Existing protocols to differentiate human induced pluripotent stem (hiPS) cells to hepatocyte-like cells use either complex cocktails of cytokines/growth factors or transcription factors specific for the hepatic lineage. These induced hepatocyte-like cells (iHeps) have significant deficiencies in critical markers (e.g. reduced Albumin production) in comparison to primary hepatocytes and have therefore a limited usefulness. Primary hepatocytes in turn are difficult to acquire in large numbers or for rare patient genotypes and down-regulate important markers in in-vitro cell culture conditions. Methods provided herein, in some embodiments, do not rely on expensive cytokines or complex media formulation and involve very little manual work to generate hepatocytes (and other cell types) from hiPS cells.

Figure 19A:
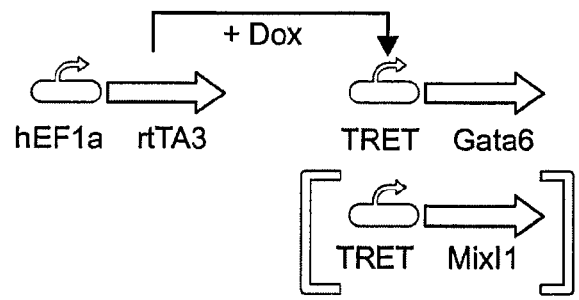
Figure 19B:
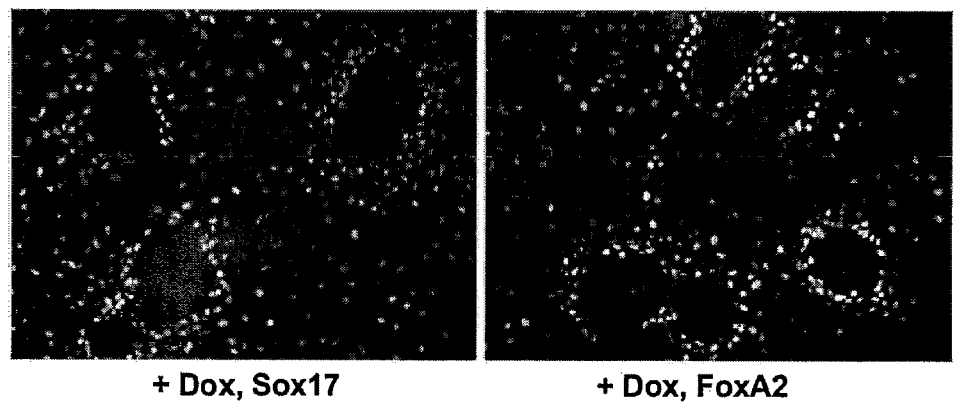
Figure 20A:
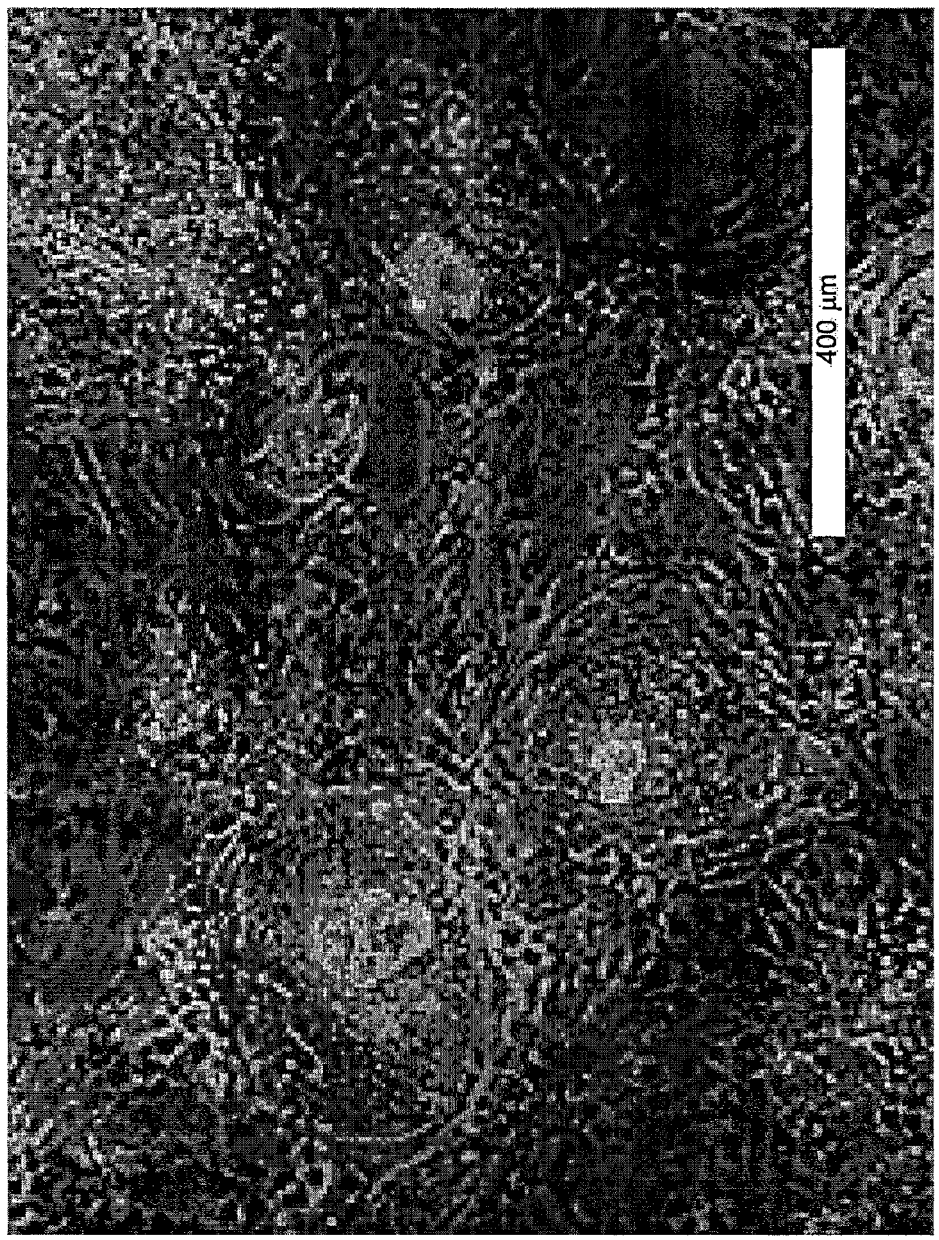
FIGS. 20A-20C show microscopy images at later stages (days 8, 13 and 35).
Figure 20B:
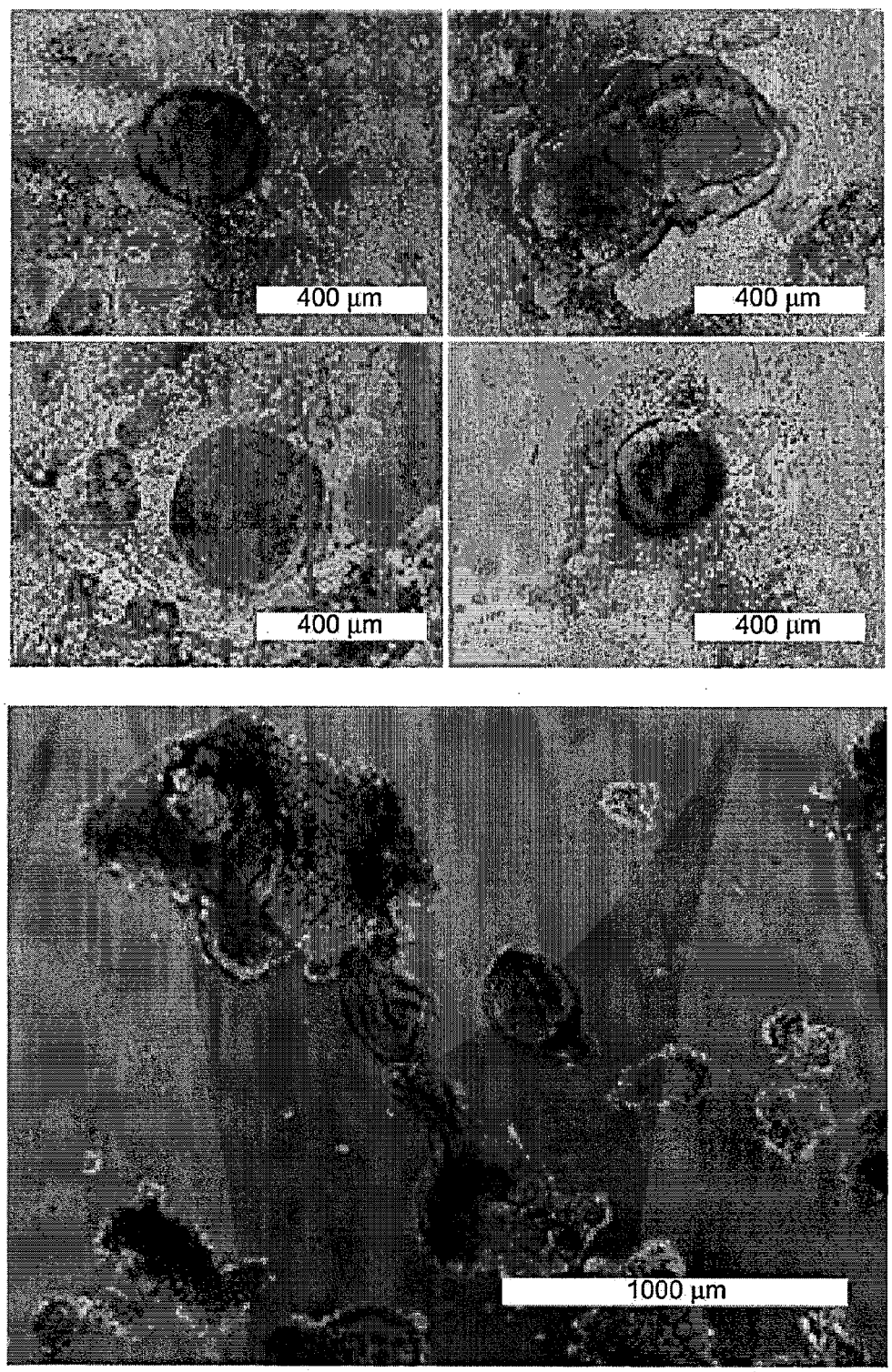
Figure 20C:
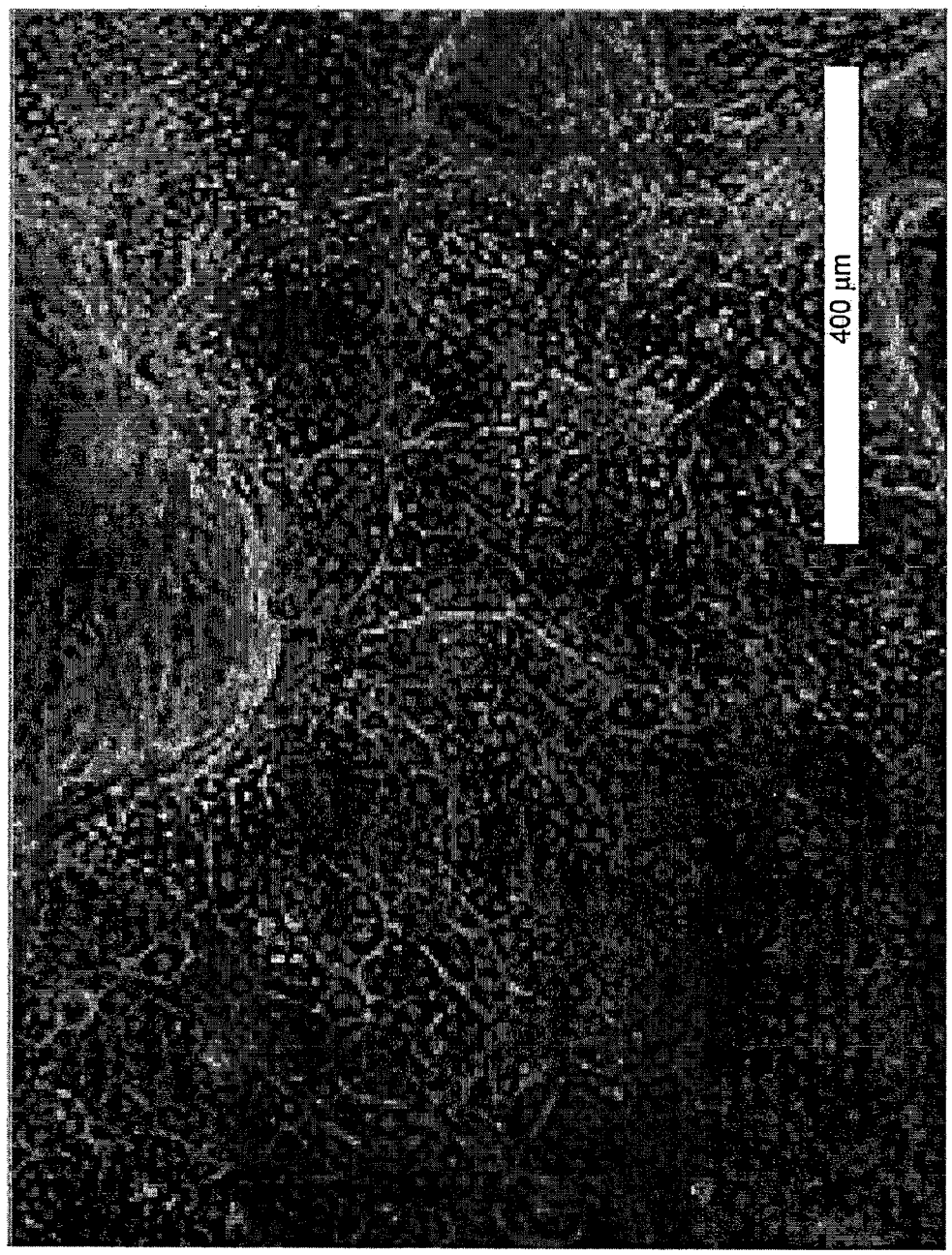

HiPS cells were transduced with a lentivirus constitutively expressing a doxycycline-activatable transactivator (hEF1a_rtTA3, FIG. 19A) and a lentivirus encoding a minimal promoter with binding sites for rtTA3 followed by a Kozak sequence and murine Gata6 (TRET_mGata6) and optionally human Mixl-1 (TRET_hMixl1). Upon addition of doxycycline mGata6 and hMixl-1 expression was induced in the cells. While being kept in a medium promoting pluripotency (e.g. mTeSR-1) for the first five days, a population of hiPS differentiated to an endoderm-like stage (FOXA2+, SOX17+, CXCR4+, HNF4A+) and loss pluripotency markers (OCT4, TRA-1-81), as assessed on day 5 (FIGS. 19B and 19B). A subpopulation of hiPS not transduced with the virus or having silenced the transgenes stayed pluripotent (OCT4+, TRA-1-81+) during this time as islands. On day 5, the medium was switch to a medium not supporting pluripotency (F-12, DMEM) and the cells were kept in culture for 1-2 weeks more (FIGS. 20A-20C). Total RNA was extracted on day 0, 5 and 13 and subsequently analyzed on Agilent microarrays (SurePrint G3 Human Gene Expression 8×60K).

Removing pluripotent cells on day 5 using a tissue-specific promoter and antibiotic selection or using only wild-type hiPS cells (no inducible Gata factors) did not yield hepatocyte-like cells. Without being bound by theory, this suggest that the interaction between the primitive-like endoderm cells and the pluripotent hiPS might be important and required to generate hepatocytes.

While the transgenes were delivered using lentiviruses, other delivery methods include, without limitation, transfecting mRNA or RNA viruses encoding the necessary factors, thereby circumventing potential problems that may be associated with genomic integrations and risk of mutagenesis.

DNA Constructs

The UBC promoter was amplified from pFUW (Lois C, Hong E J, Pease S, Brown E J, Baltimore D; Germline transmission and tissue-specific expression of transgenes delivered by lentiviral vectors, Science 2002) using oligos oPG106 and oPG107 and TOPO cloned into pENTR_L4R1 (Life Technologies), resulting in pENTR_L4_UBC_R1. pENTR_L4_TRET_R1, pENTR_L1_EGFP_L2, pENTR_L4_hEF1a_R1 and pENTR_L4_MCS_R1 are described elsewhere (Rapid, modular, and reliable construction of complex mammalian gene circuits; Guye, Li, Wroblewska, Duportet and Weiss; Nucleic Acid Research 2013). For constructing pENTR_L1_rtTA3-2A-Hygro_L2, rtTA3 was amplified using oPG106/107 and digested with BamHI/EcoRI. This fragment was ligated with a MfeI/NotI-cut PCR product encoding a 2A-Hygromycin (amplified in two steps using oPG316a/oPG317 then oPG316b/oPG317) into a previously BamHI/NotI-cut pENTR_L1L2 (Life Technologies). pENTR_L1_hGata6_L2 was constructed by PCR-amplifying all six genomic exons in the human Gata6 gene from genomic DNA using the oligos pPG6371-6381 and assembling the parts in a single pot reaction into pENTR_L1L2 by means of the Golden Gate Reaction (A One Pot, One Step, Precision Cloning Method with High Throughput Capability; Engler, Kandzia, Marillonnet; PLOS One 2008). pENTR_L1_hGata6-HA_L2 was constructed by PCR-amplifying human Gata6 from pENTR_L1_hGata6_L2 using oligos oPG_hG6_RegStartF and oPG6_RegTermR and recombining the resulting PCR product into pDONR221P1P2 using the BP reaction (Life Technologies). pENTR_L1_mGata6_L2 was constructed by amplifying Gata6 from mouse Gata6 cDNA (kind gift of I. Lemischka) using oPG630/621 and recombining the resulting PCR product into pDONR221P1P2 using the BP reaction. pENTR_L1_hGata6-2A-Puro_L2 was constructed by PCR-amplifying Gata6 from pENTR_L1_hGata6_L2 using oPG6382/6383, 2A-Puromycin from AAVS1-SA-2A-puro-pA (Addgene Plasmid 22075) using oPG6385/6386 and cloning the products by means of a Golden Gate Reaction into pENTR_L1L2. pENTR_L1_hGata6-2A-EGFP_L2 was constructed by PCR-amplifying Gata6 from pENTR_L1_hGata6_L2 using oPG_hGX-2A-EGFP_G6-fwd/oPG_GX-2A-EGFP_G6-rev and EGFP from pFUW using oPG_hGX-2A-EGFP_EGFP-fwd/oPG_hGX-2A-EGFP_EGFP-rev and cloning the parts into pENTR_L1L2 using a Golden Gate Reaction. pENTR_L1_mKate2_L2 was constructed by means of gene synthesis on the template of mKate2 (Evrogen, Russia). pENTR_L4_hA1b_R1 was constructed by PCR-amplifying a promoter fragment spanning base pairs-1966 to +35 relative to the transcriptional initiation of the human Albumin gene from genomic DNA using oPG5141/oPG5151, digesting the resulting fragment with XhoI/EcoRI and restriction enzyme cloning it into XhoI/EcoRI-cut pENTR_L4_MCS_R1. peNTR_L1_EBFP2_L2 was constructed by PCR-amplifying EBFP2 from pLV-EBFP2-nuc (Addgene Plasmid 36085) using oPG1162/oPG1163 and recombining the resulting PCR product into pDONR221P1P2 by means of the BP reaction (Life Technologies). pLV_Dest-R4R2 was constructed by PCR-amplifying the backbone of pFUW-OSKM (Addgene Plasmid 20328) with oPG240/oPG241, digesting the product with PacI and EcoRI and ligating it with a PacI/MfeI-cut PCR product amplified with oPG242/oPG243 from pLenti6/R4R2/V5-DEST (Life Technologies). pLV_UBC_rtTA3-2A-Hygro was constructed by recombining pENTR_L4_UBC_R1 with pENTR_L1_rtTA3-2A-Hygro_L2 into pLV_Dest-R4R2 using the LR Recombinase (Life Technologies). pLV_TRET_mGata6 was constructed by recombining pENTR_L4_TRET_R1 with pENTR_L1_mGata6_L2 into pLV_Dest-R4R2 using the LR Recombinase. pLV_TRET_hGata6-HA was constructed by recombining pENTR_L4_TRET_R1 with pENTR_L1_hGata6-HA_L2 into pLV_Dest-R4R2 using the LR Recombinase. pLV_TRET_hGata6-2A-EGFP was constructed by recombining pENTR_L4_TRET_R1 with pENTR_L1_hGata6-2A-EGFP_L2 into pLV_Dest-R4R2 using the LR Recombinase. pLV_TRET_hGata6-2A-Puro was constructed by recombining pENTR_L4_TRET_R1 with pENTR_L1_hGata6-2A-Puro_L2 into pLV_Dest-R4R2 using the LR Recombinase. pLV_hA1b_mKate2 was constructed by recombining pENTR_L4_hA1b_R1 with pENTR_L1_mKate2_L2 into pLV_Dest-R4R2 using the LR Recombinase. pLV_hEF1a_mKate2 was constructed by recombining pENTR_L4_hEF1a_R1 with pENTR_L1_mKate2_L2 into pLV_Dest-R4R2 using the LR Recombinase. pLV_hEF1a_EBFP2 was constructed by recombining pENTR_L4_hEF1a_R1 with pENTR_L1_EBFP2_L2 into pLV_Dest-R4R2 using the LR Recombinase.

TABLE 3

| Name | Oligo Sequence (5'-3') |
| --- | --- |
| oPG106 | GAGAACAGGTCGGATCTGTACCACCGCTGGCCATGG GCCCCTAGGGCGAG (SEQ ID NO: 7) |
| oPG107 | GCTAAAACTGGAACTGTACGAGGGGCCCCTTAAGCC TGAG (SEQ ID NO: 8) |
| oPG316a | CAAAAGGAGGTGCAGCGGCGTCCAGTCGTCCGACGG CGCCGGGAGGTTAACGAAC (SEQ ID NO: 9) |
| oPG316b | AGCGCCACTCAAGTCCGAAAAAGTACCCCGGCCCCA AAAGGAGGTGCAGCGGCGTCCAG (SEQ ID NO: 10) |
| oPG317 | CTAGCCCTCTACCCCCTCCGATTGACTCGCCGGCGC TTAAGATG (SEQ ID NO: 11) |
| oPG6370 | CGGCGGCAGTCAGTTCCGGTACCACCGCTTGGAACT CTGGTTT (SEQ ID NO: 12) |
| oPG6371 | ACGGGGCCCCAGGGTCACGTCACTCTGGAAA (SEQ ID NO: 13) |
| oPG6372 | GAGCCTGTCCAGGAGGTCGTCCAGACGACTCTGGTT T (SEQ ID NO: 14) |
| oPG6373 | GTTCGGCGTCTTCGCGCACACTCTGGAAA (SEQ ID NO: 15) |

TABLE 3-continued

| Name | Oligo Sequence (5'-3') |
| --- | --- |
| oPG6374 | GTTAGGTTCGGCGGCACTACTTCCGTGCACTCTGGT TT (SEQ ID NO: 16) |
| oPG6375 | GAACACCTGAGATGTACTTTGAGGTACCCACTCTGG AAA (SEQ ID NO: 17) |
| oPG6376 | GAGAAAAAAGTATCGTTCACCAGACCCGTGGGGTAC TCTGGTTT (SEQ ID NO: 18) |
| oPG6377 | GGATTCTTGTATTTATTTAGTTTCTGAACGAGACAC TCTGGAAA (SEQ ID NO: 19) |
| oPG6378 | CAACCTCAGTACCCTTACCTTAATAACGATAATGGT CTACTCTGGTTT (SEQ ID NO: 20) |
| oPG6379 | GGGGTGTTGTGTTGGATGTCGGAGTCCACTCTGGAA A (SEQ ID NO: 21) |
| oPG6380 | GTCAGTAGTGGCCCCGTGGGCGGGGACACTCTGGTT T (SEQ ID NO: 22) |
| oPG6381 | CGCGGGACCGGGACCGGACTCGAAACTCTGGAAA (SEQ ID NO: 23) |
| oPG630 | CGGCGGCAGTCAGTTCCGGTACCACCGCTCGGACGA AAAAACATGTTTGAACAGGGG (SEQ ID NO: 24) |
| oPG631 | CACGAGACCGGGACCGGACTATGGTGGGTCGAAAGA ACATGTTTCACCAGGGG (SEQ ID NO: 25) |
| oPG6382 | GTCAGTTCCGGTACCACCGCTTGGAACTCTGGTTT (SEQ ID NO: 26) |
| oPG6383 | CACGCGGGACCGGGACCGGCTCCACTCTGGAAA (SEQ ID NO: 27) |
| oPG6386 | CTCCAACGCCCCGCGCCTCCACTCTGGTTT (SEQ ID NO: 28) |
| oPG6385 | CCCCACGGGCGGAAGGACCTCGGAGACTCTGGAAA (SEQ ID NO: 29) |
| oPG_hG6_RegStartF | CGGCAGTCAGTTCCGGTACCACCATTCGGACGAAAA AACATGTTTGAACAGGGG (SEQ ID NO: 30) |
| oPG6_RegTermR | CACGCGGGACCGGGACCGGCCGATAGGAATGCTGCA CGGACTGATGCGGACTATGGGTCGAAAGAACATGTT TCACCAGGGG (SEQ ID NO: 31) |
| oPG_hGX-2A-EGFP_EGFP-fwd | GAGGAGCGGGAACGAGTGGTACCCCGGCCCCAAAAG GAGGTGCAGCGGCGACTCTGGTTT (SEQ ID NO: 32) |
| oPG_hGX-2A-EGFP_EGFP-rev | CCGTACCTGCTCGACATGTTCATTCGAAACTCTGGA AA (SEQ ID NO: 33) |
| oPG_hGX-2A-EGFP_G6-fwd | CAGTTCCGGTACCACCGCTTGGATGGAACTCTGGTT T (SEQ ID NO: 34) |
| oPG_GX-2A-EGFP_G6-rev | CGTCGGACGACTGGACGCCACTCTGGAAA (SEQ ID NO: 35) |
| oPG5141 | GATTACTTCTCGGGATCGAAAGAGCTCCTTAACGG (SEQ ID NO: 36) |
| oPG5151 | GATTAAAGGGAGGCAAACAGGATCTTAAGAAGACGT C (SEQ ID NO: 37) |
| oPG1162 | GTCGAGGAGCGGGAACGAGTGGTACCACCGCTCGGA CGAAAAAACATGTTTGAACAGGGG (SEQ ID NO: 38) |

TABLE 3-continued

| Name | Oligo Sequence (5'-3') |
|---|---|
| oPG1163 | ACCTGCTCGACATGTTCATTATGGTGGGTCGAAAGA ACATGTTTCACCAGGGG (SEQ ID NO: 39) |
| oPG240 | CCCTGTCGTCTCTAGGTCAAACCAATTAATTCCTAG G (SEQ ID NO: 40) |
| oPG241 | CCAACTAATAGCTATTCGAACTATAGCTTAACGGCC TTAAGTGGTG (SEQ ID NO: 41) |
| oPG242 | GCAAAGAGCAAGTTGAAAAGATATGTTTCAACTAAT TAATTCTTAAG (SEQ ID NO: 42) |
| oPG242 | GAGCAAGTCGAAAGAACATGTTTCACCACTTAAGGC CGTTAACCCTAAG (SEQ ID NO: 43) |

Lentiviral Particles Production

HEK293FT cells (Life Technologies) were grown according to the manufacturer's indication in a humidified incubator at 37° C. with 5% $CO_2$. The day prior to transfection, eight million HEK293FT cells were seeded on a Gelatine-coated 150 $cm^2$ cell culture dish. On the day of transfection, the cell culture medium was replaced and the cells were transfected with 15 μg pCMV-dR8.2 dvpr (Addgene Plasmid 8455), 3.75 μg pCMV-VSV-G (Addgene Plasmid 8454) and 11.25 μg of the plasmid to be packaged (pLV) using Metafectene Pro (Biontex, Germany). Six hours post transfection the medium was changed and 20 ml of fresh cell culture medium added to the cells. Two days later, we harvested the supernatant and stored it at 4 C. 20 ml of fresh cell culture medium was added to the cells. The next day, supernatant and the previous day's stored supernatant were pooled, filtered through a 0.45 μm low protein binding filter (Corning) and then further concentrated in an Amicon Ultra 15 filter columns (100 kDa cutoff, Millipore) at 4000×g to a final volume of 400 μl. The concentrated virus was then aliquoted and stored at −80° C.

Cell Culture

The PGP1, PGP5 and PGP9 hiPSCs were a kind gift from George Church (Harvard, USA) and can be obtained from Coriell (NJ, USA). The C1 hiPSC was a kind gift from Rudolf Jaenisch (MIT/Whitehead, USA). Cells were cultivated under sterile conditions in mTeSR-1 (Stem Cell Technologies, Vancouver) in a humidified incubator at 37° C. and 5% $CO_2$. Tissue culture plates were coated for one hour at room temperature with BD ES-qualified Matrigel (BD Biosciences) diluted 1:75 v/v in ice cold DMEM/F-12 with 15 mM HEPES medium (Stem Cell Technologies, Vancouver).

Routine passaging was performed by incubating hiPSC's for seven minutes in Accutase (1 ml per 10 $cm^2$, Stem Cell Technologies, Vancouver) at 37° C. followed by three 2 ml washes in DMEM/F-12 medium and mechanical dissociation (#3010 cell scraper, Corning). Subsequently the cells were taken up in 5 ml of DMEM/F-12, centrifuged at 500 rpm for 3 min and resuspended in mTeSR-1. Clump size was assessed by eye and if necessary a further reduction in size was performed by gently pipetting the suspension.

Single cell suspensions were generated by incubating hiPSC colonies for five minutes in Accutase (Stem Cell Technologies, Vancouver) at 37° C., subsequently resuspending this single cell solution in 5 ml of DMEM/F-12 medium containing 10 μM Y-27632 dihydrochloride (Tocris Biosciences, UK) solubilized in cell culture grade DMSO (Sigma-Aldrich), centrifuging it at 500 rpm for 3 min and resuspending the pellet in mTeSR-1 or DMEM/F-12 supplemented with Y-27632 at a final concentration of 10 μM for counting.

Magnetic Isolation of Cells

CXCR4 and CD34 isolations were performed at day 5 and 10 respectively using mouse anti-CXCR4 and mouse anti-CD34 antibodies conjugated to magnetic beads (Miltenyi). The suspensions were then flowed through Miltenyi magnetic bead LS separation columns alongside a magnet to trap the positive cell population. The columns were then removed from the magnets and flushed out with MACS magnetic bead isolation buffer, tagged with fluorophore conjugated antibodies, fixed in 2% PFA, and analyzed using a BD Accuri C6 flow cytometer. Fluorophore conjugated CXCR4 and CD34 antibodies targeting different epitopes than the bead conjugated antibodies were used for FACS analysis.

Time Lapse Imaging

Gata6 engineered iPS cells were seeded at 26 k cells/cm2 in a BD 6-well tissue culture treated plate coated with BD Matrigel, then induced with doxycycline. After induction, the cells were viewed under a Leica DMI6000 Confocal Laser Scanning Microscope, in an incubation chamber. Images were taken every 30 minutes for four days.

Flow Cytometric Sorting of Cells

Gata6-EGFP engineered iPS cells were induced for 2 days, removed from their plates with Accutase (Stemcell Technologies), and suspended at 2 million cells/mL in mTeSR-1 supplemented with 10 μM of Y-27632 and 0.6 uM Thiazovivin (Tocris Biosciences). The cells were separated by EGFP fluorescence signal into four populations using a BD Aria III cell sorter. The separated populations were reseeded into BD 24-well plates on matrigel coated glass coverslips on mTeSR and switched to APEL at day 5. The cultures were monitored for 9 days on APEL media.

Ectodermal Outgrowth Isolation

Ectodermal outgrowths were identified visually and picked using a mouth-operated vacuum pipette. Three times 35 outgrowths were picked (N=3) and immediately subjected to RNA extraction.

RNA Extraction, Gene Arrays.

Total RNA was extracted from cell pellets using the Arcturus Picopure Kit (Ambion/Life Technologies) and stored at −80° C. and submitted to the MIT Biomicro Center (Cambridge, Mass.) where quality control, processing and data acquisition for the microarray (SurePrint G3 Human Gene Expression 8×60K v2 Microarray Kit, Agilent) was performed according to their manual. Gene Array data was analyzed using Genespring GX 12 (Agilent). Heatmaps were generated using R and the heatmap.2 package (website: r-project.org/).

Immunofluorescence

Cells were grown on Matrigel-coated glass coverslips and fixed for 20 min in 4% Fixation Buffer (BioLegend, USA) at room temperature. The coverslips were washed in 3 times in 250 μl Phosphate Buffered Saline (PBS) spotted on Parafilm M (Pechiney Plastic Packaging Company, Chicago) followed by 15 min permeabilization in 100 μl of 0.2% Triton X-100 in PBS. Subsequently the coverslips were washed 3 times in 250 μl in PBS for 5 min and blocked for 20 min in 250 μl 4% normal donkey serum (Abcam, USA) in PBS. The incubation with the primary antibodies was performed for one hour at room temperature in 25 μl of 4% normal donkey serum in PBS followed by three washes in 250 μl in PBS for 5 min. The incubation with the secondary antibodies was performed for one hour at room temperature in 25 μl of 4% normal donkey serum in PBS followed by three washes in 250 μl in PBS for 5 min. Finally, the coverslips were mounted on microscopy glass slides using ProLong Gold antifade (Life Technologies, USA), left to cure overnight at room temperature and then sealed with nail polish. Primary antibodies: PAX7 (R&D MAB 1675, 1:500), PROX1 (Abcam ab37128), SOX17 (R&D AF1924, 1:200), NANOG (Abcam ab80892, 1:200), CEBPA (R&D AF7094, 1:200), DES (Santa Cruz sc-7559, 1:200), DES (Santa Cruz sc14026, 1:200), AAT (R&D AF1268, 1:200), FOXG1 (Abcam ab18259, 1:500), SOX10 (Abcam ab155279, 1:200), DLK1 (Abcam ab89908, 1:200), TFAP2A (Abcam ab11828, 1:500), TFAP2A (Santa Cruz sc12726, 1:200), CD45 (Abcam ab33522, 1:200), NES (Santa Cruz sc21247, 1:200), KRT19/Ck19 (Abcam ab52625, 1:200), EPCAM/CD133 (Abcam ab71916), CD34 (Abcam ab81289, 1:200), KDR/Flkl (Santa Cruz sc-6251, 1:200), HA (Millipore 05-904, 1:400), DLX5 (Santa Cruz sc18151, 1:200), LGR5 (Santa Cruz sc-68580, 1:200), CD184/CXCR4 (conjugate to PE, BD Pharmingen 561734, 1:200), TRA-1-80 (conjugated to Alexa 488, Stemgent 09-0069, 1:200), FOXA2 (Santa Cruz sc-271104, 1:200), CD31 (Cell Signaling #3528S, 1:200), pan-Hemoglobin (Santa Cruz sc-22718, 1:200), SIX6 (Santa Cruz sc-25070, 1:200), OCT4/POU5F1 (R&D MAB 1759, 1:200), CK7 (Santa Cruz sc-53263, 1:200), AQP1 (Santa Cruz sc-32737, 1:200), HNF4A (Cell Signaling Technology 3113S, 1:200), PDGFA (Cell Signaling Technology 5241P, 1:200), AFP (Santa Cruz sc-8399, 1:200), CD146 (Santa Cruz sc-18837, 1:200). Secondary antibodies used were donkey Alexa Fluor 488 and 597 or 488, 546 and 633 conjugates respectively (Invitrogen, 1:500). Epifluorescence images were acquired using a Zeiss Axiovert 200M microscope equipped with a 1344×1024 pixel cooled ORCA-ER CCD camera (Hamamatsu Corporation) and a 10× objective. Fluorecence images were analyzed with the Axiovision digital image processing package (Zeiss). Confocal images were taken using a Leica TCS SP5 II 405UV confocal microscope (Leica Microsystems, Bannockburn, Ill.). Images were acquired using a sequential scan for the respective fluorophores.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

References (Each reference below is incorporated by reference herein.)

1. Robinton D A, Daley G Q. Nature. 2012 Jan. 18; 481(7381):295-305. doi: 10.1038/nature10761. The promise of induced pluripotent stem cells in research and therapy.
2. Stem cells assessed. Blanpain C, Daley G Q, Hochedlinger K, Passegue E, Rossant J, Yamanaka S, Nat Rev Mol Cell Biol. 2012 Jun. 8; 13(7):471-6. doi: 10.1038/nrm3371.
3. Pluripotent stem cells in regenerative medicine: challenges and recent progress. Nat Rev Genet. 2014 Jan. 17; 15(2):82-92. doi: 10.1038/nrg3563. Tabar V, Studer L.
4. Nat Rev Mol Cell Biol. 2009 February; 10(2):91-103. doi: 10.1038/nrm2618. Epub 2009 Jan. 8. Making a commitment: cell lineage allocation and axis patterning in the early mouse embryo. Arnold S J, Robertson E J.
5. Self-organizing optic-cup morphogenesis in three-dimensional culture. Eiraku M, Takata N, Ishibashi H, Kawada M, Sakakura E, Okuda S, Sekiguchi K, Adachi T, Sasai Y. Nature. 2011 Apr. 7; 472(7341):51-6. doi: 10.1038/nature09941.
6. Cerebral organoids model human brain development and microcephaly. Lancaster M A, Renner M, Martin C A, Wenzel D, Bicknell L S, Hurles M E, Homfray T, Penninger J M, Jackson A P, Knoblich J A. Nature. 2013 Sep. 19; 501(7467):373-9. doi: 10.1038/nature12517. Epub 2013 Aug. 28.
7. Vascularized and functional human liver from an iPSC-derived organ bud transplant. Takebe T, Sekine K, Enomura M, Koike H, Kimura M, Ogaeri T, Zhang R R, Ueno Y, Zheng Y W, Koike N, Aoyama S, Adachi Y, Taniguchi H. Nature. 2013 Jul. 25; 499(7459):481-4. doi: 10.1038/nature12271. Epub 2013 Jul. 3.
8. The promise of induced pluripotent stem cells in research and therapy. Robinton D A, Daley G Q. Nature. 2012 Jan. 18; 481(7381):295-305. doi: 10.1038/nature10761. Review.
9. The increasing burden of mortality from viral hepatitis in the United States between 1999 and 2007. Ly K N, Xing J, Klevens R M, Jiles R B, Ward J W, Holmberg S D. Ann Intern Med. 2012 Feb. 21; 156(4):271-8.
10. Genetic therapies: Correcting genetic defects with CRISPR-Cas9. Lokody I. Nat Rev Genet. 2014 February; 15(2):63. doi: 10.1038/nrg3656. Epub 2013 Dec. 17.
11. Vertebrate endoderm development and organ formation. Zorn A M, Wells J M. Annu Rev Cell Dev Biol. 2009; 25:221-51. doi: 10.1146/annurev.cellbio.042308.113344.
12. Organogenesis and development of the liver. Si-Tayeb K, Lemaigre F P, Duncan S A. Dev Cell. 2010 Feb. 16; 18(2):175-89. doi: 10.1016/j.devcel.2010.01.011.
13. Developmental mechanisms directing early anterior forebrain specification in vertebrates. Andoniadou C L, Martinez-Barbera J P. Cell Mol Life Sci. 2013 October; 70(20):3739-52. doi: 10.1007/s00018-013-1269-5. Epub 2013 Feb. 9.
14. Gene function in mouse embryogenesis: get set for gastrulation. Tam P P, Loebel D A. Nat Rev Genet. 2007 May; 8(5):368-81. Epub 2007 Mar. 27.
15. GATA-6 maintains BMP-4 and Nkx2 expression during cardiomyocyte precursor maturation. Peterkin T, Gibson A, Patient R. EMBO J. 2003 Aug. 15; 22(16):4260-73
16. GATA6 is essential for embryonic development of the liver but dispensable for early heart formation. Zhao R, Watt A J, Li J, Luebke-Wheeler J, Morrisey E E, Duncan S A. Mol Cell Biol. 2005 April; 25(7):2622-31.
17. GATA-6 promotes cell survival by up-regulating BMP-2 expression during embryonic stem cell differentiation. Rong L, Liu J, Qi Y, Graham A M, Parmacek M S, Li S. Mol Biol Cell. 2012 September; 23(18): 3754-63. doi: 10.1091/mbc.E12-04-0313. Epub 2012 August
18. The endoderm of the mouse embryo arises by dynamic widespread intercalation of embryonic and extraembryonic lineages. Kwon G S, Viotti M, Hadjantonakis A K. Dev Cell. 2008 October; 15(4):509-20. doi: 10.1016/j.devcel.2008.07.017.
19. Nat Biotechnol. 2012 May 27; 30(6):531-42. doi: 10.1038/nbt.2239. Isolation of primitive endoderm, mesoderm, vascular endothelial and trophoblast progenitors from human pluripotent stem cells. Drukker M, Tang C, Ardehali R, Rinkevich Y, Seita J, Lee A S, Mosley A R, Weissman I L, Soen Y.
20. The expression of CXCR4/CXCL12 in first-trimester human trophoblast cells. Wu X, Li D J, Yuan M M, Zhu Y, Wang M Y. Biol Reprod. 2004 June; 70(6):1877-85. Epub 2004 Feb. 18.
21. Analysis of human embryos from zygote to blastocyst reveals distinct gene expression patterns relative to the mouse. Niakan K K, Eggan K. Dev Biol. 2013 Mar. 1; 375(1):54-64. doi: 10.1016/j.ydbio.2012.12.008. Epub 2012 Dec. 19.
22. Role and regulation of PDGFRa signaling in liver development and regeneration. Awuah P K, Nejak-Bowen K N, Monga S P. Am J. Pathol. 2013 May; 182(5):1648-58. doi: 10.1016/j.ajpath.2013.01.047. Epub 2013 Mar. 23.
23. PDGFRα and CD51 mark human nestin+ sphere-forming mesenchymal stem cells capable of hematopoietic progenitor cell expansion. Pinho S, Lacombe J, Hanoun M, Mizoguchi T, Bruns I, Kunisaki Y, Frenette P S. J Exp Med. 2013 Jul. 1; 210(7):1351-67. doi: 10.1084/jem.20122252. Epub 2013 Jun. 17.
24. Mouse hepatoblasts at distinct developmental stages are characterized by expression of EpCAM and DLK1: drastic change of EpCAM expression during liver development. Tanaka M, Okabe M, Suzuki K, Kamiya Y, Tsukahara Y, Saito S, Miyajima A. Mech Dev. 2009 August-September; 126(8-9):665-76. doi: 10.1016/j.mod.2009.06.939. Epub 2009 Jun. 13.
25. Hepatoblasts comprise a niche for fetal liver erythropoiesis through cytokine production. Sugiyama D, Kulkeaw K, Mizuochi C, Horio Y, Okayama S. Biochem Biophys Res Commun. 2011 Jul. 1; 410(2):301-6. doi: 10.1016/j.bbrc.2011.05.137. Epub 2011 May 30
26. Human fetal hepatic progenitor cells are distinct from, but closely related to, hematopoietic stem/progenitor cells. Chen Q, Khoury M, Limmon G, Choolani M, Chan J K, Chen J. Stem Cells. 2013 June; 31(6):1160-9. doi: 10.1002/stem.1359.
27. Hematopoietic specification from human pluripotent stem cells: current advances and challenges toward de novo generation of hematopoietic stem cells. Slukvin I I. Blood. 2013 Dec. 12; 122(25):4035-46. doi: 10.1182/blood-2013-07-474825. Epub 2013 October
28. Retinoic acid in development: towards an integrated view. Niederreither K, Dollé P. Nat Rev Genet. 2008 July; 9(7):541-53. doi: 10.1038/nrg2340. Epub 2008 Jun. 10.
29. A regulatory loop involving PAX6, MITF, and WNT signaling controls retinal pigment epithelium development. Bharti K, Gasper M, Ou J, Brucato M, Clore-Gronenbom K, Pickel J, Amheiter H. PLoS Genet. 2012 July; 8(7):e1002757. doi: 10.1371/journal.pgen.1002757. Epub 2012 Jul. 5.
30. Efficient generation of human iPSCs by a synthetic self-replicative RNA. Yoshioka N, Gros E, Li H R, Kumar S, Deacon D C, Maron C, Muotri A R, Chi N C, Fu X D, Yu B D, Dowdy S F. Cell Stem Cell. 2013 Aug. 1; 13(2):246-54. doi: 10.1016/j.stem.2013.06.001.
31. Induced pluripotent stem cell lines derived from human somatic cells. Yu J, et al. Science. 2007. 318: 1917-1920.
32. Induction of pluripotent stem cells from mouse fibroblasts by four transcription factors. Yamanaka S. Cell Prolif. 2008 February; 41 Suppl 1:51-6. doi: 10.1111/j.1365-2184.2008.00493.x.
33. Generation of human-induced pluripotent stem cells. Park I H, Lerou P H, Zhao R, Huo H, Daley G Q. Nat Protoc. 2008; 3(7):1180-6. doi: 10.1038/nprot.2008.92.
34. Generation of human induced pluripotent stem cells by direct delivery of reprogramming proteins. Cell Stem Cell. 2009 Jun. 5; 4(6):472-6. doi: 10.1016/j.stem.2009.05.005. Epub 2009 May 28.
35. Human pluripotent stem cell culture: considerations for maintenance, expansion, and therapeutics. Cell Stem Cell. 2014 Jan. 2; 14(1):13-26. doi:10.1016/j.stem.2013.12.005.
36. Biomicrocapsule membrane for cell and tissue transplantation. Ma X, HeY, Xiong Y. Zhonghua Zheng Xing Wai Ke Za Zhi 2000 September; 16(5):267-9.
37. Derivation of human embryonic stem cells in defined conditions. Ludwig, T. E., et al. Nat. Biotechnol. 2006; 24:185-187.
38. Human pluripotent stem cell culture: considerations for maintenance, expansion, and therapeutics. Chen K G, et al. Cell Stem Cell. 2014; 14:13-26.
39. Generation of human induced pluripotent stem cells by direct delivery of reprogramming proteins. Kim D., et al. Cell Stem Cell. 2009; 4(6):472-476.
40. Developing high-fidelity hepatotoxicity models from plutipotent stem cells. Medine, C N, et al. Stem Cells Trans Med. 2013. 2:505-509.
41. A High-Throughput Screen for Teratogens Using Human Pluripotent Stem Cells. Kameoka, S. et al. Toxicological Sciences. 2014; 137(1): 76-90.
42. Modeling inherited metabolic disorders of the liver using human induced pluripotent stem cells. Rashid S T., et al. 2010. 120(9):3127-3136.
43. Human pluripotent stem cells for modelling human liver diseases and cell therapy. Dianat N, et al. Current Gene Therapy. 2013; 13:120-132.
44. Integrating human pluripotent stem cells into drug development. Engle S. et al. Cell Stem Cell. 2013; 12:669-677.

What is claimed is:

1. A method comprising: culturing, in cell culture media under inducing conditions, human induced pluripotent stem (hiPS) cells genetically modified to comprise a nucleic acid comprising an inducible promoter operably linked to a nucleic acid encoding GATA6 protein, whereby upon expression of the nucleic acid, the hiPS cells differentiate into a heterogeneous cell population comprising mesodermal cells, endodermal cells, and ectodermal cells, wherein the induced expression of GATA6 results in an increased subpopulation of endoderm cells compared to that of a cell population derived in the absence of said GATA6 expression.

2. The method of claim 1, further comprising culturing the heterogeneous cell population under conditions sufficient to result in differentiation of the heterogeneous cell population into heterogeneous tissue.

3. The method of claim 1, wherein the hiPS cells are cultured for at least 7 to 15 days.

4. The method of claim 2, wherein the heterogeneous tissue comprises hepatic endodermal cells, hepatoblast-like cells, cholangiocyte-like cells, endothelial progenitor cells, endothelial-like cells, hemogenic endothelial cells, erythrocyte-like cells, hematopoietic progenitor-like cells, mesenchymal progenitor cells, stellate-like cells, neurectodermal cells, neural plate-like cells, neural fold-like cells, or any combination thereof.

5. The method of claim 2, wherein cells of the heterogeneous tissue are:
FOXA2$^+$ and/or SOX17$^+$; CEBPA$^+$, HNF4A$^+$, FOXA2$^+$ and/or HHEX$^+$; CD133$^+$, AAT$^+$, CEBPA$^+$, FOXA2$^+$, AFP$^+$, LGR5$^+$, CK19$^+$, DLK1$^+$ and/or ALB$^+$; CK7$^+$ and/or AQP1$^+$; T$^+$; CD51$^+$, NES$^+$ and/or PDGFRA$^+$; CD34$^+$ and/or CEBPA$^-$; NES$^+$ and/or PDGFRA$^+$; DES$^+$; CD31$^+$; CD34$^+$, TAL1$^+$, FLK1$^+$ and/or CD93$^+$; hemoglobin$^+$; CD45$^+$; OCT4$^+$, SOX10$^+$ and/or NES$^+$; OCT4$^+$, SOX10$^+$ and/or AP2A$^+$; OCT4$^-$, SOX10$^+$ and/or AP2A$^-$; or PAX7$^+$, DLX5$^+$, FOXG1$^+$ and/or PAX6$^+$.

6. The method of claim 1, wherein cytokines and/or growth factors are not added to the cell culture media.

7. The method of claim 1, wherein the cell culture media does not contain serum.

8. A heterogeneous tissue produced by the method of claim 2.

9. A method comprising expressing a nucleic acid encoding GATA6 protein in human induced pluripotent stem (hiPS) cells, wherein the method comprises:
(i) introducing into hiPS cells (a) a first nucleic acid encoding a constitutively expressed doxycycline-activatable transactivator (rtTa) and (b) a second nucleic acid encoding GATA6 protein operably linked to a promoter that comprises a binding site for rtTA; and
(ii) culturing the hiPS cells in the presence of doxycycline to activate expression of the nucleic acid encoding GATA6 protein to result in differentiation of the hiPS cells into a heterogeneous cell population comprising mesodermal cells, endodermal cells, and ectodermal cells, wherein the induced expression of GATA6 results in an increased subpopulation of endoderm cells compared to that of a cell population derived in the absence of said GATA6 expression.

10. The method of claim 1 wherein the hiPS cells are obtained by isolating somatic cells from a human and inducing pluripotency in the isolated somatic cells to produce the hiPS cells.

11. The method of claim 2, wherein the heterogeneous tissue comprises cells that are positive for fibrinogen (Fib), AAT, CEBPα, LGR5, HNF4α, CK19 and DLK1 expression.

12. A heterogeneous tissue produced by the method of claim 11.

* * * * *

SEQUENCE LISTING

```
<160> NUMBER OF SEQ ID NOS: 43

<210> SEQ ID NO 1
<211> LENGTH: 3770
<212> TYPE: DNA
<213> ORGANISM: Homo sapiens

<400> SEQUENCE: 1
gacccacagc ctggcaccct tcggcgagcg ctgtttgttt agggctcggt gagtccaatc      60
aggagcccag gctgcagttt tccggcagag cagtaagagg cgcctcctct ctccttttta     120
ttcaccagca gcgcggcgca gaccccggac tcgcgctcgc ccgctggcgc cctcggcttc     180
tctccgcgcc tgggagcacc ctccgccgcg gccgttctcc atgcgcagcg cccgcccgag     240
gagctagacg tcagcttgga gcggcgccgg accgtggatg gccttgactg acggcggctg     300
gtgcttgccg aagcgcttcg gggccgcggg tgcggacgcc agcgactcca gagcctttcc     360
agcgcgggag ccctccacgc cgccttcccc catctcttcc tcgtcctcct cctgctcccg     420
gggcggagag cggggccccg gcggcgccag caactgcggg acgcctcagc tcgacacgga     480
ggcggcggcc ggaccccgg cccgctcgct gctgctcagt tcctacgctt cgcatccctt     540
cggggctccc cacggacctt cggcgcctgg ggtcgcgggc cccggggggca acctgtcgag     600
```

```
ctgggaggac ttgctgctgt tcactgacct cgaccaagcc gcgaccgcca gcaagctgct    660
gtggtccagc cgcggcgcca agctgagccc cttcgcaccc gagcagccgg aggagatgta    720
ccagaccctc gccgctctct ccagccaggg tccggccgcc tacgacggcg cgcccggcgg    780
cttcgtgcac tctgcggccg cggcggcagc agccgcggcg gcggccagct ccccggtcta    840
cgtgcccacc acccgcgtgg gttccatgct gcccggccta ccgtaccacc tgcaggggtc    900
gggcagtggg ccagccaacc acgcgggcgg cgcgggcgcg caccccggct ggcctcaggc    960
ctcggccgac agccctccat acggcagcgg aggcggcgcg gctggcggcg gggccgcggg   1020
gcctggcggc gctggctcag ccgcggcgca cgtctcggcg cgcttcccct actctcccag   1080
cccgcccatg gccaacggcg ccgcgcggga ccgggaggc tacgcggcgg cgggcagtgg   1140
gggcgcggga ggcgtgagcg gcggcggcag tagcctggcg gccatgggcg ccgcgagcc   1200 ccagtacagc tcgctgtcgg ccgcgcggcc gctgaacggg acgtaccacc accaccacca   1260
ccaccaccac caccatccga gcccctactc gccctacgtg ggggcgccac tgacgcctgc   1320
ctggcccgcc ggacccttcg agaccccggt gctgcacagc ctgcagagcc gcgccggagc   1380
cccgctcccg gtgccccggg gtcccagtgc agacctgctg gaggacctgt ccgagagccg   1440
cgagtgcgtg aactgcggct ccatccagac gccgctgtgg cggcgggacg caccggcca   1500 ctacctgtgc aacgcctgcg ggctctacag caagatgaac ggcctcagcc ggcccctcat   1560
caagccgcag aagcgcgtgc cttcatcacg gcggcttgga ttgtcctgtg ccaactgtca   1620
caccacaact accaccttat ggcgcagaaa cgccgagggt gaacccgtgt gcaatgcttg   1680
tggactctac atgaaactcc atggggtgcc cagaccactt gctatgaaaa agagggaat   1740 tcaaaccagg aaacgaaaac ctaagaacat aaataaatca agacttgct ctggtaatag   1800 caataattcc attcccatga ctccaacttc cacctcttct aactcagatg attgcagcaa   1860
aaatacttcc cccacaacac aacctacagc ctcaggggcg ggtgccccgg tgatgactgg   1920
tgcgggagag agcaccaatc ccgagaacag cgagctcaag tattcgggtc aagatgggct   1980
ctacataggc gtcagtctcg cctcgccggc cgaagtcacg tcctccgtgc gaccggattc   2040
ctggtgcgcc ctggccctgg cctgagccca cgccgccagg aggcagggag ggctccgccg   2100
cgggcctcac tccactcgtg tctgcttttg tgcagcggtc cagacagtgg cgactgcgct   2160
gacagaacgt gattctcgtg cctttatttt gaaagagatg ttttttcccaa gaggcttgct   2220 gaaagagtga gagaagatgg aagggaaggg ccagtgcaac tgggcgcttg ggccactcca   2280
gccagcccgc ctccggggcg gaccctgctc cacttccaga agccaggact aggacctggg   2340
ccttgcctgc tatggaatat tgagagagat ttttttaaaaa agattttgca ttttgtccaa   2400
aatcatgtgc ttcttctgat caattttggt tgttccagaa tttcttcata cctttttccac   2460 atccagattt catgtgcgtt catggagaag atcacttgag gccatttggt acacatctct   2520
ggaggctgag tcggttcatg aggtctctta tcaaaaatat tactcagttt gcaagactgc   2580
attgtaactt taacatacac tgtgactgac gtttctcaaa gttcatattg tgtggctgat   2640
ctgaagtcag tcggaatttg taaacagggt agcaaacaag atattttctcc tccatgtata   2700 caataatttt tttaaaaagt gcaatttgcg ttgcagcaat cagtgttaaa tcatttgcat   2760
aagatttaac agcattttt ataatgaatg taaacatttt aacttaatgg tacttaaaat   2820
aatttaaaag aaaaatgtta acttagacat tcttatgctt cttttacaac tacatcccat   2880
tttatatttc caattgttaa agaaaaatat ttcaagaaca aatcttctct caggaaaatt   2940
```

-continued

```
gcctttctct atttgttaag aattttttata caagaacacc aatataccccc ctttatttta    3000
ctgtggaata tgtgctggaa aaattgcaac aacactttac tacctaacgg atagcatttg    3060
taaatactct aggtatctgt aaacactctg atgaagtctg tatagtgtga ctaacccaca    3120
ggcaggttgg tttacattaa ttttttttt tgaatgggat gtcctatgga aacctatttc    3180
accagagttt taaaaataaa aagggtattg ttttgtcttc tgtacagtga gttccttccc    3240
ttttcaaagc tttcttttta tgctgtatgt gactatagat attcatataa aacaagtgca    3300
cgtgaagttt gcaaaatgct ttaaggcctt cctttcaaag catagtcctt ttggagccgt    3360
tttgtacctt ttataccttg gcttatttga agttgacaca tggggttagt tactactctc    3420
catgtgcatt ggggacagtt tttataagtg ggaaggactc agtattatta tatttgagat    3480
gataagcatt ttgtttggga acaatgctta aaaatattcc agaaagttca gattttttt    3540
ctttgtgaat gaaatatatt ctggcccacg aacagggcga tttcctttca gtttttcct    3600
tttgcaacgt gccttgaagt ctcaaagctc acctgaggtt gcagacgtta cccccaacag    3660
aagataggta gaaatgattc cagtggcctc tttgtatttt cttcattgtt gagtagattt    3720
caggaaatca ggaggtgttt cacaatacag aatgatggcc tttaactgtg              3770
```

<210> SEQ ID NO 2
<211> LENGTH: 595
<212> TYPE: PRT
<213> ORGANISM: Homo sapiens

<400> SEQUENCE: 2

```
Met Ala Leu Thr Asp Gly Gly Trp Cys Leu Pro Lys Arg Phe Gly Ala
1               5                   10                  15

Ala Gly Ala Asp Ala Ser Asp Ser Arg Ala Phe Pro Ala Arg Glu Pro
            20                  25                  30

Ser Thr Pro Pro Ser Pro Ile Ser Ser Ser Ser Ser Cys Ser Arg
        35                  40                  45

Gly Gly Glu Arg Gly Pro Gly Gly Ala Ser Asn Cys Gly Thr Pro Gln
    50                  55                  60

Leu Asp Thr Glu Ala Ala Ala Gly Pro Pro Ala Arg Ser Leu Leu Leu
65                  70                  75                  80

Ser Ser Tyr Ala Ser His Pro Phe Gly Ala Pro His Gly Pro Ser Ala
                85                  90                  95

Pro Gly Val Ala Gly Pro Gly Gly Asn Leu Ser Ser Trp Glu Asp Leu
            100                 105                 110

Leu Leu Phe Thr Asp Leu Asp Gln Ala Ala Thr Ala Ser Lys Leu Leu
        115                 120                 125

Trp Ser Ser Arg Gly Ala Lys Leu Ser Pro Phe Ala Pro Glu Gln Pro
    130                 135                 140

Glu Glu Met Tyr Gln Thr Leu Ala Ala Leu Ser Ser Gln Gly Pro Ala
145                 150                 155                 160

Ala Tyr Asp Gly Ala Pro Gly Gly Phe Val His Ser Ala Ala Ala
                165                 170                 175

Ala Ala Ala Ala Ala Ala Ala Ser Ser Pro Val Tyr Val Pro Thr Thr
            180                 185                 190

Arg Val Gly Ser Met Leu Pro Gly Leu Pro Tyr His Leu Gln Gly Ser
        195                 200                 205

Gly Ser Gly Pro Ala Asn His Ala Gly Gly Ala Gly Ala His Pro Gly
    210                 215                 220

Trp Pro Gln Ala Ser Ala Asp Ser Pro Pro Tyr Gly Ser Gly Gly Gly
```

```
                225                 230                 235                 240
        Ala Ala Gly Gly Gly Ala Ala Gly Pro Gly Ala Gly Ser Ala Ala
                            245                 250                 255

Ala His Val Ser Ala Arg Phe Pro Tyr Ser Pro Ser Pro Met Ala
                            260                 265                 270

Asn Gly Ala Ala Arg Glu Pro Gly Gly Tyr Ala Ala Ala Gly Ser Gly
                            275                 280                 285

Gly Ala Gly Gly Val Ser Gly Gly Gly Ser Ser Leu Ala Ala Met Gly
                            290                 295                 300

Gly Arg Glu Pro Gln Tyr Ser Ser Leu Ser Ala Ala Arg Pro Leu Asn
        305                 310                 315                 320

Gly Thr Tyr His His His His His His His His Pro Ser Pro
                                325                 330                 335

Tyr Ser Pro Tyr Val Gly Ala Pro Leu Thr Pro Ala Trp Pro Ala Gly
                            340                 345                 350

Pro Phe Glu Thr Pro Val Leu His Ser Leu Gln Ser Arg Ala Gly Ala
                            355                 360                 365

Pro Leu Pro Val Pro Arg Gly Pro Ser Ala Asp Leu Leu Glu Asp Leu
                370                 375                 380

Ser Glu Ser Arg Glu Cys Val Asn Cys Gly Ser Ile Gln Thr Pro Leu
        385                 390                 395                 400

Trp Arg Arg Asp Gly Thr Gly His Tyr Leu Cys Asn Ala Cys Gly Leu
                            405                 410                 415

Tyr Ser Lys Met Asn Gly Leu Ser Arg Pro Leu Ile Lys Pro Gln Lys
                            420                 425                 430

Arg Val Pro Ser Ser Arg Arg Leu Gly Leu Ser Cys Ala Asn Cys His
                        435                 440                 445

Thr Thr Thr Thr Thr Leu Trp Arg Arg Asn Ala Glu Gly Glu Pro Val
                450                 455                 460

Cys Asn Ala Cys Gly Leu Tyr Met Lys Leu His Gly Val Pro Arg Pro
        465                 470                 475                 480

Leu Ala Met Lys Lys Glu Gly Ile Gln Thr Arg Lys Arg Lys Pro Lys
                            485                 490                 495

Asn Ile Asn Lys Ser Lys Thr Cys Ser Gly Asn Ser Asn Asn Ser Ile
                        500                 505                 510

Pro Met Thr Pro Thr Ser Thr Ser Ser Asn Ser Asp Asp Cys Ser Lys
                    515                 520                 525

Asn Thr Ser Pro Thr Thr Gln Pro Thr Ala Ser Gly Ala Gly Ala Pro
                530                 535                 540

Val Met Thr Gly Ala Gly Glu Ser Thr Asn Pro Glu Asn Ser Glu Leu
        545                 550                 555                 560

Lys Tyr Ser Gly Gln Asp Gly Leu Tyr Ile Gly Val Ser Leu Ala Ser
                            565                 570                 575

Pro Ala Glu Val Thr Ser Ser Val Arg Pro Asp Ser Trp Cys Ala Leu
                        580                 585                 590

Ala Leu Ala
                595

<210> SEQ ID NO 3
<211> LENGTH: 3419
<212> TYPE: DNA
<213> ORGANISM: Homo sapiens

<400> SEQUENCE: 3
```

-continued

| | | | | | |
|---|---|---|---|---|---|
| ttggaggcgg | ccggcgcagg | ggccgcgaga | ggcttcgtcg | ccgctgcagc | tccgggggct | 60 |
| cccaggggag | cgtgcgcgga | acctccaggc | ccagcaggac | cccggctgcg | gcaggagga | 120 |
| aggagccagc | ctagcagctt | ctgcgcctgt | ggccgcgggt | gtcctggagg | cctctcggtg | 180 |
| tgacgagtgg | gggaccccgaa | ggctcgtgcg | ccacctccag | gctgacgc | tgccctccgt | 240 |
| cttctgcccc | caataggtgc | gccggacctt | caggccctgg | ggtgaattca | gctgctccta | 300 |
| catcagcttc | cggaaccacc | aaaaattcaa | attgggattt | tccggagtaa | acaagagcct | 360 |
| agagcccttt | gctcaatgct | ggatttaata | cgtatatatt | tttaagcgag | ttggtttttt | 420 |
| cccctttgat | ttttgatctt | cgcgacagtt | cctcccacgc | atattatcgt | tgttgccgtc | 480 |
| gttttctctc | cccgcgtggc | tccttgacct | gcgagggaga | gagaggacac | cgaagccggg | 540 |
| agctcgcagg | gaccatgtat | cagagcttgg | ccatggccgc | caaccacggg | ccgcccccg | 600 |
| gtgcctacga | ggcgggcggc | cccggcgcct | tcatgacgg | cgcgggcgcc | gcgtcctcgc | 660 |
| cagtctacgt | gcccacaccg | cgggtgccct | cctccgtgct | gggcctgtcc | tacctccagg | 720 |
| gcggaggcgc | gggctctgcg | tccggaggcg | cctcgggcgg | cagctccggt | ggggccgcgt | 780 |
| ctggtgcggg | gccgggacc | cagcagggca | gcccgggatg | gagccaggcg | ggagccgacg | 840 |
| gagccgctta | caccccgccg | ccggtgtcgc | cgcgcttctc | cttcccgggg | accaccgggt | 900 |
| ccctggcggc | cgccgccgcc | gctgccgcgg | cccgggaagc | tgcggcctac | agcagtggcg | 960 |
| gcggagcggc | gggtgcgggc | ctggcgggcc | gcgagcagta | cggcgcgcc | ggcttcgcgg | 1020 |
| gctcctactc | cagcccctac | ccggcttaca | tggccgacgt | gggcgcgtcc | tgggccgcag | 1080 |
| ccgccgccgc | ctccgccggc | ccttcgaca | gcccggtcct | gcacagcctg | cccggccggg | 1140 |
| ccaacccggc | cgcccgacac | cccaatctcg | atatgtttga | cgacttctca | gaaggcagag | 1200 |
| agtgtgtcaa | ctgtggggct | atgtccaccc | cgctctggag | gcgagatggg | acgggtcact | 1260 |
| atctgtgcaa | cgcctgcggc | ctctaccaca | agatgaacgg | catcaaccgg | ccgctcatca | 1320 |
| agcctcagcg | ccggctgtcc | gcctcccgcc | gagtgggcct | ctcctgtgcc | aactgccaga | 1380 |
| ccaccaccac | cacgctgtgg | cgccgcaatg | cggagggcga | gcctgtgtgc | aatgcctgcg | 1440 |
| gcctctacat | gaagctccac | ggggtcccca | ggctcttgc | aatgcggaaa | gaggggatcc | 1500 |
| aaaccagaaa | acggaagccc | aagaacctga | ataaatctaa | gacaccagca | gctccttcag | 1560 |
| gcagtgagag | ccttcctccc | gccagcggtg | cttccagcaa | ctccagcaac | gccaccacca | 1620 |
| gcagcagcga | ggagatgcgt | cccatcaaga | cggagcctgg | cctgtcatct | cactacgggc | 1680 |
| acagcagctc | cgtgtcccag | acgttctcag | tcagtgcgat | gtctggccat | gggccctcca | 1740 |
| tccaccctgt | cctctcggcc | ctgaagctct | ccccacaagg | ctatgcgtct | cccgtcagcc | 1800 |
| agtctccaca | gaccagctcc | aagcaggact | cttggaacag | cctggtcttg | gccgacagtc | 1860 |
| acgggggacat | aatcactgcg | taatcttccc | tcttccctcc | tcaaattcct | gcacggacct | 1920 |
| gggacttgga | ggatagcaaa | gaaggaggcc | ctgggctccc | aggggccggc | ctcctctgcc | 1980 |
| tggtaatgac | tccagaacaa | caactgggaa | gaaacttgaa | gtcgacaatc | tggttagggg | 2040 |
| aagcgggtgt | tggattttct | cagatgcctt | tacacgctga | tgggactgga | gggagcccac | 2100 |
| ccttcagcac | gagcacactg | catctctcct | gtgagttgga | gacttctttc | ccaagatgtc | 2160 |
| cttgtcccct | gcgttcccca | ctgtggccta | gaccgtgggt | tttgcattgt | gtttctagca | 2220 |
| ccgaggatct | gagaacaagc | ggagggccgg | gccctgggac | ccctgctcca | gcccgaatga | 2280 |
| cggcatctgt | ttgccatgta | cctggatgcg | acgggcccct | ggggacaggc | ccttgcccca | 2340 |
| tccatccgct | tgaggcatgg | caccgccctg | catccctaat | accaaatctg | actccaaaat | 2400 |

```
tgtgggtgt gacatacaag tgactgaaca cttcctgggg agctacaggg gcacttaacc    2460
caccacagca cagcctcatc aaaatgcagc tggcaacttc tccccccaggt gccttccccc    2520 tgctgccggc ctttgctcct tcacttccaa catctctcaa aataaaaatc cctcttcccg    2580
ctctgagcga ttcagctctg cccgcagctt gtacatgtct ctcccctggc aaaacaagag    2640
ctgggtagtt tagccaaacg gcaccccctc gagttcactg cagacccttc gttcaccgtg    2700
tcacacatag aggggttctg agtaagaaca aaacgttctg ctgctcaagc cagtctggca    2760
agcactcagc ccagcctcga ggtccttctg gggagagtgt aagtggacag agtcctggtc    2820 aggggggcagg agtgtcccaa gggctggccc acctgctgtc tgtctgctcc tcctagccct    2880
tggtcagatg gcagccagag tccctcagga cctgcagcct cgccccggca gaagtctttt    2940
gtccaggagg caaaaagcca gagattctgc aacacgaatt cgaagcaaac aaacacaaca    3000
caacagaatt cctggaaaga agacgactgc taagacacgg caggggggcc tggagggagc    3060
ctccgactct gagctgctcc gggatctgcc gcgttctcct ctgcacattg ctgtttctgc    3120
ccctgatgct ggagctcaag gagactcctt cctctttctc agcagagctg tagctgactg    3180
tggcattact acgcctcccc acacgcccag acccctcact ccaaaatcct actggctgta    3240
gcagagaata cctttgaacc aagattctgt tttaatcatc atttacattg ttttcttcca    3300
aaggccccct cgtatacccct ccctaaccca caaacctgtt aacattgtct taaggtgaaa    3360
tggctggaaa atcagtattt aactaataaa tttatctgta ttcctcttaa aaaaaaaaa    3419
```

<210> SEQ ID NO 4
<211> LENGTH: 442
<212> TYPE: PRT
<213> ORGANISM: Homo sapiens

<400> SEQUENCE: 4

```
Met Tyr Gln Ser Leu Ala Met Ala Ala Asn His Gly Pro Pro Pro Gly
1               5                   10                  15

Ala Tyr Glu Ala Gly Gly Pro Gly Ala Phe Met His Gly Ala Gly Ala
            20                  25                  30

Ala Ser Ser Pro Val Tyr Val Pro Thr Pro Arg Val Pro Ser Ser Val
        35                  40                  45

Leu Gly Leu Ser Tyr Leu Gln Gly Gly Ala Gly Ser Ala Ser Gly
    50                  55                  60

Gly Ala Ser Gly Gly Ser Ser Gly Gly Ala Ser Gly Ala Gly Pro
65                  70                  75                  80

Gly Thr Gln Gln Gly Ser Pro Gly Trp Ser Gln Ala Gly Ala Asp Gly
                85                  90                  95

Ala Ala Tyr Thr Pro Pro Pro Val Ser Pro Arg Phe Ser Phe Pro Gly
            100                 105                 110

Thr Thr Gly Ser Leu Ala Ala Ala Ala Ala Ala Ala Ala Arg Glu
        115                 120                 125

Ala Ala Ala Tyr Ser Ser Gly Gly Ala Ala Gly Ala Gly Leu Ala
    130                 135                 140

Gly Arg Glu Gln Tyr Gly Arg Ala Gly Phe Ala Gly Ser Tyr Ser Ser
145                 150                 155                 160

Pro Tyr Pro Ala Tyr Met Ala Asp Val Gly Ala Ser Trp Ala Ala Ala
                165                 170                 175

Ala Ala Ala Ser Ala Gly Pro Phe Asp Ser Pro Val Leu His Ser Leu
            180                 185                 190
```

Pro Gly Arg Ala Asn Pro Ala Ala Arg His Pro Asn Leu Asp Met Phe
        195                 200                 205

Asp Asp Phe Ser Glu Gly Arg Glu Cys Val Asn Cys Gly Ala Met Ser
    210                 215                 220

Thr Pro Leu Trp Arg Arg Asp Gly Thr Gly His Tyr Leu Cys Asn Ala
225                 230                 235                 240

Cys Gly Leu Tyr His Lys Met Asn Gly Ile Asn Arg Pro Leu Ile Lys
            245                 250                 255

Pro Gln Arg Arg Leu Ser Ala Ser Arg Val Gly Leu Ser Cys Ala
                260                 265                 270

Asn Cys Gln Thr Thr Thr Thr Thr Leu Trp Arg Arg Asn Ala Glu Gly
        275                 280                 285

Glu Pro Val Cys Asn Ala Cys Gly Leu Tyr Met Lys Leu His Gly Val
    290                 295                 300

Pro Arg Pro Leu Ala Met Arg Lys Glu Gly Ile Gln Thr Arg Lys Arg
305                 310                 315                 320

Lys Pro Lys Asn Leu Asn Lys Ser Lys Thr Pro Ala Ala Pro Ser Gly
            325                 330                 335

Ser Glu Ser Leu Pro Pro Ala Ser Gly Ala Ser Ser Asn Ser Ser Asn
                340                 345                 350

Ala Thr Thr Ser Ser Ser Glu Glu Met Arg Pro Ile Lys Thr Glu Pro
        355                 360                 365

Gly Leu Ser Ser His Tyr Gly His Ser Ser Ser Val Ser Gln Thr Phe
    370                 375                 380

Ser Val Ser Ala Met Ser Gly His Gly Pro Ser Ile His Pro Val Leu
385                 390                 395                 400

Ser Ala Leu Lys Leu Ser Pro Gln Gly Tyr Ala Ser Pro Val Ser Gln
            405                 410                 415

Ser Pro Gln Thr Ser Ser Lys Gln Asp Ser Trp Asn Ser Leu Val Leu
                420                 425                 430

Ala Asp Ser His Gly Asp Ile Ile Thr Ala
        435                 440

<210> SEQ ID NO 5
<211> LENGTH: 2350
<212> TYPE: DNA
<213> ORGANISM: Homo sapiens

<400> SEQUENCE: 5

```
gcagtgtcac taggccggct gggggccctg ggtacgctgt agaccagacc gcgacaggcc     60
agaacacggg cggcggcttc gggccgggag acccgcgcag ccctcggggc atctcagtgc    120
ctcactcccc accccctccc ccgggtcggg ggaggcggcg cgtccggcgg agggttgagg    180
ggagcgggc aggcctggag cgccatgagc agcccggatg cgggatacgc cagtgacgac    240
cagagccaga cccagagcgc gctgcccgcg gtgatggccg ggctgggccc ctgcccctgg    300
gccgagtcgc tgagccccat cggggacatg aaggtgaagg cgaggcgcc ggcgaacagc    360
ggagcaccgg ccggggccgc gggccgagcc aagggcgagt cccgtatccg gcggccgatg    420
aacgctttca tggtgtgggc taaggacgag cgcaagcggc tggcgcagca gaatccagac    480
ctgcacaacg ccgagttgag caagatgctg ggcaagtcgt ggaaggcgct gacgctggcg    540
gagaagcggc ccttcgtgga ggaggcagag cggctgcgcg tgcagcacat gcaggaccac    600
cccaactaca gtaccggcc gcggcggcgc aagcaggtga agcggctgaa gcgggtggag    660
ggcggcttcc tgcacggcct ggctgagccg caggcggccg cgctgggccc cgagggcggc    720
```

```
cgcgtggcca tggacggcct gggcctccag ttccccgagc agggcttccc cgccggcccg    780
ccgctgctgc ctccgcacat gggcggccac taccgcgact gccagagtct gggcgcgcct    840
ccgctcgacg gctacccgtt gcccacgccc gacacgtccc cgctggacgg cgtggacccc    900
gacccggctt tcttcgccgc cccgatgccc ggggactgcc cggcggccgg cacctacagc    960
tacgcgcagg tctcggacta cgctggcccc ccggagcctc ccgccggtcc catgcacccc   1020
cgactcggcc cagagcccgc gggtccctcg attccgggcc tcctggcgcc acccagcgcc   1080
cttcacgtgt actacggcgc gatgggctcg ccggggcgg cggcgggcg cggcttccag    1140
atgcagccgc aacaccagca ccagcaccag caccagcacc accccccggg ccccggacag   1200
ccgtcgcccc ctccggaggc actgccctgc cgggacggca cggaccccag tcagcccgcc   1260
gagctcctcg gggaggtgga ccgcacggaa tttgaacagt atctgcactt cgtgtgcaag   1320
cctgagatgg gcctccccta ccaggggcat gactccggtg tgaatctccc cgacagccac   1380
ggggccattt cctcggtggt gtccgacgcc agctccgcgg tatattactg caactatcct   1440
gacgtgtgac aggtccctga tccgccccag cctgcaggcc agaagcagtg ttacacactt   1500
cctggaggag ctaaggaaat cctcagactc ctgggttttt gttgttgctg ttgttgtttt   1560
ttaaaaggtg tgttggcata taatttatgg taatttattt tgtctgccac ttgaacagtt   1620
tgggggggtg aggtttcatt taaaatttgt tcagagattt gtttcccata gttggattgt   1680
caaaacccta tttccaagtt caagttaact agctttgaat gtgtcccaaa acagcttcct   1740
ccatttcctg aaagtttatt gatcaaagaa atgttgtcct gggtgtgttt tttcaatctt   1800
ctaaaaaata aaatctggaa tcctgctttt ttgctctact agtacctctg tcacactagt   1860
cttatcaaaa accagttctt aagatcaatg ttaagtttat tagttaatgt aaatttctca   1920
tcctcgaaaa gggtgaacat aaatgccttt aaggagtata tctaaaaata aacattagga   1980
tatctaagtt tgatgtaatt gtttcaggaa ggaaaaaaga aaagcattct ggaatgagcc   2040
tacttcaagt aatcttagtt tctaaaacta acagttaata ttttcaattc cagtatatca   2100
ctttaagtag aaggggatgt ccaagtaatt tggttttcct aactgttgaa tcataagctt   2160
gacctgcccc cagaggcttt ttggatgttt ttatctgtgt tttgccatct ctttacactc   2220
ctcgacattc agtttacctt aatcttcaca tttttacacc ttgggaagtg gcaagcatcg   2280
ctgggtttaa gataaaggag tcacaaaaac taatcaaaat aaaatttgca ttatgacaac   2340
ttttaataca                                                         2350
```

<210> SEQ ID NO 6
<211> LENGTH: 414
<212> TYPE: PRT
<213> ORGANISM: Homo sapiens

<400> SEQUENCE: 6

Met Ser Ser Pro Asp Ala Gly Tyr Ala Ser Asp Asp Gln Ser Gln Thr
1               5                   10                  15

Gln Ser Ala Leu Pro Ala Val Met Ala Gly Leu Gly Pro Cys Pro Trp
            20                  25                  30

Ala Glu Ser Leu Ser Pro Ile Gly Asp Met Lys Val Lys Gly Glu Ala
        35                  40                  45

Pro Ala Asn Ser Gly Ala Pro Ala Gly Ala Ala Gly Arg Ala Lys Gly
    50                  55                  60

Glu Ser Arg Ile Arg Arg Pro Met Asn Ala Phe Met Val Trp Ala Lys
65                  70                  75                  80

-continued

Asp Glu Arg Lys Arg Leu Ala Gln Gln Asn Pro Asp Leu His Asn Ala
                85                  90                  95

Glu Leu Ser Lys Met Leu Gly Lys Ser Trp Lys Ala Leu Thr Leu Ala
            100                 105                 110

Glu Lys Arg Pro Phe Val Glu Ala Glu Arg Leu Arg Val Gln His
        115                 120                 125

Met Gln Asp His Pro Asn Tyr Lys Tyr Arg Pro Arg Arg Lys Gln
130                 135                 140

Val Lys Arg Leu Lys Arg Val Glu Gly Gly Phe Leu His Gly Leu Ala
145                 150                 155                 160

Glu Pro Gln Ala Ala Leu Gly Pro Glu Gly Gly Arg Val Ala Met
            165                 170                 175

Asp Gly Leu Gly Leu Gln Phe Pro Glu Gln Gly Phe Pro Ala Gly Pro
                180                 185                 190

Pro Leu Leu Pro Pro His Met Gly Gly His Tyr Arg Asp Cys Gln Ser
            195                 200                 205

Leu Gly Ala Pro Pro Leu Asp Gly Tyr Pro Leu Pro Thr Pro Asp Thr
    210                 215                 220

Ser Pro Leu Asp Gly Val Asp Pro Asp Pro Ala Phe Phe Ala Ala Pro
225                 230                 235                 240

Met Pro Gly Asp Cys Pro Ala Ala Gly Thr Tyr Ser Tyr Ala Gln Val
            245                 250                 255

Ser Asp Tyr Ala Gly Pro Pro Glu Pro Pro Ala Gly Pro Met His Pro
            260                 265                 270

Arg Leu Gly Pro Glu Pro Ala Gly Pro Ser Ile Pro Gly Leu Leu Ala
            275                 280                 285

Pro Pro Ser Ala Leu His Val Tyr Tyr Gly Ala Met Gly Ser Pro Gly
    290                 295                 300

Ala Gly Gly Gly Arg Gly Phe Gln Met Gln Pro Gln His Gln His Gln
305                 310                 315                 320

His Gln His Gln His His Pro Pro Gly Pro Gly Gln Pro Ser Pro Pro
                325                 330                 335

Pro Glu Ala Leu Pro Cys Arg Asp Gly Thr Asp Pro Ser Gln Pro Ala
            340                 345                 350

Glu Leu Leu Gly Glu Val Asp Arg Thr Glu Phe Glu Gln Tyr Leu His
            355                 360                 365

Phe Val Cys Lys Pro Glu Met Gly Leu Pro Tyr Gln Gly His Asp Ser
    370                 375                 380

Gly Val Asn Leu Pro Asp Ser His Gly Ala Ile Ser Ser Val Val Ser
385                 390                 395                 400

Asp Ala Ser Ser Ala Val Tyr Tyr Cys Asn Tyr Pro Asp Val
            405                 410

<210> SEQ ID NO 7
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 7
gagaacaggt cggatctgta ccaccgctgg ccatgggccc ctagggcgag                50

<210> SEQ ID NO 8
<211> LENGTH: 40

```
<212> TYPE: DNA
<213> ORGANISM: Artificial Sequence
<220> FEATURE:
<223> OTHER INFORMATION: Synthetic Oligonucleotide

<400> SEQUENCE: 8
gctaaaactg gaactgtacg aggggcccct taagcctgag                            40

<210> SEQ ID NO 9
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 9
caaaaggagg tgcagcggcg tccagtcgtc cgacggcgcc gggaggttaa cgaac           55

<210> SEQ ID NO 10
<211> LENGTH: 59
<212> TYPE: DNA
<213> ORGANISM: Artificial Sequence
<220> FEATURE:
<223> OTHER INFORMATION: Synthetic Oligonucleotide

<400> SEQUENCE: 10
agcgccactc aagtccgaaa aagtaccccg gccccaaaag gaggtgcagc ggcgtccag       59

<210> SEQ ID NO 11
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 11
ctagccctct accccctccg attgactcgc cggcgcttaa gatg                      44

<210> SEQ ID NO 12
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 12
cggcggcagt cagttccggt accaccgctt ggaactctgg ttt                       43

<210> SEQ ID NO 13
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 13
acggggcccc agggtcacgt cactctggaa a                                    31

<210> SEQ ID NO 14
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 14
```

```
gagcctgtcc aggaggtcgt ccagacgact ctggttt                              37

<210> SEQ ID NO 15
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 15
gttcggcgtc ttcgcgcaca ctctggaaa                                      29

<210> SEQ ID NO 16
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 16
gttaggttcg gcggcactac ttccgtgcac tctggttt                            38

<210> SEQ ID NO 17
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 17
gaacacctga gatgtacttt gaggtaccca ctctggaaa                           39

<210> SEQ ID NO 18
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 18
gagaaaaaag tatcgttcac cagacccgtg gggtactctg gttt                     44

<210> SEQ ID NO 19
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 19
ggattcttgt atttatttag tttctgaacg agacactctg gaaa                     44

<210> SEQ ID NO 20
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 20
caacctcagt acccttacct taataacgat aatggtctac tctggttt                 48

<210> SEQ ID NO 21
<211> LENGTH: 37
<212> TYPE: DNA
<213> ORGANISM: Artificial Sequence
```

```
<220> FEATURE:
<223> OTHER INFORMATION: Synthetic Oligonucleotide

<400> SEQUENCE: 21
ggggtgttgt gttggatgtc ggagtccact ctggaaa                              37

<210> SEQ ID NO 22
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 22
gtcagtagtg gccccgtggg cggggacact ctggttt                              37

<210> SEQ ID NO 23
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 23
cgcgggaccg ggaccggact cgaaactctg gaaa                                 34

<210> SEQ ID NO 24
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 24
cggcggcagt cagttccggt accaccgctc ggacgaaaaa acatgtttga acagggg        57

<210> SEQ ID NO 25
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 25
cacgagaccg ggaccggact atggtgggtc gaaagaacat gtttcaccag ggg            53

<210> SEQ ID NO 26
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 26
gtcagttccg gtaccaccgc ttggaactct ggttt                                35

<210> SEQ ID NO 27
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 27
cacgcgggac cgggaccggc tccactctgg aaa                                  33
```

<210> SEQ ID NO 28
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 28
ctccaacgcc ccgcgcctcc actctggttt                              30

<210> SEQ ID NO 29
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 29
ccccacgggc ggaaggacct cggagactct ggaaa                        35

<210> SEQ ID NO 30
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 30
cggcagtcag ttccggtacc accattcgga cgaaaaaaca tgtttgaaca gggg   54

<210> SEQ ID NO 31
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 31
cacgcgggac cgggaccggc cgataggaat gctgcacgga ctgatgcgga ctatgggtcg   60
aaagaacatg tttcaccagg gg                                      82

<210> SEQ ID NO 32
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 32
gaggagcggg aacgagtggt accccggccc caaaaggagg tgcagcggcg actctggttt   60

<210> SEQ ID NO 33
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 33
ccgtacctgc tcgacatgtt cattcgaaac tctggaaa                     38

<210> SEQ ID NO 34
<211> LENGTH: 37
<212> TYPE: DNA
<213> ORGANISM: Artificial Sequence

```
<220> FEATURE:
<223> OTHER INFORMATION: Synthetic Oligonucleotide

<400> SEQUENCE: 34
cagttccggt accaccgctt ggatggaact ctggttt                              37

<210> SEQ ID NO 35
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 35
cgtcggacga ctggacgcca ctctggaaa                                       29

<210> SEQ ID NO 36
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 36
gattacttct cgggatcgaa agagctcctt aacgg                                35

<210> SEQ ID NO 37
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 37
gattaaaggg aggcaaacag gatcttaaga agacgtc                              37

<210> SEQ ID NO 38
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 38
gtcgaggagc gggaacgagt ggtaccaccg ctcggacgaa aaaacatgtt tgaacagggg     60

<210> SEQ ID NO 39
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 39
acctgctcga catgttcatt atggtgggtc gaaagaacat gtttcaccag ggg            53

<210> SEQ ID NO 40
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 40
ccctgtcgtc tctaggtcaa accaattaat tcctagg                              37
```

```
<210> SEQ ID NO 41
<211> LENGTH: 46
<212> TYPE: DNA
<213> ORGANISM: Artificial Sequence
<220> FEATURE:
<223> OTHER INFORMATION: Synthetic Oligonucleotide

<400> SEQUENCE: 41
ccaactaata gctattcgaa ctatagctta acggccttaa gtggtg                          46

<210> SEQ ID NO 42
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 42
gcaaagagca agttgaaaag atatgtttca actaattaat tcttaag                         47

<210> SEQ ID NO 43
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 43
gagcaagtcg aaagaacatg tttcaccact taaggccgtt aaccctaag                       49
```